(12) United States Patent
Karabey et al.

(10) Patent No.: US 9,017,361 B2
(45) Date of Patent: Apr. 28, 2015

(54) OCCLUSIVE IMPLANT AND METHODS FOR HOLLOW ANATOMICAL STRUCTURE

(75) Inventors: Halil Ibrahim Karabey, San Jose, CA (US); Michael S. Mirizzi, San Jose, CA (US); Anna Grace Prestezog, Sunnyvale, CA (US)

(73) Assignee: Covidien LP, Mansfield, MA (US)

( * ) Notice: Subject to any disclaimer, the term of this patent is extended or adjusted under 35 U.S.C. 154(b) by 1322 days.

(21) Appl. No.: 11/407,858

(22) Filed: Apr. 20, 2006

(65) Prior Publication Data

US 2007/0248640 A1 Oct. 25, 2007

(51) Int. Cl.
| | |
|---|---|
| *A61M 29/00* | (2006.01) |
| *A61B 17/08* | (2006.01) |
| *A61B 17/12* | (2006.01) |
| *A61B 17/00* | (2006.01) |
| *A61B 17/04* | (2006.01) |
| *A61B 17/06* | (2006.01) |

(52) U.S. Cl.
CPC ....... *A61B 17/12022* (2013.01); *A61B 17/0057* (2013.01); *A61B 17/0401* (2013.01); *A61B 17/12036* (2013.01); *A61B 17/12109* (2013.01); *A61B 17/12159* (2013.01); *A61B 17/12172* (2013.01); *A61B 17/12181* (2013.01); *A61B 17/1219* (2013.01); *A61B 2017/00637* (2013.01); *A61B 2017/00641* (2013.01); *A61B 2017/00654* (2013.01); *A61B 2017/0443* (2013.01); *A61B 2017/06176* (2013.01); *A61B 2017/1205* (2013.01)

(58) Field of Classification Search
USPC .......................... 606/200, 213, 151, 157, 158
See application file for complete search history.

(56) References Cited

U.S. PATENT DOCUMENTS

| | | |
|---|---|---|
| 1,941,717 A | 1/1934 | Rabell |
| 2,286,817 A | 6/1942 | Knight |
| 2,711,173 A | 6/1955 | Seidler |
| 2,733,714 A | 2/1956 | Haas |
| 2,934,068 A | 4/1960 | Graham, Jr. |
| 2,961,374 A | 11/1960 | Lieb et al. |
| 3,063,453 A | 11/1962 | Brecht |
| 3,177,872 A | 4/1965 | Pearman |
| 3,297,033 A | 1/1967 | Schmitt et al. |
| 3,320,956 A | 5/1967 | Steiger |
| 3,431,909 A | 3/1969 | Krusko |

(Continued)

FOREIGN PATENT DOCUMENTS

| | | |
|---|---|---|
| EP | 0 778 005 A1 | 6/1997 |
| EP | 0778005 A1 | 6/1997 |

(Continued)

OTHER PUBLICATIONS

Specification of U.S. Appl. No. 60/502,702, filed Sep. 12, 2003, Develian, Carol.

(Continued)

*Primary Examiner* — Dianne Dornbusch
(74) *Attorney, Agent, or Firm* — Thomas M. Johnston, Esq.

(57) ABSTRACT

Apparatus and methods for treating a hollow anatomical structure comprises an implant sized for insertion into a hollow anatomical structure. The implant comprises a plurality of loose, bulked fibers. The fibers are formed from one or more bioabsorbable materials. Upon implantation, the apparatus causes a partial occlusion of the hollow anatomical structure, followed by a complete or substantially complete occlusion.

20 Claims, 54 Drawing Sheets

(56) References Cited

U.S. PATENT DOCUMENTS

| | | | |
|---|---|---|---|
| 3,463,158 A | 8/1969 | Schmitt et al. | |
| 3,687,129 A | 8/1972 | Nuwayser | |
| 3,699,965 A | 10/1972 | Dostal | |
| 3,739,773 A | 6/1973 | Schmitt et al. | |
| 4,002,173 A | 1/1977 | Manning et al. | |
| 4,027,676 A | 6/1977 | Mattei | |
| 4,148,317 A | 4/1979 | Loyer | |
| 4,173,228 A | 11/1979 | Van Steenwyk et al. | |
| 4,185,618 A | 1/1980 | Corey | |
| 4,268,495 A | 5/1981 | Muxfeldt et al. | |
| 4,509,504 A | 4/1985 | Brundin | |
| 4,650,488 A | 3/1987 | Bays et al. | |
| 4,655,771 A | 4/1987 | Wallsten | |
| 4,655,777 A | 4/1987 | Dunn et al. | |
| 4,668,233 A | 5/1987 | Seedhom et al. | |
| 4,700,701 A | 10/1987 | Montaldi | |
| 4,832,055 A | 5/1989 | Palestrant | |
| 4,916,193 A | 4/1990 | Tang et al. | |
| 4,938,763 A | 7/1990 | Dunn et al. | |
| 4,942,875 A | 7/1990 | Hlavacek et al. | |
| 4,994,069 A | 2/1991 | Ritchart et al. | |
| 5,022,399 A | 6/1991 | Biegeleisen | |
| 5,035,706 A | 7/1991 | Giantureo et al. | |
| 5,059,211 A | 10/1991 | Stack et al. | |
| 5,078,744 A | 1/1992 | Chvapil | |
| 5,085,629 A | 2/1992 | Goldberg et al. | |
| 5,133,731 A | 7/1992 | Butler et al. | |
| 5,152,928 A | 10/1992 | Kudo et al. | |
| 5,188,616 A | 2/1993 | Nadal | |
| 5,192,302 A * | 3/1993 | Kensey et al. | 606/213 |
| 5,197,983 A | 3/1993 | Berman et al. | |
| 5,214,047 A | 5/1993 | Ostersehlt et al. | |
| 5,226,911 A | 7/1993 | Chee et al. | |
| 5,258,042 A | 11/1993 | Mehta | |
| 5,263,984 A | 11/1993 | Li et al. | |
| 5,264,105 A | 11/1993 | Gregg et al. | |
| 5,278,202 A | 1/1994 | Dunn et al. | |
| 5,306,286 A | 4/1994 | Stack et al. | |
| 5,324,519 A | 6/1994 | Dunn et al. | |
| 5,328,471 A | 7/1994 | Slepian | |
| 5,354,295 A | 10/1994 | Guglielmi et al. | |
| 5,364,383 A | 11/1994 | Hayes et al. | |
| 5,370,660 A | 12/1994 | Weinstein et al. | |
| 5,382,259 A | 1/1995 | Phelps et al. | |
| 5,382,261 A | 1/1995 | Palmaz | |
| 5,387,978 A | 2/1995 | Okafuji et al. | |
| 5,409,504 A | 4/1995 | Fritzsche | |
| 5,410,016 A | 4/1995 | Hubbell et al. | |
| 5,413,598 A | 5/1995 | Moreland | |
| 5,425,367 A | 6/1995 | Shapiro et al. | |
| 5,443,458 A | 8/1995 | Eury | |
| 5,456,693 A | 10/1995 | Conston et al. | |
| 5,489,297 A | 2/1996 | Duran | |
| 5,527,337 A | 6/1996 | Stack et al. | |
| 5,531,759 A | 7/1996 | Kensey et al. | |
| 5,545,178 A | 8/1996 | Kensey et al. | |
| 5,549,624 A | 8/1996 | Mirigian et al. | |
| 5,573,934 A | 11/1996 | Hubbell et al. | |
| 5,582,619 A | 12/1996 | Ken | |
| 5,605,902 A | 2/1997 | Amer | |
| 5,609,598 A | 3/1997 | Laufer et al. | |
| 5,626,863 A | 5/1997 | Hubbell et al. | |
| 5,629,077 A | 5/1997 | Turnlund et al. | |
| 5,649,953 A | 7/1997 | Lefebvre | |
| 5,658,308 A | 8/1997 | Snyder | |
| 5,665,831 A | 9/1997 | Neuenschwander et al. | |
| 5,674,287 A | 10/1997 | Slepian et al. | |
| 5,690,671 A | 11/1997 | McGurk et al. | |
| 5,700,258 A | 12/1997 | Mirigian et al. | |
| 5,702,361 A | 12/1997 | Evans et al. | |
| 5,733,950 A | 3/1998 | Dunn et al. | |
| 5,749,915 A | 5/1998 | Slepian | |
| 5,752,974 A | 5/1998 | Rhee et al. | |
| 5,766,710 A | 6/1998 | Turnlund et al. | |
| 5,770,645 A | 6/1998 | Stamler et al. | |
| 5,792,154 A | 8/1998 | Doan et al. | |
| 5,800,543 A | 9/1998 | McLeod et al. | |
| 5,808,518 A | 9/1998 | McKinzie, III et al. | |
| 5,810,847 A | 9/1998 | Laufer et al. | |
| 5,833,705 A | 11/1998 | Ken et al. | |
| 5,843,118 A | 12/1998 | Sepetka et al. | |
| 5,851,508 A | 12/1998 | Greff et al. | |
| 5,858,746 A | 1/1999 | Hubbell et al. | |
| 5,888,546 A | 3/1999 | Ji et al. | |
| 5,894,022 A | 4/1999 | Ji et al. | |
| 5,904,703 A | 5/1999 | Gilson | |
| 5,916,583 A | 6/1999 | Broberg et al. | |
| 5,928,261 A | 7/1999 | Ruiz | |
| 5,935,145 A | 8/1999 | Villar et al. | |
| 5,947,963 A | 9/1999 | Guglielmi | |
| 5,947,977 A | 9/1999 | Slepian et al. | |
| 5,976,162 A | 11/1999 | Doan et al. | |
| 5,990,194 A | 11/1999 | Dunn et al. | |
| 6,001,092 A | 12/1999 | Mirigian et al. | |
| 6,010,498 A | 1/2000 | Guglielmi | |
| 6,045,568 A | 4/2000 | Igaki et al. | |
| 6,080,177 A | 6/2000 | Igaki et al. | |
| 6,083,220 A | 7/2000 | Guglielmi et al. | |
| 6,090,125 A | 7/2000 | Horton | |
| 6,096,052 A * | 8/2000 | Callister et al. | 606/157 |
| 6,096,070 A | 8/2000 | Ragheb et al. | |
| 6,120,534 A | 9/2000 | Ruiz | |
| 6,136,015 A | 10/2000 | Kurz et al. | |
| 6,145,505 A | 11/2000 | Nikolchev et al. | |
| 6,152,928 A | 11/2000 | Wenstrom, Jr. | |
| 6,176,871 B1 | 1/2001 | Pathak et al. | |
| 6,187,027 B1 | 2/2001 | Mariant et al. | |
| 6,214,047 B1 | 4/2001 | Melvin | |
| 6,245,090 B1 | 6/2001 | Gilson et al. | |
| 6,254,103 B1 | 7/2001 | Cooke | |
| 6,254,635 B1 | 7/2001 | Schroeder et al. | |
| 6,258,084 B1 | 7/2001 | Goldman et al. | |
| 6,281,262 B1 | 8/2001 | Shikinami | |
| 6,281,263 B1 | 8/2001 | Evans et al. | |
| 6,306,153 B1 | 10/2001 | Kurz et al. | |
| 6,338,739 B1 | 1/2002 | Datta et al. | |
| 6,358,228 B1 | 3/2002 | Tubman et al. | |
| 6,368,338 B1 | 4/2002 | Konya et al. | |
| 6,379,373 B1 | 4/2002 | Sawhney et al. | |
| 6,387,978 B2 | 5/2002 | Ronan et al. | |
| 6,401,719 B1 | 6/2002 | Farley et al. | |
| 6,409,750 B1 | 6/2002 | Hyodoh et al. | |
| 6,413,272 B1 | 7/2002 | Igaki | |
| 6,432,085 B1 | 8/2002 | Stellon et al. | |
| 6,432,116 B1 | 8/2002 | Callister et al. | |
| 6,436,132 B1 | 8/2002 | Patel et al. | |
| 6,440,164 B1 | 8/2002 | DiMatteo et al. | |
| 6,443,941 B1 | 9/2002 | Slepian et al. | |
| 6,499,486 B1 | 12/2002 | Chervitz et al. | |
| 6,500,204 B1 | 12/2002 | Igaki | |
| 6,527,801 B1 | 3/2003 | Dutta | |
| 6,548,569 B1 | 4/2003 | Williams et al. | |
| 6,555,587 B1 | 4/2003 | Guire et al. | |
| 6,565,521 B1 | 5/2003 | Silberg | |
| 6,565,601 B2 | 5/2003 | Wallace et al. | |
| 6,565,850 B2 | 5/2003 | Blanco | |
| 6,569,190 B2 | 5/2003 | Whalen et al. | |
| 6,574,851 B1 | 6/2003 | Mirizzi | |
| 6,585,754 B2 | 7/2003 | Wallace et al. | |
| 6,592,608 B2 | 7/2003 | Fisher et al. | |
| 6,602,261 B2 | 8/2003 | Greene, Jr. et al. | |
| 6,605,111 B2 | 8/2003 | Bose et al. | |
| 6,626,939 B1 | 9/2003 | Burnside et al. | |
| 6,632,242 B2 | 10/2003 | Igaki | |
| 6,638,293 B1 * | 10/2003 | Makower et al. | 606/200 |
| 6,645,167 B1 | 11/2003 | Whalen, II et al. | |
| 6,660,020 B2 | 12/2003 | Wallace et al. | |
| 6,666,882 B1 | 12/2003 | Bose et al. | |
| 6,676,971 B2 | 1/2004 | Goupil et al. | |
| 6,682,546 B2 | 1/2004 | Amplatz | |
| 6,685,727 B2 | 2/2004 | Fisher et al. | |
| 6,689,126 B1 | 2/2004 | Farley et al. | |
| 6,699,272 B2 | 3/2004 | Slepian et al. | |
| 6,703,041 B2 | 3/2004 | Burns et al. | |

(56) References Cited

U.S. PATENT DOCUMENTS

| | | | |
|---|---|---|---|
| 6,703,047 B2 | 3/2004 | Sawhney et al. | |
| 6,705,323 B1 | 3/2004 | Nikolchev et al. | |
| 6,709,667 B1 | 3/2004 | Lowe et al. | |
| 6,726,682 B2 | 4/2004 | Harrington et al. | |
| 6,726,920 B1 | 4/2004 | Theeuwes et al. | |
| 6,808,518 B2 | 10/2004 | Wellman et al. | |
| 6,818,018 B1 | 11/2004 | Sawhney | |
| 6,846,319 B2 | 1/2005 | Ginn et al. | |
| 6,886,569 B2 | 5/2005 | Chervitz et al. | |
| 6,965,014 B1 | 11/2005 | Delmotte et al. | |
| 7,004,175 B2 | 2/2006 | LaFontaine et al. | |
| 7,070,607 B2 | 7/2006 | Murayama et al. | |
| 7,083,635 B2 | 8/2006 | Ginn | |
| 7,166,570 B2 | 1/2007 | Hunter et al. | |
| 7,192,436 B2 | 3/2007 | Sing et al. | |
| 7,402,320 B2 | 7/2008 | Mirizzi et al. | |
| 2001/0029398 A1 | 10/2001 | Jadhav | |
| 2001/0039450 A1 | 11/2001 | Pavcnik et al. | |
| 2001/0044629 A1 | 11/2001 | Stinson | |
| 2001/0056301 A1 | 12/2001 | Goupil et al. | |
| 2002/0019369 A1 | 2/2002 | Li et al. | |
| 2002/0040239 A1 | 4/2002 | Murayama et al. | |
| 2002/0065546 A1 | 5/2002 | Machan et al. | |
| 2002/0099332 A1 | 7/2002 | Slepian et al. | |
| 2002/0106411 A1 | 8/2002 | Wironen et al. | |
| 2002/0143349 A1 | 10/2002 | Gifford, III et al. | |
| 2002/0143387 A1 | 10/2002 | Soetikno et al. | |
| 2002/0164322 A1 | 11/2002 | Schaufler | |
| 2002/0165582 A1 | 11/2002 | Porter | |
| 2002/0177855 A1 | 11/2002 | Greene, Jr. et al. | |
| 2002/0183830 A1 | 12/2002 | Su et al. | |
| 2002/0188342 A1 | 12/2002 | Rykhus, Jr. et al. | |
| 2002/0188348 A1 | 12/2002 | DiMatteo et al. | |
| 2003/0004533 A1 | 1/2003 | Dieck et al. | |
| 2003/0004568 A1 | 1/2003 | Ken et al. | |
| 2003/0015203 A1 | 1/2003 | Makower et al. | |
| 2003/0028245 A1 | 2/2003 | Barclay et al. | |
| 2003/0040771 A1 | 2/2003 | Hyodoh et al. | |
| 2003/0044766 A1 | 3/2003 | Scholz et al. | |
| 2003/0045924 A1 | 3/2003 | Datta et al. | |
| 2003/0055488 A1 | 3/2003 | Igaki | |
| 2003/0060874 A1 | 3/2003 | Igaki | |
| 2003/0069629 A1 | 4/2003 | Jadhav et al. | |
| 2003/0086975 A1 | 5/2003 | Ringeisen | |
| 2003/0093111 A1 | 5/2003 | Ken et al. | |
| 2003/0104030 A1 | 6/2003 | Igaki et al. | |
| 2003/0109917 A1 | 6/2003 | Rudin et al. | |
| 2003/0144730 A1 | 7/2003 | Datta et al. | |
| 2003/0146532 A1 | 8/2003 | Chen et al. | |
| 2003/0149463 A1 | 8/2003 | Solyman et al. | |
| 2003/0149475 A1 | 8/2003 | Hyodoh et al. | |
| 2003/0229366 A1 | 12/2003 | Reggie et al. | |
| 2004/0010320 A1 | 1/2004 | Huckle et al. | |
| 2004/0013703 A1 | 1/2004 | Ralph et al. | |
| 2004/0015187 A1 | 1/2004 | Lendlein et al. | |
| 2004/0022864 A1 | 2/2004 | Freyman et al. | |
| 2004/0054372 A1 | 3/2004 | Corden et al. | |
| 2004/0059370 A1 | 3/2004 | Greene, Jr. et al. | |
| 2004/0082682 A1 | 4/2004 | Loomis et al. | |
| 2004/0093015 A1 | 5/2004 | Ogle | |
| 2004/0098030 A1 | 5/2004 | Makower et al. | |
| 2004/0186558 A1 | 9/2004 | Pavcnik et al. | |
| 2004/0202694 A1 | 10/2004 | Burbank et al. | |
| 2004/0215231 A1 | 10/2004 | Fortune et al. | |
| 2004/0220611 A1* | 11/2004 | Ogle | 606/200 |
| 2004/0254589 A1* | 12/2004 | Darnis et al. | 606/139 |
| 2005/0065847 A1 | 3/2005 | Feeley et al. | |
| 2005/0070952 A1 | 3/2005 | Devellian | |
| 2005/0085847 A1 | 4/2005 | Galdonik et al. | |
| 2005/0106119 A1 | 5/2005 | Brandom et al. | |
| 2005/0107867 A1* | 5/2005 | Taheri | 623/1.38 |
| 2005/0123581 A1 | 6/2005 | Ringeisen et al. | |
| 2005/0131458 A1 | 6/2005 | Batich et al. | |
| 2005/0163721 A1 | 7/2005 | Harman | |
| 2005/0228436 A1 | 10/2005 | Lorenzo et al. | |
| 2005/0267528 A1 | 12/2005 | Ginn et al. | |
| 2005/0274384 A1 | 12/2005 | Tran et al. | |
| 2005/0277976 A1* | 12/2005 | Galdonik et al. | 606/200 |
| 2005/0283186 A1 | 12/2005 | Berrada et al. | |
| 2006/0009798 A1 | 1/2006 | Callister et al. | |
| 2006/0052822 A1 | 3/2006 | Mirizzi et al. | |
| 2006/0052823 A1 | 3/2006 | Mirizzi et al. | |
| 2006/0058834 A1 | 3/2006 | Do et al. | |
| 2006/0105026 A1 | 5/2006 | Fortune et al. | |
| 2006/0149309 A1 | 7/2006 | Paul et al. | |
| 2006/0167489 A1 | 7/2006 | Satake et al. | |
| 2006/0190076 A1 | 8/2006 | Taheri | |
| 2006/0212055 A1 | 9/2006 | Karabey et al. | |
| 2006/0212127 A1 | 9/2006 | Karabey et al. | |
| 2006/0229668 A1* | 10/2006 | Prestezog et al. | 606/213 |
| 2006/0229669 A1 | 10/2006 | Mirizzi et al. | |
| 2006/0282158 A1 | 12/2006 | Taheri | |
| 2006/0282159 A1 | 12/2006 | Taheri | |
| 2007/0056591 A1 | 3/2007 | McSwain | |
| 2007/0166345 A1* | 7/2007 | Pavcnik et al. | 424/423 |
| 2007/0248640 A1 | 10/2007 | Karabey et al. | |
| 2007/0292472 A1 | 12/2007 | Paul et al. | |
| 2008/0135054 A1 | 6/2008 | Callister et al. | |
| 2009/0216252 A1 | 8/2009 | Melvin et al. | |

FOREIGN PATENT DOCUMENTS

| | | |
|---|---|---|
| EP | 0 882 428 A2 | 12/1998 |
| EP | 0882428 A2 | 12/1998 |
| EP | 1 169 969 A1 | 1/2002 |
| EP | 1169969 A1 | 1/2002 |
| EP | 1 477 132 A2 | 11/2004 |
| WO | WO 94/06460 | 3/1994 |
| WO | WO 00/32112 | 6/2000 |
| WO | WO 01/68720 | 9/2001 |
| WO | WO 03/043506 | 5/2003 |
| WO | WO 03/051409 | 6/2003 |
| WO | WO 2005/053547 A2 | 6/2005 |

OTHER PUBLICATIONS

U.S. Appl. No. 10/754,919, Jan. 10, 2004, Syde A. Taheri.
International Search Report and Written Opinion for International Application No. PCT/US2008/002470, Notification mailed Aug. 28, 2006.
Lord, P., Handbook of Yarn Production, 2003, Woodhead Publishing Ltd. and CRC Press LLC, pp. 12-17, 48-55, 88-115, 368-371.
U.S. Appl. No. 11/339,927, filed Jan. 25, 2006, Karabey et al., 2006/0212055, Office Actions Jan. 5, 2009; Jun. 2, 2008; Sep. 21, 2006.
U.S. Appl. No. 11/340,183, filed Jan. 25, 2006, Mirizzi et al., 2006/0229669, Office Actions Dec. 31, 2008; Oct. 12, 2006.
U.S. Appl. No. 11/339,978, filed Jan. 25, 2006, Karabey et al., 2006/0212127, Office Action Sep. 21, 2006.
U.S. Appl. No. 11/339,975, filed Jan. 25, 2006, Prestezog et al., 2006/0229668, Office Action Oct. 12, 2006.
U.S. Appl. No. 12/340,265, filed Dec. 19, 2008, Karabey et al.
U.S. Appl. No. 11/339,978, filed Jan. 25, 2006, Karabey, et al., 2006/0212127, Office Action Jul. 7, 2009.
U.S. Appl. No. 11/340,183, filed Jan. 25, 2006, Mirizzi, et al., 2006/0229669, Office Action Jun. 17, 2009.
U.S. Appl. No. 11/339,927, filed Jan. 25, 2006, Karabey, et al., 2006/0212055, Office Action Jun. 17, 2009.
Abbott, "Transcervical Sterilization" Best Practice and Research Clinical Obstetrics and Gynecology, 2005, pp. 743-756, vol. 19, No. 5.
About.com:Biology © 2009 About.com, a part of the New York Times Company. Http://biology.about.com/library/organs/heart/blveins.htm.
Abrahams et al., "Biodegradable polyglycolide endocascular coils promote wall thickening and drug delivery in a rat aneurysm model", Neurosurgery (United States) Nov. 2001, 49 (5) p. 1187-93; discussion 1193-5 (Abstract Only).
Bahr et al., "Vascular anastomosis using a biodegradable device with a heat-shrinking sleeve: a preliminary report", Journal of Oral and Maxillofacial surgery—official journal of the American Associateion of Oral and Maxillofacial Surgeons (United States) Dec. 1998, 56 (12) p. 1404-9 (Abstract Only).

(56) References Cited

OTHER PUBLICATIONS

Baler et al., "Photocrosslinked hyaluronic acid hydrogels: natural, biodegradable tissue engineering scaffolds", Biotechnology and bioengineering (United States) Jun. 5, 2003, 82 (5) p. 578-89 (Abstract Only).
Biegeleisen, K., "Use of the venoscope for the treatment of varicose veins", Phlebologie '89, A. Davy, R. Stemmereds, © 1989 John Libbey Eurotext Ltd, pp. 419-422.
Cek D.I. "Sclerosing Agent Therapy for Venous Malformations of the Lip and Perioral Region" Eur J. Plast. Surg. (1992) 15: 276-278.
Guan et al., "Biodegradable poly(ether ester urethane)urea elastomers based on poly(ether ester) triblock copolymers and putrescine: synthesis, characterization and cytocompatibility", Biomaterials (England) Jan. 2004, 25 (1) p. 85-96 (Abstract Only).
He et al., "Assessment of tissue blood flow following small artery welding with an intraluminal dissolvable stent", Microsurgery (United States) 1999, 19 (3) p. 148-52 (Abstract Only).
Hietala et al., "Biodegradation of the copolymeric polylactide stent. Long-term follow-up in a rabbit aorta model", Journal of vascular research (Switzerland) Jul.-Aug. 2001, 38 (4) p. 361-9 (Abstract Only).
Hoerstrup et al., "Tissue engineering of small caliber vascular grafts", European Association for Cardio-thoracic Surgery (England) Jul. 2001, 20 (1) p. 164-9 (Abstract Only).
Hoffman et al., "Biodegradable synthetic polymer scaffolds for reinforcement of albumin protein solders used for laser-assisted tissue repair", Biomedical sciences instrumentation (United States) 2002, 38 p. 53-8 (Abstract).
International Search Report for corresponding PCT Application No. PCT/US2005/030370 Mailed May 9, 2006.
International Written Opinion for corresponding PCT Application No. PCT/US2005/030370 Mailed May 9, 2006.
Izhar et al., "Novel synthetic selectively degradable vascular prostheses: a preliminary implantation study", Journal of surgical research (United States) Feb. 2001, 95 (2) p. 152-60 (Abstract Only).
Joji et al., "Experimental study of mechanical microvascular anastomosis with new biodegradable ring device", British journal of plastic surgery (England) Oct. 1000, 52 (7) p. 559-64 (Abstract Only).
Kimura et al., "Evaluation of an absorbable rig for vascular anastomosis", Journal of reconstructive microsurgery (United States) Jul. 1999, 15 (5) p. 331-6 (Abstract Only).
Lee et al., "Elastic biodegradable poly(glycolide-co-caprolactone) scaffold for tissue engineering", Journal of biomedical materials research (United States) Jul. 1, 2003, 66 A (1) p. 29-37 (Abstract Only).
McNally-Heintzelman et al., "Scaffold-enhanced albumin and n-butyl-cyanoacrylate adhesives for tissue repair: ex vivo evaluation in a porcine model", Biomedical sciences instrumentation (United States) 2003, 39 p. 312-7.
Murayama et al., "Bioabsorbable polymeric material coils for embolization of intracranial aneurysms: a preliminary experimental study", Journal of neurosurgery (United States) Mar. 2001, 94 (3) p. 454-63 (Abstract Only).
Murayama et al., "Cellular responses of bioabsorbable polymeric material and Guglielmi detachable coil in experimental aneurysms", Stroke; a journal of cerebral circulation (United States) Apr. 2002, 33 (4) p. 1120-8 (Abstract Only).

Office Action in Chinese Patent Application No. 200680009499.6 dated Feb. 24, 2010.
Office Action in Chinese Patent Application No. 200680009499.6 dated Nov. 29, 2010.
Office Action in European Patent Application No. 06719366.4 dated Nov. 5, 2010.
Proceedings in corresponding PCT application No. (PCT/US2004/038274): International Preliminary Report on Patentability, International Search Report, Claims.
Qu et al., "An absorbably pinned-ring device for microvascular anastomosis of vein grafts: experimental studies", Microsurgery (United States) 1999, 19 (3) p. 128-34 (Abstract Only).
Shi et al., "Towards tissue engineering of a composite aortic valve", Viomedical sciences instrumentation (United States) 2002, 38 p. 35-40 (Abstract Only).
Su et al., "Expandable bioresorbable endovascular stent. I. Fabrication and Properties", Annals of biomedical engineering (United States) Jun. 2003, 31 (6) p. 667-77 (Abstract Only).
U.S. Appl. No. 10/754,919, filed Jan. 10, 2004, Syde A. Taheri, 2005-0107867, Office Actions Aug. 26, 2008.
U.S. Appl. No. 11/339,975, filed Jan. 25, 2006, Anna Prestezog, 2006-0229668, Notice of Allowance Mar. 30, 2011.
U.S. Appl. No. 11/339,978, filed Jan. 25, 2006, Halil I. Karabey, 2006-0212127, Office Actions May 24, 2011.
U.S. Appl. No. 11/340,183, filed Jan. 25, 2006, Michael S. Mirizzi, 2006-0229669, Notice of Allowance Mar. 9, 2010.
U.S. Appl. No. 11/407,482, filed Apr. 20, 2006, Syde A. Taheri, 2006-0190076, Office Actions Feb. 2, 2011.
U.S. Appl. No. 11/407,689, filed Apr. 20, 2006, Syde A. Taheri, 2006-0282158, Office Actions Mar. 3, 2011.
U.S. Appl. No. 11/407,847, filed Apr. 20, 2006, Syde A. Taheri, 2006-0282159, Office Actions Jan. 31, 2011.
U.S. Appl. No. 12/340,365, filed Dec. 19, 2008, Halil I. Karabey, 2009-0159088, Office Actions Jan. 5, 2011, Notice of Allowance May 18, 2011.
U.S. Appl. No. 11/339,978, filed Jan. 25, 2006, Halil I. Karabey, 2006-0212127, Office Action Aug. 30, 2011.
U.S. Appl. No. 12/906,961, filed Oct. 18, 2018, Michael S. Mirizzi, 2011/0172695, Office Action Jan. 4, 2012.
U.S. Appl. No. 12/906,961, filed Oct. 18, 2010, Michael S. Mirizzi, 2011/0172695, Notice of Allowance Aug. 16, 2012.
U.S. Appl. No. 13/175,732, filed Jul. 1, 2011, Halil I. Karabey, 2011/0259353, Notice of Allowance Aug. 28, 2012.
U.S. Appl. No. 11/339,978, filed Jan. 25, 2006, Karabey et al., 2006-0212127, Office Action Jul. 19, 2010.
U.S. Appl. No. 11/339,975, filed Jan. 25, 2006, Prestezog et al., 2006-0229668, filed Apr. 16, 2010.
U.S. Appl. No. 11/339,927, filed Jan. 25, 2006, Karabey et al., 2006-0212055, Office Action Apr. 2, 2010.
U.S. Appl. No. 11/407,482, filed Apr. 20, 2006, Taheri, 2006-0190076, Office Actions Aug. 4, 2010.
U.S. Appl. No. 11/407,847, filed Apr. 20, 2006, Taheri, 2006-0282159, Office Action Aug. 6, 2010.
U.S. Appl. No. 11/407,689, filed Apr. 20, 2006, Taheri, 2006-0282158, Office Action Aug. 23, 2010.
U.S. Appl. No. 11/339,978, filed Jan. 25, 2006, Halil I. Karabey, 2006-0212127, Office Action Mar. 29, 2012.

\* cited by examiner

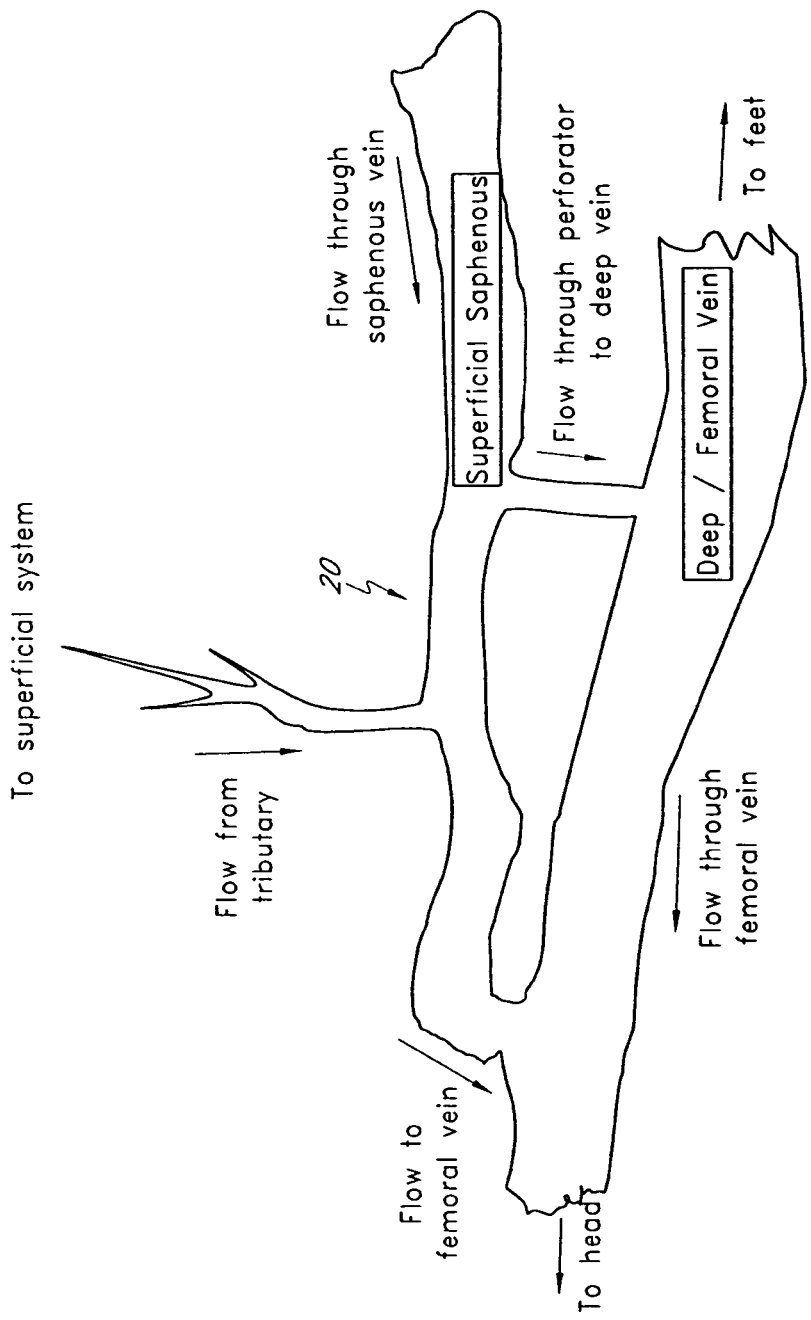

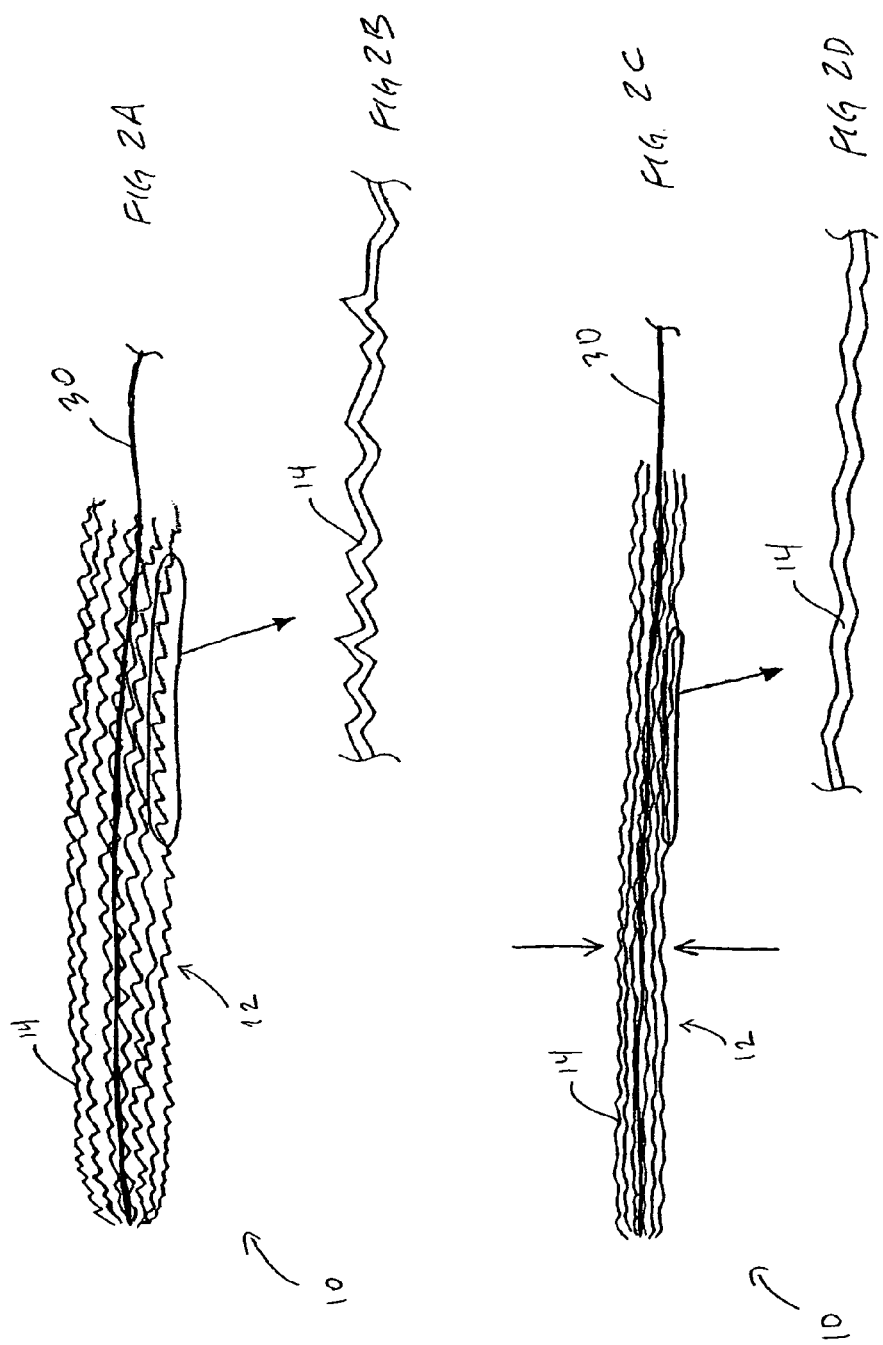

302  386

302  386

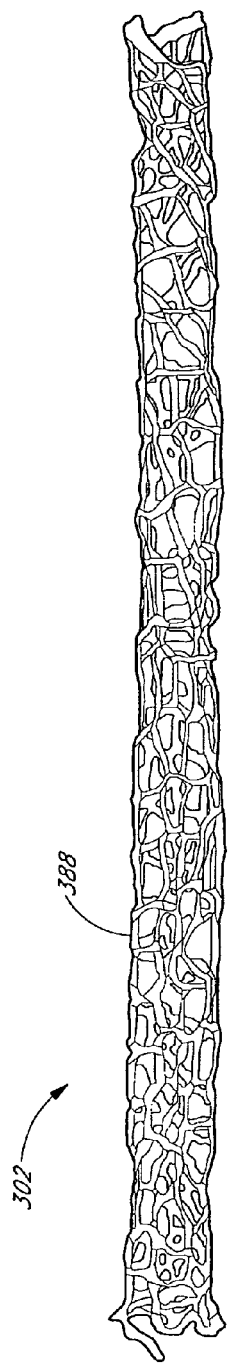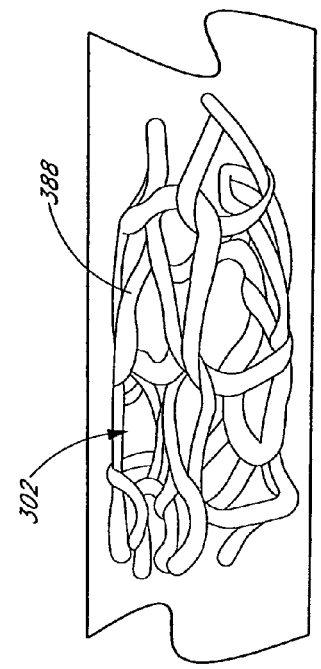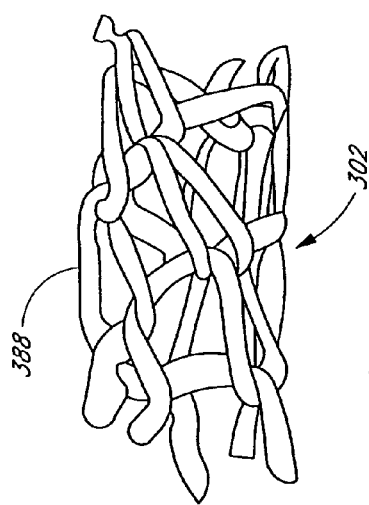
FIG. 45A
FIG. 45C
FIG. 45B

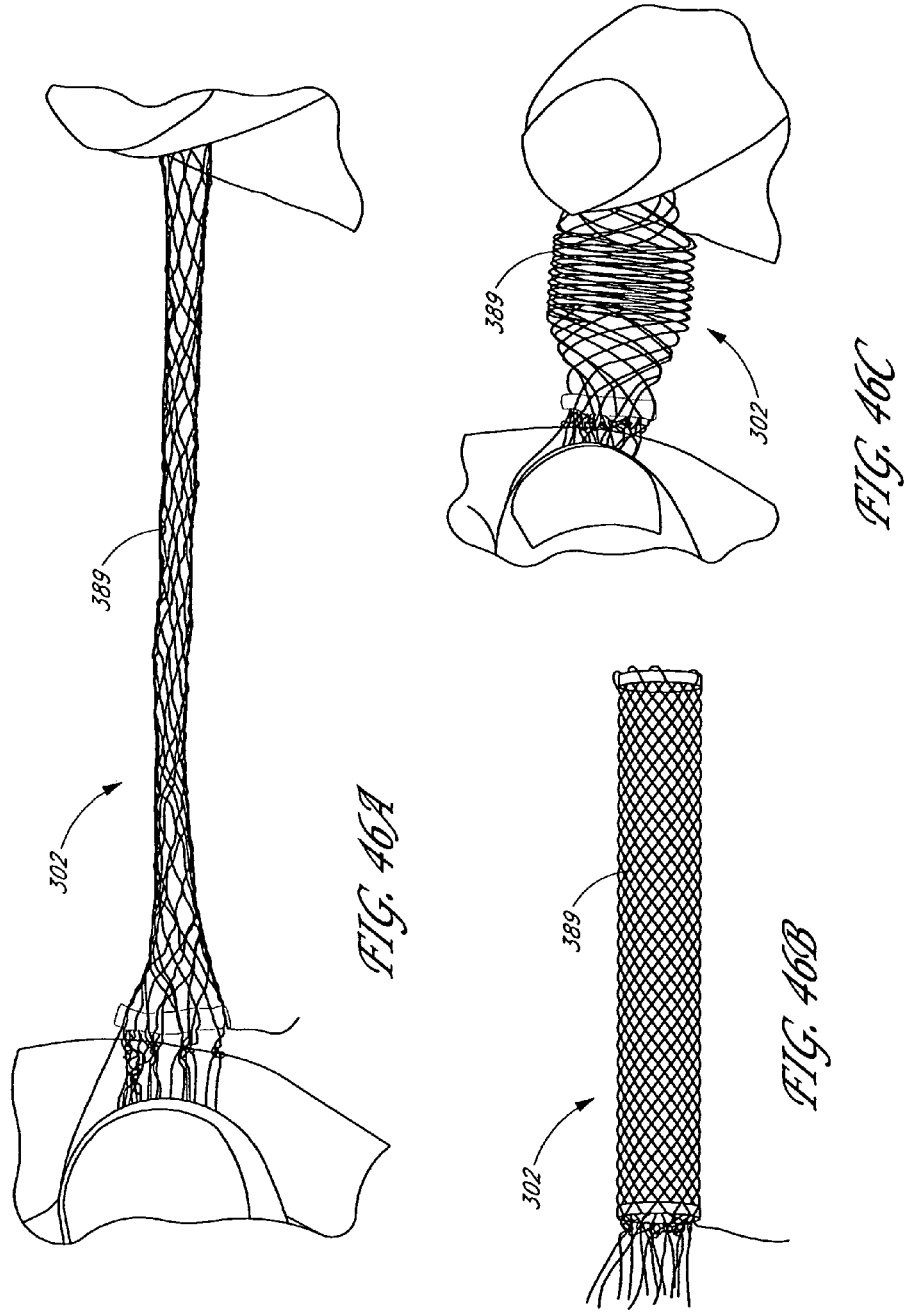

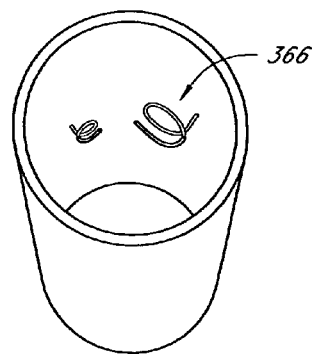
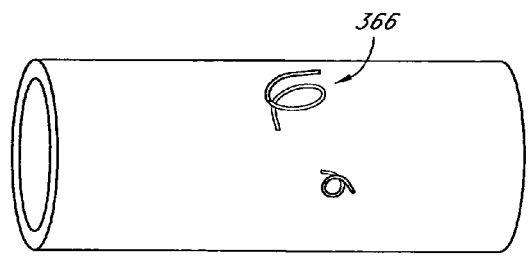
FIG. 51A          FIG. 51B
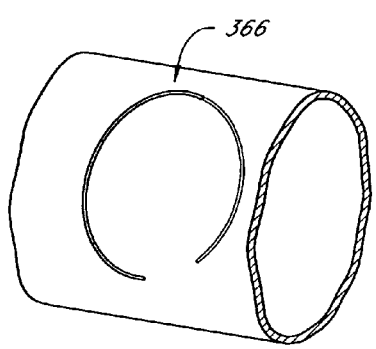
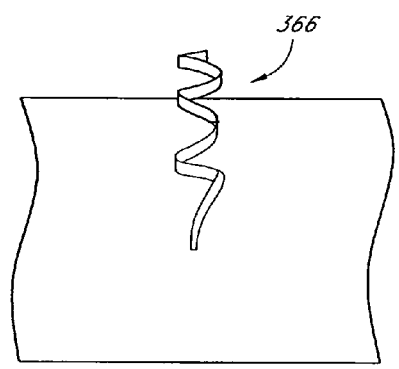
FIG. 51C          FIG. 51D
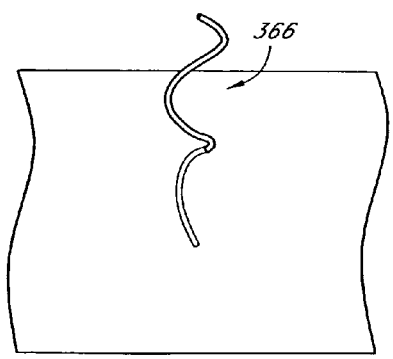
FIG. 51E

OCCLUSIVE IMPLANT AND METHODS FOR HOLLOW ANATOMICAL STRUCTURE

BACKGROUND

1. Field

Certain embodiments disclosed herein relate to occlusion of a hollow anatomical structure by inserting an occluding device or occluding material into a hollow anatomical structure or surrounding native tissue.

2. Description of the Related Art

The preferred embodiments relate generally to a method and material composition for introduction into a hollow anatomical structure (HAS) with particular relevance to the venous system in the lower extremities. The term "hollow anatomical structure" is a broad term and is used in its ordinary sense, including, without limitation, veins, arteries, gastric structures, coronary structures, pulmonary structures, tubular structures associated with reproductive organs, and the like. Hollow anatomical structures particularly suited to occlusion by the methods of preferred embodiments include veins, preferably veins of the lower extremities, especially veins in the leg.

The human venous system of the lower extremities consists essentially of the superficial venous system and the deep venous system with perforating veins connecting the two systems. The superficial system includes the long or great saphenous vein and the small saphenous vein. The deep venous system includes the anterior and posterior tibial veins which unite to form the popliteal vein, which in turn becomes the femoral vein when joined by the short saphenous vein.

The venous system contains numerous one-way valves for directing blood flow back to the heart. Venous valves are usually bicuspid valves, with each cusp forming a sack or reservoir for blood. Retrograde blood flow forces the free surfaces of the cusps together to prevent continued retrograde flow of the blood and allows only antegrade blood flow to the heart. When an incompetent valve is in the flow path, the valve is unable to close because the cusps do not form a proper seal and retrograde flow of the blood cannot be stopped. When a venous valve fails, increased strain and pressure occur within the lower venous sections and overlying tissues, sometimes leading to additional, distal valvular failure. Two venous conditions or symptoms which often result from valve failure are varicose veins and more symptomatic chronic venous insufficiency.

The resulting condition is progressive and includes: dilation and tortuosity of the superficial veins of the lower limbs, unsightly discoloration, pain, swelling, and possibly ulceration. This failure can also worsen deep venous reflux and perforator reflux. Current treatments of venous insufficiency include surgical procedures such as vein stripping, ligation, and occasionally, vein-segment transplant.

Vein stripping and vein-segment transplant are less-favored treatment options. Vein stripping typically consists of tying off, or ligating, and removal of the saphenous vein. The ligation involves making an incision in the groin and using sutures outside the vein to tie it shut. When the veins are tied off and/or removed, blood flows through the deep veins and back to the heart. This surgery is generally done under general or regional anesthesia during a hospital stay or on an outpatient basis, depending upon the extent of the procedure. Vein stripping is generally painful and requires a long recovery time. This procedure is less favored and outcomes can be poor. Procedures combining ligation and stripping are sometimes performed, but studies have shown they offer little advantage over stripping alone. Vein segment transplant has been employed in certain organ transplant procedures. However it is not generally employed in the superficial venous system in humans.

Ligation by ablation involves the cauterization or coagulation of vascular lumina using thermal energy applied through a delivery catheter, e.g., electrical energy applied through an electrode device (e.g., a radio frequency or RF device), energy delivered by regular and high-frequency ultrasound, or laser energy. An energy delivery device is typically introduced into the vein lumen and positioned so that it contacts the vein wall. Once properly positioned, the RF, laser, ultrasound, or other energy is applied to the energy delivery device, thereby causing the vein wall to shrink in cross-sectional diameter. A reduction in cross-sectional diameter, for example, from 5 mm (0.2 in) to 1 mm (0.04 in), significantly reduces the flow of blood through the vein and results in an effective ligation. Through not required for effective ligation, the vein wall can completely collapse, thereby resulting in a full-lumen obstruction that blocks the flow of blood through the vein.

SUMMARY OF THE INVENTION

The preferred embodiments provide materials, structures and methods which can be employed to occlude a hollow anatomical structure. Preferably, a bioresorbable material is employed to occlude the hollow anatomical structure. Alternatively, a bioabsorbable, bioerodable, biodegradable, or dissolvable material is employed. In certain embodiments, a biocompatible material that is not bioresorbable, bioabsorbable, bioerodable, biodegradable, or dissolvable is employed. The bioresorbable material is preferably placed in the hollow anatomical structure by a minimally invasive method which can be employed for precisely locating the material within the target lumen.

According to one embodiment, a method of treating a hollow anatomical structure comprises inserting into the hollow anatomical structure an implant comprising a plurality of bulked fibers. The fibers are formed from one or more bioabsorbable materials. The method further comprising causing, with the implant, a partial occlusion of the hollow anatomical structure. The method further comprises causing, with the implant, causing a subsequent, substantially complete occlusion of the hollow anatomical structure.

According to one embodiment, a method of reducing the patency of a blood vessel comprises inserting into the blood vessel an scaffold comprising a plurality of tortuous fibers. The fibers are formed from one or more bioabsorbable materials. The method further comprises causing, with the scaffold, a partial occlusion of the blood vessel. The method further comprises causing, with the scaffold, a subsequent, substantially complete occlusion of the blood vessel.

According to one embodiment, a method of inhibiting migration of a bioabsorbable fibrous scaffold inserted within a hollow anatomical structure comprises permitting biological fluid flow through the scaffold; and gradually causing a substantially complete blockage of biological fluid flow through the scaffold.

According to one embodiment, a method of reducing blood flow through a blood vessel comprises providing an implant comprising a plurality of loose bioabsorbable fibers that extend generally longitudinally and form a number of bends along the length thereof; inserting the implant into the blood vessel; spanning a cross-section of the blood vessel with the bioabsorbable fibers; permitting blood flow between the fibers and past the implant; and subsequently substantially blocking blood flow between the fibers.

According to one embodiment, a method of treating a hollow anatomical structure comprises inserting into the hollow anatomical structure an implant comprising a plurality of crimped fibers. The fibers are formed from one or more bioabsorbable materials. The method further comprises causing, with the implant, a partial occlusion of the hollow anatomical structure; and causing, with the implant, a subsequent, substantially complete occlusion of the hollow anatomical structure.

According to one embodiment, a method of treating a hollow anatomical structure comprises inserting into the hollow anatomical structure an implant comprising a plurality of textured fibers. The fibers formed are from one or more bioabsorbable materials. The method further comprises providing one or more fluid flow paths through the inserted implant; and gradually causing blockage of substantially all of the flow paths.

According to one embodiment, a method of treating a hollow anatomical structure comprises inserting into the hollow anatomical structure an implant comprising a plurality of bulked fiber. The fibers are formed from one or more bioabsorbable materials. The method further comprises causing, with the implant, causing a partial occlusion of the hollow anatomical structure; and causing, with the implant, a subsequent, more complete occlusion of the hollow anatomical structure.

According to one embodiment, an apparatus for treating a hollow anatomical structure comprises an implant sized for insertion into the hollow anatomical structure. The implant comprises a plurality of crimped fibers. The fibers are formed from one or more bioabsorbable materials. The implant extends generally longitudinally from a first end thereof to a second end. The implant forms one or more fluid flow paths between the fibers, and the one or more flow paths extend from the first end to the second end.

According to one embodiment, an implant comprises bioresorbable materials or compounds and is introduced into a hollow anatomical structure for occlusion. The materials preferably are non-in-situ forming materials. In some embodiments the implant can expand on its own. In other embodiments the implant can be actuated into an expanded condition. The implant preferably does not take on a uniform, e.g., predefined, shape. The implant is deliverable via surgical procedure or catheter. The materials of the implant preferably are not solvent based or immediately soluble by fluids in the body. According to one embodiment, the occlusion is intended to occur over time as the native fluid (e.g., blood) is limited by the expanding implant such that native fluid becomes stopped or frustrated and the body's natural healing takes over to occlude the hollow anatomical structure. Active agents including but not limited to sclerosants, inflammatory agents, cytokines, growth factors, clotting factors, tissue attachment factors, platelet activators, and antibacterial agents can be added to the implant with a focus to elicit and/or favorably alter the body's response and/or coagulation cascade for healing/occluding the hollow anatomical structure.

According to one embodiment, a fixed length or scrunchable length implant can be provided for occlusion. A fibrous mass structure can comprise fiber filaments. In one embodiment, the fibrous mass structure can include fibers and/or other components formed from polylactides (polylactic acid) and/or polyglycolides (polyglycolic acid). As described further below, Polyglycolide (PGA) and Polylactide (PLA) are synthetic absorbable polymers. These polymers can be prepared from their cyclic diesters lactide and/or glycolide by ring opening polymerization to synthesize higher molecular weight polymers or by direct polycondensation of lactic acid and/or glycolic acid to synthesize low molecular weight polymers. In one embodiment the fibrous mass structure comprises PGA and PLA filaments. The filament compositions can be homogeneous in some embodiments. In some embodiments, one or more distinctively unique filament compositions can be used. In some embodiments, filaments can have compositions unique to the distal and/or proximal ends. In some embodiments, the filament composition itself can be a copolymer of PLA and PGA. Deployment of the implant can comprise scrunching the implant, e.g., contracting the implant along a longitudinal axis to radially expand the implant and/or increase fiber density in a given cross section. The scrunching can be performed using a sleeve, a push rod, a pull string, a pull wire, a push and pull tube, using only external manual compression, and/or combinations thereof. The implant can be locked in a deployed configuration (although this is not required) by a one way stop, a knot, an adhesive, heating the implant, a cutter, a gelling material, and/or combinations thereof. Occlusion is preferably achieved by blocking blood flow completely (e.g. stopping or preventing), by limiting the flow of native fluid (e.g. frustrating or inhibiting), by acting as a structure/scaffold for the natural body healing process leading to occlusion, and/or by addition of sclerosants or other foreign body response proliferative agents or drugs and/or combinations thereof.

In another embodiment, a sock can be formed weaved, knitted, and/or braided from any suitable bioresorbable material. In another embodiment, a rigid implant, e.g., a bioresorbable plug, can be coupled with bioresorbable filament materials for occlusion of a hollow anatomical structure. The rigid implant preferably has a generally fixed length and shape to partially or entirely block flow acutely in the hollow anatomical structure.

While the methods and materials of preferred embodiments are particularly preferred for use in occluding veins of the lower extremities, they can be employed in occluding other hollow anatomical structures, including, but not limited to: varicoceles associated with internal spermatic vein reflux, pelvic congestion associated with ovarian vein reflux, abdominal varices, superficial and perforator veins, hemorrhoids, esophageal varices, fallopian tubes, vas deferens, cardiovascular deformations, vessels in the brain, lumbar arteries, feeding vessels into the aorta to prevent abdominal aortic aneurysm (AAA) graft endoleaks, vessel occlusion for arterio-venous fistula/malformations, cerebral or peripheral vascular aneurysms, aneurismal vessel occlusions. Additionally, these embodiments can also be employed in occluding other hollow anatomical structures not necessarily from inside the lumina, but acting extra-structurally for example as bulking agents outside the lower esophageal sphincter as in the treatment of gastroesophageal reflux disease (GERD), for extravascular bulking of incompetent venous valves to improve valvular coaptation and function in the treatment of varicose veins and chronic venous insufficiency, or for bulking the area around the coronary valves for improved valvular coaptation and function. As well, these embodiments can be employed not necessarily to occlude hollow anatomical structures, but instead for bulking, tissue hardening, and tissue strengthening for example in modifying the uvula in the treatment of sleep apnea, for bulking the cardiac muscle in treatment of congestive heart failure, or for closing the tissue path created by percutaneous vessel access in catheterization procedures.

According to one embodiment, an apparatus for treating a hollow anatomical structure comprises an implant sized for insertion into the hollow anatomical structure. The implant comprises a plurality of loose, bulked fibers. The fibers are formed from one or more bioabsorbable materials.

According to some variations, the fibers can be radially bulked, randomly arranged, non-knit, and/or non-woven. According to some variations, the fibers can be formed from an alpha-hydroxy acid, and/or formed from material selected from the group consisting of polyglycolic acid, polyglycolic-co-lactic acid, polylactic-glycolic acid, polyglycolide-co-lactide, and polyglycolide. According to some variations, the fibers can be from 0.1 denier to 10 denier. The implant can comprise between 500 and 100,000 fibers, in some embodiments. The fibers can be joined at a first end portion of the implant. The fibers can be joined at a second end portion of the implant.

According to some variations, the apparatus comprises a fixation element configured to limit migration of the implant when in the hollow anatomical structure. According to some variations, the apparatus further comprises a tether coupled with the implant the tether can be configured to extend beyond at least one end portion of the implant. The tether extends within the implant in some embodiments. The tether can be formed from a bioabsorbable material having a first bioabsorption rate. The fibers can be formed from a bioabsorbable material having a second bioabsorption rate. The first bioabsorption rate can be different from the second bioabsorption rate. In some embodiments, the first bioabsorption rate is lower than the second bioabsorption rate. In other embodiments, the first bioabsorption rate is higher than the second bioabsorption rate. The fibers can have a bioabsorption time of 2-24 weeks after implantation.

According to some variations, the apparatus additionally comprises an implant locking mechanism. In some embodiments, the apparatus comprises a pull string coupled with the implant. The pull string can be configured to extend beyond at least one end portion of the implant. The pull string can extend within the implant. In some embodiments, the implant locking mechanism comprises a funnel coupled with the implant. The pull string can be knotted in some embodiments. The pull string can comprise a plurality of bumps along at least a portion thereof.

According to some variations, the implant further comprises a radially expandable element. The fibers can be positioned generally interior to the expandable element when implanted in the hollow anatomical structure. The fibers can be positioned generally exterior to the expandable element when implanted in the hollow anatomical structure. The expandable element can extend generally the full length of the implant. The expandable element can be positioned generally at an end portion of the implant. In some embodiments, the apparatus comprises a expandable element configured to anchor the implant when inserted within the hollow anatomical structure.

According to some variations, the implant additionally comprises a drug. The implant can comprises a sclerosant in some embodiments. According to some variations, the implant has a first density associated with an unstressed state of the implant, and a higher second density associated with a radially compressed state of the implant. According to some variations, the fibers comprise first fibers having a first bioabsorption rate and second fibers having a second bioabsorption rate, wherein the first bioabsorption rate differs from the second bioabsorption rate.

According to another embodiment, an apparatus for treating a hollow anatomical structure comprises a scaffold configured for implantation in the hollow anatomical structure. At least a section of the scaffold comprises a plurality of loose fibers that extend generally longitudinally and form a number of bends along the length thereof. The fibers are formed from one or more bioabsorbable materials. According to some variations, the fibers are randomly arranged in the scaffold. In some embodiments, at least one of the fibers comprises a number of the bends which are spaced apart along the fiber by one or more distances which are significantly smaller than the length of the fiber. According to some variations, the section of the scaffold is non-knit and/or non-woven. An outer surface of the scaffold can be abrasive. The fibers can comprise first fibers having a first bioabsorption rate and second fibers having a second bioabsorption rate, and the first bioabsorption rate can differ from the second bioabsorption rate. The fibers can have a bioabsorption time of 2-24 weeks after implantation.

According to another embodiment, a scaffold for treating a hollow anatomical structure comprises a plurality of tortuous, non-knit fibers, the fibers being formed from one or more bioabsorbable materials. According to some variations, the fibers are randomly arranged. The fibers can be loosely arranged in the scaffold. At least a portion of the scaffold can be non-knit and non-woven. The fibers can comprise first fibers having a first bioabsorption rate and second fibers having a second bioabsorption rate, and the first bioabsorption rate can differ from the second bioabsorption rate. The fibers can have a bioabsorption time of 2-24 weeks after implantation.

According to another embodiment, an apparatus for treating a hollow anatomical structure comprises an implant configured for implantation in the hollow anatomical structure. The implant comprises a pile of tortuous, bioresorbable fibers. According to some variations, the fibers are randomly arranged. The fibers can be loosely arranged in the implant. At least a portion of the implant can be abrasive.

According to another embodiment, an apparatus for treating a hollow anatomical structure comprises an implant of suitable width for placement in the hollow anatomical structure. The implant comprises a plurality of textured fibers. The fibers are formed from one or more bioabsorbable materials. According to some variations, the fibers are randomly arranged. The fibers can be loosely arranged in the implant. At least a portion of the implant can be non-knit. At least a portion of the implant can be non-woven.

According to another embodiment, an apparatus for treating a hollow anatomical structure comprises an implant sized for insertion into the hollow anatomical structure. The implant comprises a plurality of crimped fibers. The fibers are formed from one or more bioabsorbable materials. According to some variations, the fibers are loosely arranged in the implant. The fibers are non-knit in some embodiments. The fibers are non-woven in some embodiments.

According to another embodiment, an apparatus for treating a hollow anatomical structure comprises an implant sized for insertion into the hollow anatomical structure. The implant comprises a plurality of undulating fibers. The fibers are formed from one or more bioabsorbable materials. According to some variations, the fibers are loosely arranged in the implant. The fibers can be non-knit. The fibers can be non-woven. At least a portion of an outer surface of the implant can be abrasive. The fibers can comprise first fibers having a first bioabsorption rate and second fibers having a second bioabsorption rate, the first bioabsorption rate can differ from the second bioabsorption rate. The fibers can have a bioabsorption time of 2-24 weeks after implantation.

According to another embodiment, an apparatus for treating a hollow anatomical structure comprises a scaffold configured for placement in the hollow anatomical structure. The scaffold comprises a plurality of expandable fibers. The fibers are formed from one or more biodegradable materials. According to some variations, the fibers are individually expandable. The fibers can be loosely arranged in the implant. At least a section of the scaffold can be non-knit in some embodiments. At least a section of the scaffold can be non-woven in some embodiments.

According to another embodiment, an apparatus for treating a hollow anatomical structure comprises an implant comprising a plurality of bioabsorbable fibers. The implant has a compressed state in which the implant can fit within a cylindrical tube having an inside diameter of 8 French or less. The implant is expandable from the compressed state to an expanded state in which the implant has sufficient size to span the inside diameter of a cylindrical tube having an inside diameter of 24 French or greater. According to some variations, the implant has sufficient size, when in the expanded state, to span the inside diameter of a cylindrical tube having an inside diameter of 24-36 French. In some embodiments, the implant has sufficient size, when in the expanded state, to span the inside diameter of a cylindrical tube having an inside diameter of 12-60 French. The implant can fit within a cylindrical tube having an inside diameter of 6-8 French when in the compressed state in some embodiments. The implant can comprise a plurality of undulating fibers. At least a section of the implant can be non-knit. At least a section of the implant can be non-woven. The implant can comprise a fixation element configured to limit migration of the implant when in the hollow anatomical structure. The implant can be expandable such that the implant tends toward the expanded state in the absence of external forces.

According to another embodiment, an apparatus for treating a hollow anatomical structure comprises an implant comprising a plurality of bioabsorbable fibers. The implant has a compressed state in which the implant can pass through a cylindrical tube having an inside diameter of 8 French or less. The implant is expandable from the compressed state to a treatment state in which the implant has a transverse size which is sufficiently large to occupy an adult human greater saphenous vein of average size. According to some variations, the implant can pass through a cylindrical tube having an inside diameter of 6-8 French when in the compressed state. The implant can comprise a plurality of undulating fibers. At least a section of the implant can be non-knit. At least a section of the implant can be non-woven. The implant can comprise a fixation element configured to limit migration of the implant when in the hollow anatomical structure. The implant can be expandable such that the implant tends toward the expanded state in the absence of external forces.

According to another embodiment, a method of treating a hollow anatomical structure having a diameter of 4 mm or more comprises inserting into the hollow anatomical structure a catheter having a size of 8 French or less. A bioabsorbable fibrous implant is passed through the catheter and into the hollow anatomical structure. With the implant, the patency of the hollow anatomical structure is reduced. According to some variations, the method further comprises occluding the hollow anatomical structure with the implant. The implant can be expanded to a treatment state within the hollow anatomical structure in some methods. The method can included promoting occlusive ingrowth with the implant when the implant is in the hollow anatomical structure. The hollow anatomical structure can comprise a vein. In some embodiments, the hollow anatomical structure comprises a greater saphenous vein. Inserting the catheter can comprise inserting the catheter at an insertion site spaced from the sapheno-femoral junction, and further comprise advancing the implant from the insertion site to the sapheno-femoral junction. The hollow anatomical structure can have a diameter of 4-12 mm in some embodiments. In some embodiments, the hollow anatomical structure can have a diameter of 4-20 mm.

According to another embodiment, a method of treating a vein comprises accessing the vein at an access point spaced from a sapheno-femoral junction. A bioabsorbable fibrous body is implanted into the vein through the access point. The body is moved in the vein toward the sapheno-femoral junction. According to some variations, the method additionally comprises securing the body in the hollow anatomical structure to limit migration of the body within the vein. A sheath can be inserted through the access point and the body can be pushed with a pushrod through the sheath into the vein in some methods. A heat treatment can be performed on the vein, the heat treatment can comprise one or more of delivering radio frequency energy, delivering heat energy from a resistive element, and delivering energy from a laser. The method can additionally comprise moving an end of the body in the vein to the sapheno-femoral junction.

According to another embodiment, a method of treating a hollow anatomical structure comprises delivering into the hollow anatomical structure an implant comprising a plurality of loose tortuous fibers. The fibers are formed from one or more bioabsorbable materials. According to some variations, the method additionally comprises securing the implant in the hollow anatomical structure to limit migration of the implant within the hollow anatomical structure.

According to another embodiment, a kit for treating a hollow anatomical structure comprises a bioabsorbable fibrous implant sized for insertion into the hollow anatomical structure. A sheath is sized for insertion into the hollow anatomical structure. The sheath has an outer diameter and an inner diameter. The inner diameter is configured to receive the implant for delivery of the implant into the hollow anatomical structure. A pushrod is sized for insertion into the sheath and configured to advance the implant through the sheath for delivery of the implant into the hollow anatomical structure. According to some variations, the sheath comprises an abrasive element on the outer diameter. The abrasive element can be configured to engage a surface of the hollow anatomical structure when the sheath is inserted within the hollow anatomical structure. The kit can additionally comprise an implant locking mechanism. The implant locking mechanism can comprise a pull string configured to be coupled with the implant. The implant locking mechanism can comprises a funnel coupled with the implant. The pull string can be knotted. The pull string can comprise a plurality of bumps along at least a portion thereof.

According to another embodiment, a system for treating a hollow anatomical structure comprises a bioabsorbable fibrous implant sized for insertion into the hollow anatomical structure. A continuous feed mechanism is configured to deliver the implant into the hollow anatomical structure.

According to another embodiment, a method of treating a hollow anatomical structure of a patient comprises implanting a bioabsorbable fibrous body in the hollow anatomical structure. The body is secured in the hollow anatomical structure to limit migration of the body within the hollow anatomical structure. According to some variations, securing the body comprises anchoring the body at an access site of the hollow anatomical structure. In some embodiments, the method further comprises positioning the body so that a portion of the body extends out of the hollow anatomical structure through the skin of the patient at an access site on the skin. The body can further comprise a tether, and the method can further comprise trimming an end portion of the body so that it is substantially flush with the skin and so that the tether extends beyond the body through the access site. The tether can be secured near the access site. Securing the body can comprise implanting an expandable anchor near the body in the hollow anatomical structure. Securing the body can comprise thermally shrinking the hollow anatomical structure near an implant location in the hollow anatomical structure, and implanting the body can comprise implanting the body at the implant location. Securing the body can comprise securing the body with a fenestration anchor. Securing the body can comprise anchoring the body at a percutaneous retrograde access site.

According to another embodiment, an apparatus for treating a hollow anatomical structure comprises a bioabsorbable fibrous body. A fixation member is associated with the body and configured to limit migration of the body when implanted in the hollow anatomical structure. According to some variations, the fixation member comprises a tether. The fixation member can comprise an anchor. The fixation member can comprise an expandable element. The fixation member can comprise a braid. The fixation member can be bioabsorbable. The fixation member can have a first bioabsorption rate, the body can have a second bioabsorption rate, and the first bioabsorption rate can be different from the second bioabsorption rate. The first bioabsorption rate can be lower than the second bioabsorption rate. The first bioabsorption rate can be higher than the second bioabsorption rate.

BRIEF DESCRIPTION OF THE DRAWINGS

FIG. 1 depicts a portion of the saphenous and femoral venous systems.

FIG. 2A depicts one embodiment of an implant comprising a fibrous mass structure for occlusion of a hollow anatomical structure, such as a vein, the fibrous mass structure is shown in a generally unstressed, expanded configuration.

FIG. 2B depicts a fiber of the implant of FIG. 2A showing bends in the fiber in the generally unstressed, expanded configuration.

FIG. 2C depicts the fibrous mass structure implant of FIG. 2A in a generally low-profile, compressed configuration.

FIG. 2D depicts a fiber of the implant of FIG. 2C showing bends in the fiber in the generally low-profile, compressed configuration.

FIGS. 45A-C illustrate an expandable stent fixation element according to one embodiment.

FIGS. 46A-C illustrate an expandable braided stent fixation element according to one embodiment.

FIGS. 51A-H illustrate several coils configured for use in a fenestration fixation technique according to several embodiments.

DETAILED DESCRIPTION OF THE PREFERRED EMBODIMENTS

Figure 2E:
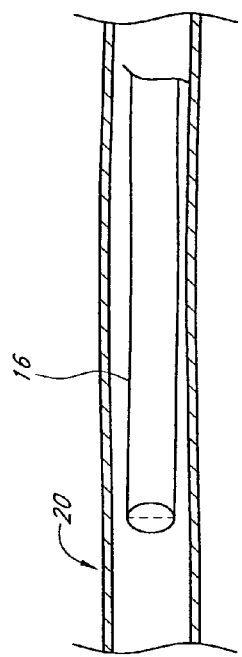
FIG. 2E depicts a portion of one embodiment of a method for delivering a fibrous mass structure to a hollow anatomical structure, showing a catheter or delivery sheath inserted into a hollow anatomical structure.

The following description and examples illustrate preferred embodiments of the present invention in detail. Those of skill in the art will recognize that there are numerous variations and modifications of this invention that are encompassed by its scope. Accordingly, the description of a preferred embodiment should not be deemed to limit the scope of the present invention.

Methods, systems, and apparatuses for occluding a hollow anatomical structure (e.g. FIG. 1) in a patient or subject using an occluding device or occluding material are provided. The terms "subject" and "patient" as used herein, refer to animals, such as mammals. For example, mammals contemplated by one skilled in the art include humans, primates, dogs, cats, sheep, cattle, goats, pigs, horses, mice, rats, rabbits, guinea pigs, and the like. The terms "subject" and "patient" are used interchangeably.

The terms "occluding device" and "occluding material" as used herein, are broad terms and are used in their ordinary sense, including, without limitation, a substance or device that is capable of occluding or causing occlusion of a hollow anatomical structure. Occluding materials or occluding devices can be formed or fabricated ex situ, or formed in situ (e.g., by curing of a prepolymer or uncured polymer). The term "occluding material" as employed herein, includes prepolymers, uncured polymers, unsolidified materials, as well as occluding materials inserted into a patient in polymerized, precured or solidified form. Biologic materials, e.g., gelatin, thrombin, can also be used separately or in combination with the occlusive materials. Bioresorbable materials are particularly preferred occluding materials, although other materials can also be used as desired. For example, in one embodiment, the fibrous mass structure can include fibers and/or other components formed from polylactides (PLA) and/or polyglycolides (PGA) or copolymers thereof.

Occluding can include, but is not limited to, blocking by insertion of a plug or other structure into the hollow anatomical structure (e.g., FIG. 1) that prevents or inhibits flow therethrough, adhering opposite walls of the hollow anatomical structure together so as to prevent or inhibit flow therethrough, compressing the walls of the hollow anatomical structure together so as to prevent or inhibit flow therethrough, or initiating a physiological reaction to an applied force or substance (e.g., energy, chemicals, drugs, physical contact, pressure or the like) that causes flow through the hollow anatomical structure to be inhibited or prevented (e.g., formation of a fibrotic plug, or growth of connective tissue). Occlusion can be immediate, or onset of occlusion can be delayed. Occlusion can be partial (permitting a reduced flow through the hollow anatomical structure) or complete (permitting no flow through the hollow anatomical structure). Occlusion can be permanent or temporary. Occlusion can be affected by resorption characteristics of the material. Occlusion can result in physical change or damage to the hollow anatomical structure (e.g., tissue fibrosis, or necrosis), or can block the hollow anatomical structure without substantial physical change (e.g., a biocompatible plug). The mechanisms by which occlusion can occur include but are not limited to formation of an organized fibrotic occlusion resulting from the body's natural foreign body healing response, formation of a wound or damage to tissue, expansion of the occluding device or occluding material, release of a chemical or bioactive agent (e.g., a sclerosant, inflammatory agent, cytokine, growth factor, clotting factor, tissue attachment factor, or other agent) from the occluding device or occluding material, venoconstriction, compression, and ligation. Other mechanisms, forms, and effects of occlusion will be appreciated by those of skill in the art.

Occlusive Structures

FIGS. 2A-D show one embodiment of an apparatus for treating a hollow anatomical structure. The apparatus comprises an implant 10 sized for insertion into the hollow anatomical structure 20. The term "implant" as used herein, is a broad term and is used in its ordinary sense, including, without limitation, a substance, structure or device that is capable of being implanted within a hollow anatomical structure. The implant 10 comprises a fibrous mass structure 12 including a plurality fibers 14. The implant 10 has a first density associated with an unstressed state of the implant 10 as shown in FIGS. 2A-B. The implant 10 has a higher second density associated with a radially compressed state of the implant 10 as shown in FIGS. 2C-D. The implant 10 preferably is compressible and self-expanding. For example, the implant 10 comprises a plurality of expandable fibers 14 that can expand from the compressed state of FIGS. 2C-D to the unstressed state of FIGS. 2A-B.

Expansion of the implant 10 is facilitated by the crimped configuration of individual fibers 14 of the implant 10. As shown in FIGS. 2A-D, the fibers 14 are crimped in both the compressed and unstressed state. The implant 10 comprises a plurality of loose, bulked fibers 14. The term "loose" as used herein with respect to the fibers 14, is a broad term and is used in its ordinary sense, including, without limitation, not securely attached as a whole (allowing for interconnection, joining, bundling or tying, in some locations, of a number (e.g. less than 50%) of the fibers short of the whole collection) along all or a significant portion (e.g. more than 10%) of the length of the implant 10. The term "bulked" as used herein with respect to the fibers 14, is a broad term and is used in its ordinary sense, including, without limitation, tending to occupy or create a greater volume, when placed among a collection of fibers, than a substantially straight fiber of similar denier or cross-sectional size.

The implant 10 additionally comprises a plurality of textured fibers 14. The individual fibers 14 of the implant 10 preferably are crimped, bulked and/or deformed by various commonly known fiber texturing processing techniques, such as, for example, hot air crimping, mechanical stuffer box crimping, false twist texturing, stretch texturing, draw texturing or other processes which allow the fibers 14 themselves to self expand, thus bulking and expanding the fibrous mass 12. Also, this texturing slows the flow of blood acutely which facilitates good tissue ingrowth and ultimate durable fibrotic occlusion. Also, this texturing allows the implant 10 to be deliverable in low-profile and expand up to fill the target hollow anatomical structure 20. One process for making a fibrous implant 10 includes repeated stretching of the textured yarn to "unlock" the texture that has been associated with the yarn. The fibers 14 are mechanically and repeatedly stretched. Stretching the fibers 14 helps them regain their bulk following texturing.

Thus, as shown in FIGS. 2A-D, the implant 10 preferably comprises a scaffold of loose fibers 14 that extend generally longitudinally and form a number of bends along the length thereof formed through the texturing and stretching processes. The term "scaffold" as used herein, is a broad term and is used in its ordinary sense, including, without limitation, a supporting framework or lattice which is possibly but not necessarily temporary in nature. The term "bends" as used herein with respect to the fibers 14, is a broad term and is used in its ordinary sense, including, without limitation, curved or angled changes of direction (e.g., apices) and/or the portions of the fibers that extend between the changes of direction.

The fibers 14 preferably are radially bulked. The term "radially bulked" as used herein with respect to the fibers 14, is a broad term and is used in its ordinary sense, including, tending to occupy or create bulk or volume in the radial direction (generally orthogonal or transverse to the long axis of the fiber when laid substantially straight) beyond the cross-section of the fiber. For example, because the fibers 14 have a crimped, bent, or undulating configuration as a result of the texturing and stretching processes, the fibers 14 collectively and/or individually become relatively shorter in the longitudinal direction, and relatively thicker in the radial direction. The fibers 14 thus create a scaffold having high void content and relatively low density. The crimped configuration of the fibers 14 promotes the self-expanding property of the fibers 14. Fibers 14 are biased towards the expanded state such that the implant 10 is expandable.

The fibers 14 can be from 0.1 denier to 10 denier and the implant 10 can comprise between 500 and 100,000 fibers in some embodiments. The implant 10 can comprise between 500 and 500,000 fibers in some embodiments. These fibers 14 are preferably loose, non-knit, and/or non-woven. For example, in some embodiments, the fibers 14 are not rigidly fastened or securely attached to each other. The fibers 14 preferably are relatively free to move and are generally not confined or restrained relative to each other along the length of the implant 10. In some embodiments, the fibers 14 can be joined at a first end portion of the implant 10. In some embodiments, the fibers 14 can be joined at a second end portion of the implant 10. Fiber sizes and configurations are described in more detail below.

The fibers 14 preferably are formed from one or more bioabsorbable and/or biodegradable materials. The term "bioabsorbable" as used herein, is a broad term and is used in its ordinary sense, including, without limitation, capable of being taken in and made part of an existent biological whole. The term "biodegradable" as used herein, is a broad term and is used in its ordinary sense, including, without limitation, capable of being broken down especially into innocuous products by the action of living things. In some embodiments, the fibers 14 are individually expandable. In some embodiments, the fibers 14 can be formed from an alpha-hydroxy acid, and/or formed from material selected from the group consisting of polyglycolic acid, polyglycolic-co-lactic acid, polylactic-glycolic acid, polyglycolide-co-lactide, and polyglycolide. These and other suitable materials are described in more detail below. The fibers 14 can comprise first fibers having a first bioabsorption rate and second fibers having a second bioabsorption rate, where the first bioabsorption rate differs from the second bioabsorption rate.

Figure 3:
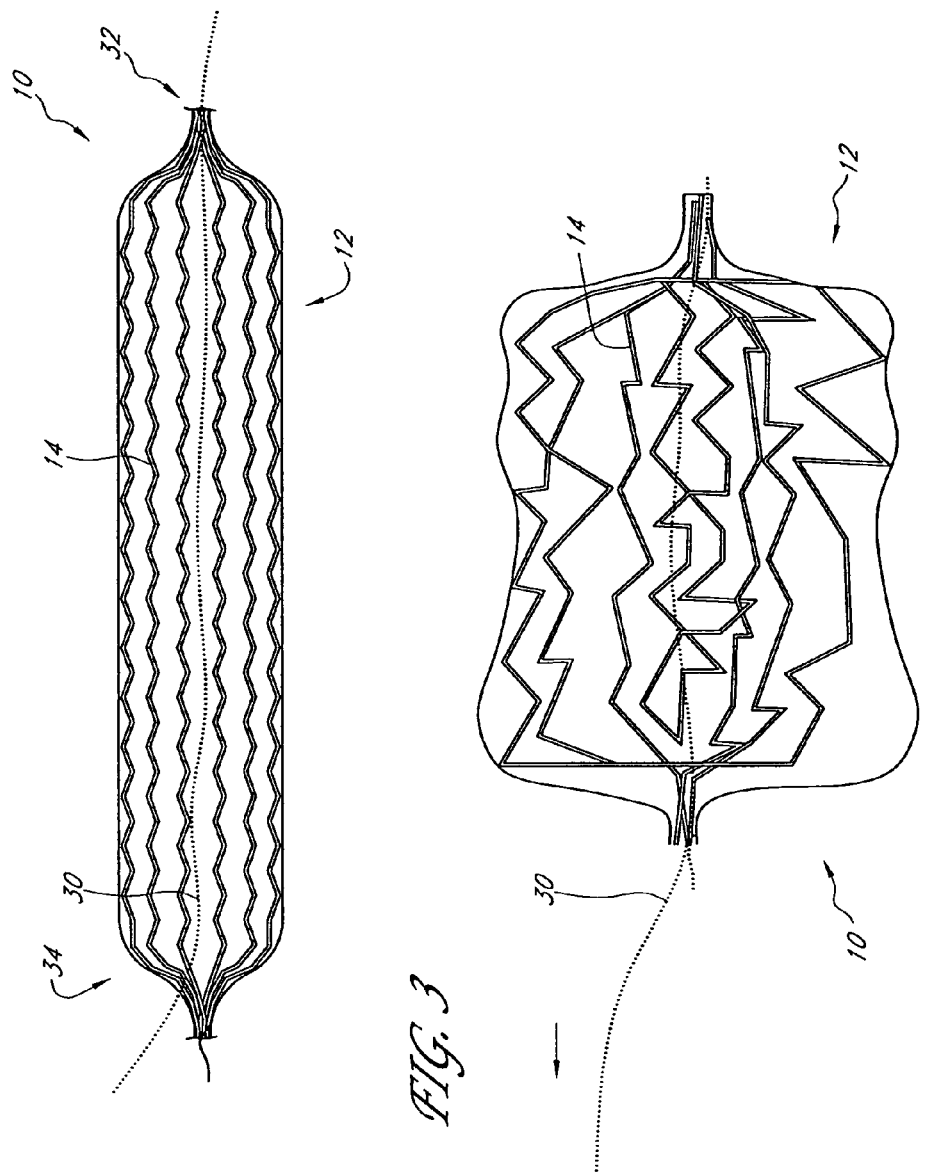
FIG. 3 depicts the fibrous mass structure in two use conditions.
Figure 4:
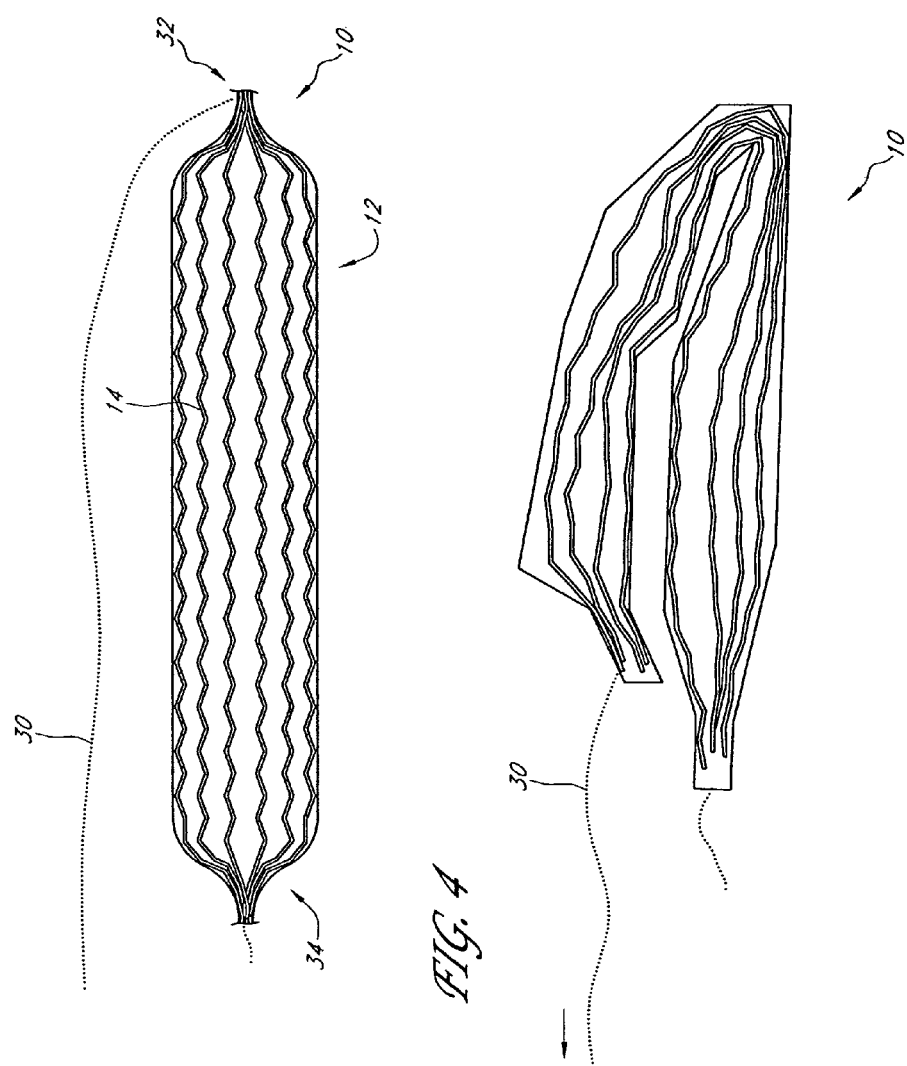
FIG. 4 depicts the fibrous mass structure in two use conditions, in a folding use context.
Figure 5:
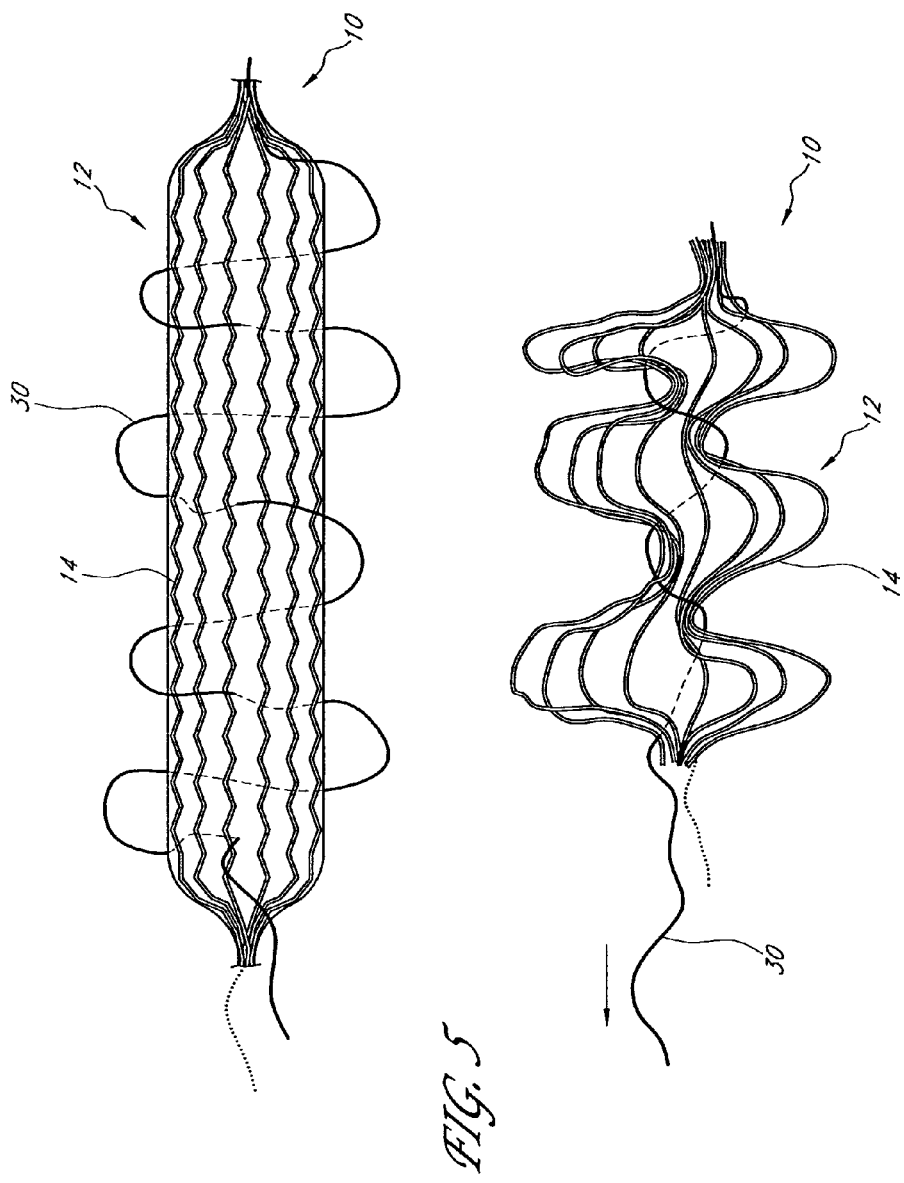
FIG. 5 depicts another fibrous mass structure with an interlaced pull member.
Figure 6:
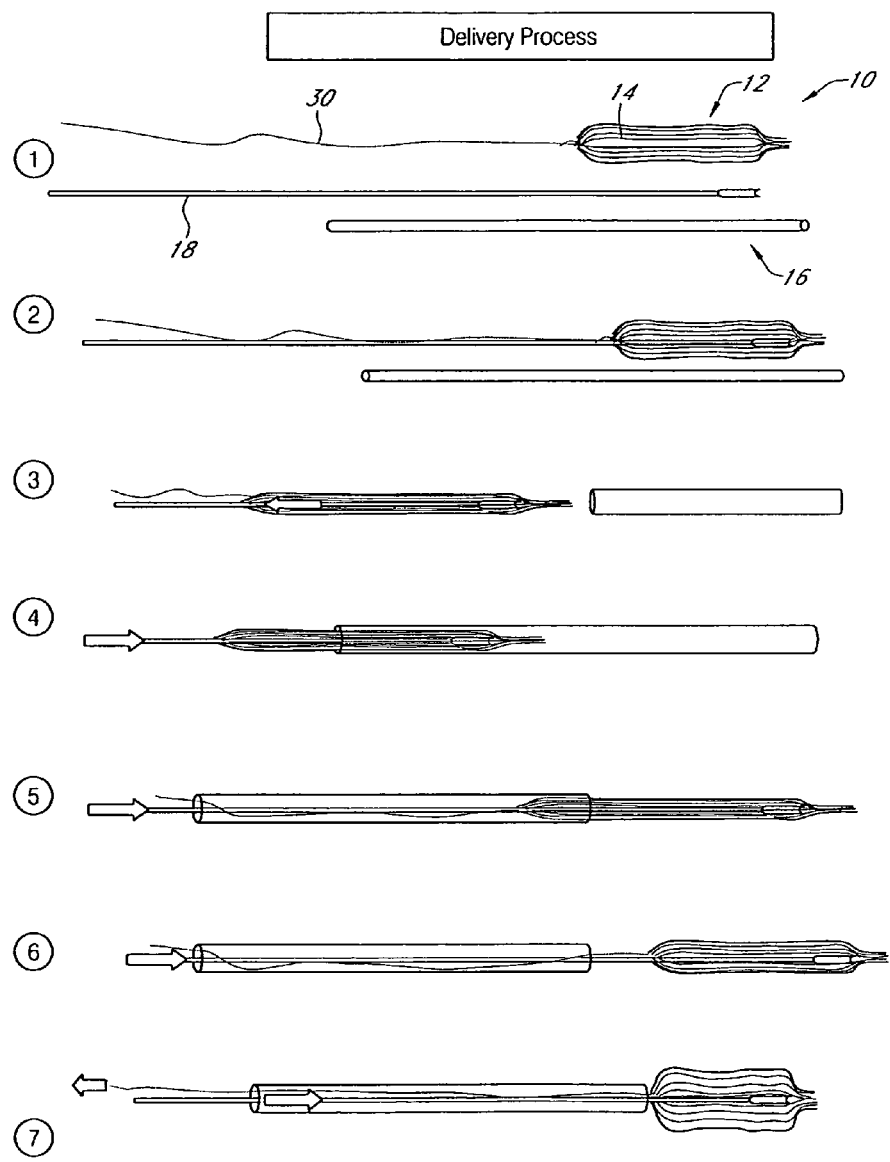
FIG. 6 illustrates one process of delivering a fibrous mass structure into a hollow anatomical structure such as a vein.

In some embodiments, the implant 10 can be radially expanded, folded over, bunched and/or tangled as shown in FIGS. 3-5. Additionally, one embodiment of a method of delivering an implant 10 is shown in FIG. 6 and described in more detail below.

In some embodiments, the apparatus can comprise a fixation element configured to limit migration of the implant 10 when in the hollow anatomical structure. The term "fixation element" as used herein, is a broad term and is used in its ordinary sense, including, without limitation, a device which tends to reduce or eliminate movement of a an object placed within a hollow anatomical structure. For example, the apparatus can comprise a tether coupled with the implant.

Figure 7:
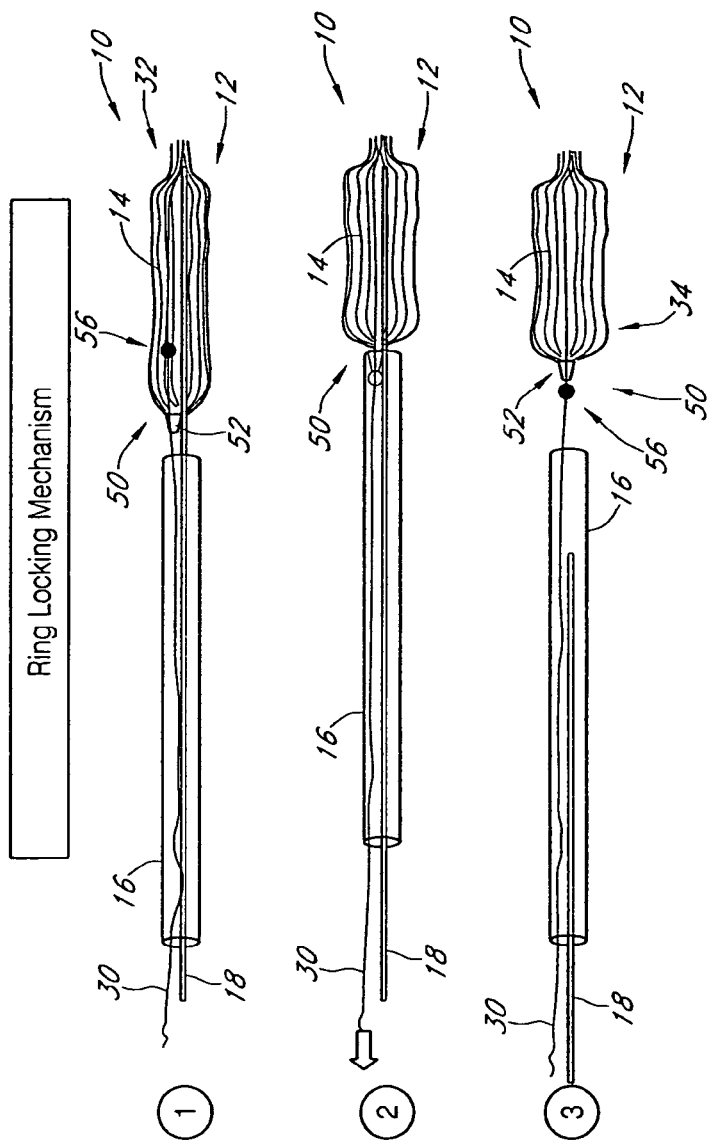
FIG. 7 illustrates the use of a ring locking mechanism in deploying a fibrous mass structure.
Figure 8:
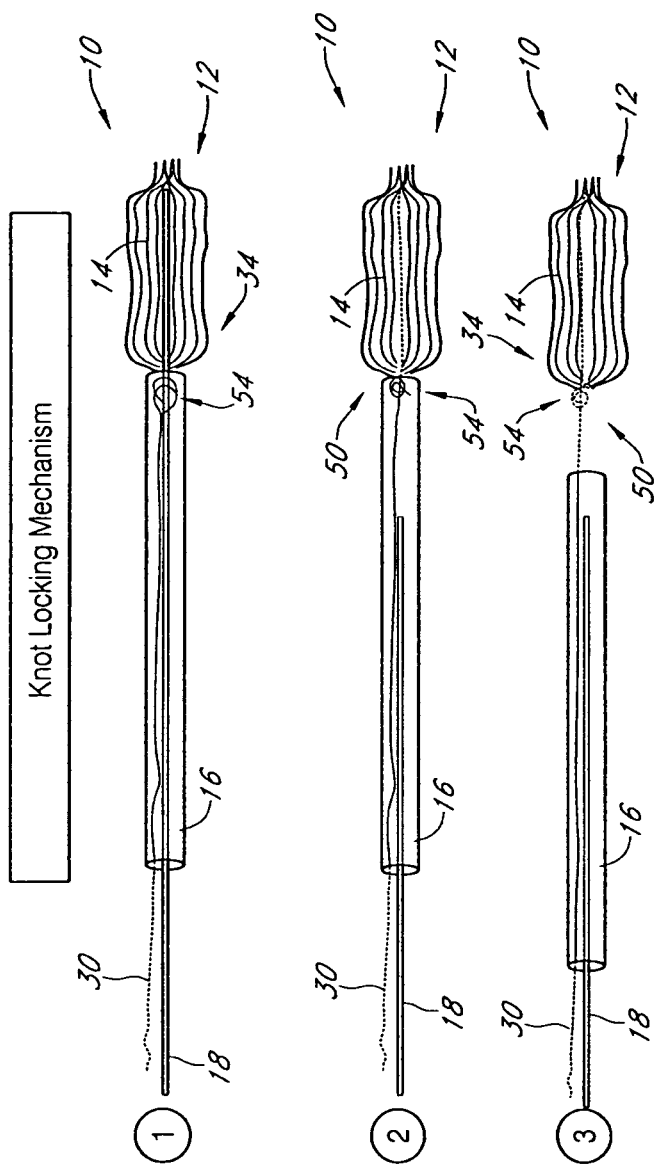
FIG. 8 illustrates the use of a knot locking mechanism in deploying a fibrous structure.

In some embodiments, the apparatus additionally comprises an implant locking mechanism, as discussed in more detail below with reference to FIGS. 7-9. The term "locking mechanism" as used herein, is a broad term and is used in its ordinary sense, including, without limitation, a structure for forming an interlocking or entanglement of elements or parts; a structure or device to secure in position, hold, or control a configuration; a structure to fix in place. For example, the apparatus can comprise a pull string 30 coupled with the implant 10 and configured to extend beyond at least one end portion of the implant 10. In some embodiments, the pull string 30 can position the implant 10 in an expanded configuration within a hollow anatomical structure.

As is described further below, in some embodiments, the implant 10 further comprises a radially expandable element. In some embodiments, the fibers 14 can be positioned generally interior to the expandable element when implanted in the hollow anatomical structure 20. In some embodiments, the implant 10 additionally comprises a drug and/or a sclerosant. In some embodiments, an outer surface of the scaffold can be abrasive. The term "abrasive" as used herein, is a broad term and is used in its ordinary sense, including, without limitation configured to irritate, rub or wear away for example by friction; or with reference to the outer surface of the implant 10, sufficiently abrasive to denude an endothelial layer when moved while in contact with the layer.

Figure 2F:
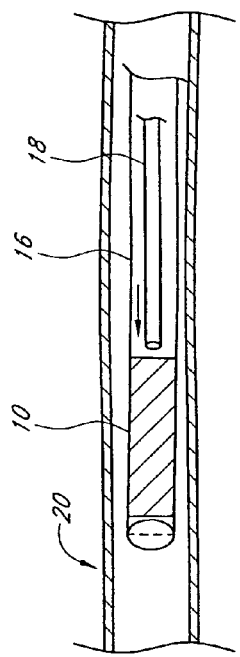
FIG. 2F depicts an implant in a low-profile configuration advanced with a pushrod through the catheter or delivery sheath according to the method of FIG. 2E.
Figure 2G:
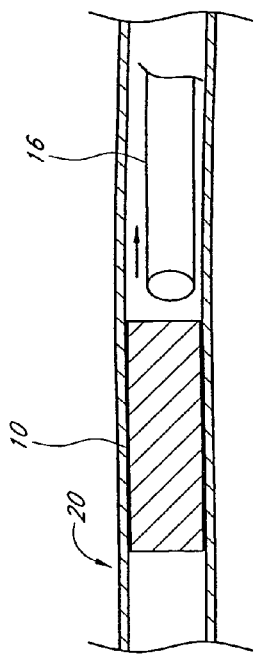
FIG. 2G depicts the implant in an expanded configuration within the hollow anatomical structure and the delivery catheter or sheath being withdrawn from the hollow anatomical structure according to the method of FIG. 2E.

FIGS. 2E-G illustrate one embodiment of a method of delivering an implant 10 into a hollow anatomical structure 20. The method is suitable for delivering one or more of a number of implants disclosed herein. As shown in FIG. 2E, a delivery catheter and/or sheath 16 is inserted into a hollow anatomical structure 20. According to one embodiment, the delivery catheter 16 preferably is 8F or smaller. In some embodiments, the delivery catheter is 6F. The hollow anatomical structure 20 has an inner diameter preferably 4 mm or larger. In some embodiments, the inner diameter of the hollow anatomical structure is 4-12 mm. In some embodiments, the inner diameter of the hollow anatomical structure is 4-20 mm. The hollow anatomical structure can be a vein, e.g., the greater saphenous vein, or short saphenous vein or other hollow anatomical structures, such as, for example, a fallopian tube, ovarian vein, or internal spermatic vein.

An implant 10, e.g., a fibrous mass structure 12, is loaded into the delivery catheter 16 as shown in FIG. 2F. The implant 10 preferably takes on a compressed configuration (such as that shown in FIG. 2C) when in the delivery catheter 16. The implant 10 is pushed to a distal end portion of the delivery catheter 16. In some embodiments, a pushrod 18 can be used to advance the implant 10. Pushrods 18 are described in more detail below. For example, in some embodiments, an implant 10 can be folded over its distal end to form a fold or apex at an intermediate portion of the implant 10. The distal tip of the pushrod 18 can engage the fold or apex to facilitate pushing the implant 10 into the hollow anatomical structure 20.

As shown in FIG. 2G, the implant 10 is pushed out of the distal end portion of the delivery catheter 16 and into the hollow anatomical structure 20. In some embodiments, the pushrod 18 can be used to urge the implant 10 distally. In some other embodiments, the pushrod 18 can be held generally stationary and the delivery catheter 16 can be pulled proximally to deliver the implant 10 into the hollow anatomical structure 20. As shown in FIG. 2G, the implant 10 preferably takes on a treatment state or expanded configuration (such as that shown in FIG. 2A) when in place in the hollow anatomical structure 20. The self-expanding properties of the fibers 14 and the implant 10 cause it to expand and span the hollow anatomical structure 20. The implant 10 preferably forms a scaffold for occlusive ingrowth and clotting in the implant 10, eventually forming a durable occlusion of the hollow anatomical structure 20 as discussed in further detail herein. When treating a saphenous vein such as the greater saphenous vein, the catheter 16 can be inserted into the hollow anatomical structure at an insertion site remote from the sapheno-femoral junction within the greater saphenous vein and advanced toward or to the sapheno-femoral junction. The implant 10 is then advanced through the catheter toward or to the sapheno-femoral junction. If desired, the implant 10 can be placed in the vein such that it extends from the sapheno-femoral junction all the way to the insertion site.

Additionally, one or more of the methods described herein can further comprise moving the implant 10 within the hollow anatomical structure 20 (either before initial implantation, within the catheter 16, or after initial implantation), into a final treatment position. Thus, it will be appreciated that the implant 10 and/or fibrous mass structure 12 of FIGS. 2A-D, and other implants 10 disclosed herein, can have a compressed state (e.g. FIG. 2C) in which the implant 10 fits within (and/or can pass through) a cylindrical tube (e.g. delivery catheter) having an inner diameter of 8 F or less. In some embodiments, the inner diameter of the cylindrical tube is 6-8 F. Accordingly, the implant 10 preferably can expand from the compressed state to an expanded state (e.g. FIG. 2A) wherein the implant 10 has sufficient size to span the inner diameter of a hollow anatomical structure 20 of 4-12 mm, and/or span the inner diameter of a cylindrical tube having an inner diameter of 24 F or greater. In some embodiments, the implant 10 has sufficient size to span the inner diameter of a hollow anatomical structure 20 of 4-20 mm. In some embodiments, the implant 10 can span the inner diameter of a cylindrical tube having an inner diameter of between 24-36 F. In some embodiments, the implant 10 can span the inner diameter of a cylindrical tube having an inner diameter of between 12-60 F. Alternatively, in some embodiments, the implant 10 can expand to a treatment state wherein the implant 10 has a transverse size sufficiently large to occupy an adult human greater saphenous vein of average size or larger.

In one embodiment, the implant 10 has a compressed state in which the implant 10 can fit within a cylindrical tube having an inside diameter of 8 French or less. The implant 10 preferably is expandable from the compressed state to a treatment state in which the implant 10 has a transverse size which is sufficiently large to occupy an adult human greater saphenous vein of average size. For example, in some embodiments, the implant 10 preferably is expandable from the compressed state to an expanded state in which the implant 10 has sufficient size to span the inside diameter of a cylindrical tube having an inside diameter of 24 French or greater. The implant 10 preferably has sufficient size, when in the expanded state, to span the inside diameter of a cylindrical tube having an inside diameter of 24-36 French. In some embodiments, the implant 10 preferably has sufficient size, when in the expanded state, to span the inside diameter of a cylindrical tube having an inside diameter of 12-60 French. The implant 10 can fit within a cylindrical tube having an inside diameter of 6-8 French when in the compressed state in some embodiments. The implant 10 can be self-expanding such that the implant tends toward the expanded state in the absence of external forces.

According to one embodiment, an occluding device or implant 10 comprises a fibrous mass structure 12, as shown in FIGS. 2-9A. The fibrous mass structure 12 can include one or more strands 14 of fiber material. The fibrous mass structure 12 can be positioned within a delivery sheath 16 for delivery into a hollow anatomical structure 20. As the delivery sheath 16 is withdrawn, the fibrous mass structure 12 is exposed within the hollow anatomical structure 20. The fibrous mass structure 12 preferably occludes the hollow anatomical structure 20 as will be described further below.

One advantage of using a fibrous mass structure 12 for occluding a hollow anatomical structure 20 is the ability to treat structures near nerves or the skin without concern for heat damage, paresthesia, skin burn or damage to other adjacent anatomical structures requiring protection from heat or other perivascular damage. In one embodiment, using a fibrous mass structure 12 is particularly useful for treating hollow anatomical vessels below the knee where the greater saphenous vein runs close to nerves. Additionally, in some embodiments, using a fibrous mass structure 12 can avoid the need to use tumescent anesthesia for hollow anatomical structure compression and pain management during the procedure. In one embodiment, general and/or regional anesthesia is not used. In one embodiment, local or topical anesthesia and/or semi-conscious sedation can be used for implantation of fibrous mass structure 12. In some embodiments, the fibrous mass structure 12 is particularly well suited for performing occlusions of tortuous veins. Additionally, a bioresorbable occluder can advantageously be used in the internal spermatic vein to treat varicoceles and the ovarian vein to treat pelvic congestion syndrome or fallopian tube occlusion and/or vas deferens for permanent contraception.

Any suitable materials can be employed to form the fibrous mass structure 12. These materials are preferably bioresorbable materials that can be fabricated into a desired form for insertion into the hollow anatomical structure. A suitable size and shape of the material can be selected according to the hollow anatomical structure to be occluded. The fibrous mass structure 12 can comprise a composite of two or more materials or a single copolymer with different bioresorption rates, different biodegradation rates, solubilities, porosities, strengths, rigidities, or the like. Materials and methods for manufacturing an implant will be described in more detail below.

The fibrous mass structure 12 preferably is long enough to treat a desired length of hollow anatomical structure with a single device. In some embodiments, the length of the fibrous mass structure 12 is between about 1 cm, or less, to about 60 cm, or more. In some embodiments, it is desirable to have a length short enough to treat a small section near, for example, the saphenofemoral junction. In some embodiments, it is desirable to have a length long enough to treat an entire vein from the groin to the knee. In some embodiments, it is desirable to have a length long enough to treat an entire vein from the groin to the ankle.

As shown in FIGS. 2-9A, in one embodiment, the fibrous mass structure 12 comprises a plurality of long, continuous, thin fibers 14 (which, in some embodiments can be plied into a yarn). Alternatively, the fibrous mass structure 12 can comprise a plurality of thin staple fibers, with lengths ranging from 2 cm to 100 cm. The fibrous mass structure 12 can have a first configuration for delivery and a second configuration for occluding the hollow anatomical structure 20. In the first configuration, the fibrous mass structure 12 has a relatively low-profile. The cross-sectional area of the fibrous mass structure 12 preferably is small enough to facilitate delivery through a delivery device, such as a delivery sheath 16. In the second configuration, the fibrous mass structure 12 has a relatively expanded profile.

The individual fibers 14 of the implant 10 and/or fibrous mass structure 12 are crimped, bulked and/or deformed by various commonly known fiber processing techniques, such as, for example, hot air crimping, mechanical stuffer box crimping, false twist texturing, stretch texturing, draw texturing or other processes which allow the fibers 14 themselves to self expand, thus bulking and expanding the fibrous mass 12. Alternatively, the fibrous mass 12 itself can be heat set, solvent cast, spin cast, molded, extruded, solvent sprayed, melt spun, electro spun, etc. in the expanded state.

For example, in some embodiments, fiber texturing can be advantageous acutely for self-expansion and/or volume filling. Fiber texturing can provide an implant 10 with a high void content scaffold which allows the implant 10 to space fill without over packing. Implants 10 comprising textured fibers 14 can improve patient comfort and can be important chronically for biologic occlusion, providing tissue scaffolding, and/or enabling durable occlusion. The texture of the fibers 14 facilitates the self expansion, volume filling and occlusive/scaffold properties of the implant 10. Also, this texturing slows the flow of blood acutely which facilitates good tissue ingrowth and ultimate durable fibrotic occlusion. Also, this texturing allows the implant 10 to be deliverable in low-profile and expand up to fill the target hollow anatomical structure 20. Texturing adds bulk to the fiber 14 and random arrangement of the fibers 14 further enhances the self-expansion, volume filling and occlusive/scaffold properties of the implant 10. Texturing can be done by S&Z false twist texturing with or without air tack, stuffer box texturing, air-jet texturing (entangling), stretch texturing, draw texturing or other commonly used textile yarn texturing methods.

As yarn is produced, emerging filaments or fibers preferably cool rapidly and solidify; they can also be 'drawn' by taking them up at a faster rate than that of the supply. Drawing can stabilize the molecular structure and strengthen the yarn by improving the molecular orientation. A spinneret can be used to produce a number of fine streams that can be solidified to make filaments or fibers. The filaments are drawn to orient the molecular structure and the melts are solidified by cooling them below their melting point (melt spinning). The flowing polymer preferably is filtered to prevent lumps, such as gels and foreign bodies, from clogging the holes in the spinneret.

The rate of heat flow away from the extruded filaments leaving the spinneret helps to determine the morphological structure of the yarn. Morphology relates to the degree of crystallinity and orientation. At high speeds, the shear rate in the extrusion zone (which is a function of the filament velocity) also affects the morphological structure. The amount of subsequent drawing of these filaments yet further affects the properties of the yarn. Draw ratios affect the strength of the partially oriented yarn (POY). The strength of the POY produced at low draw ratios may be insufficient for high speed texturing and thus it may be desirable to draw at the texturing stage to increase the filament strength. Thus, when the POY is being produced for draw-texturing, the texturing speeds in effect become linked to the extrusion speeds. Filaments are often wrapped around rotating cylinders or godets.

In most texturing systems, filaments or fibers are heat set into some sort of crimped or convoluted form, such that each filament or fiber is held as separate from its neighbors as possible. For filaments or fibers that cannot be heat set, it is possible to tangle the fibers to lock them mechanically. An example of this is air-jet texturing. Sometimes it is desirable to combine air-jet with false twist texturing. Air-jet texturing gives a product that is nearer to a staple yarn than is a false-twist textured yarn.

Texturing via stuffer box, air jet and S&Z false twist is well known in the art. Useful parameters are the frequency of the crimp and crimp retention. The ASTM standard on crimp recovery (retention) is D4031, which defines crimp contraction, in this context, as an indicator of crimp capacity or a characterization of a yarn's ability to contract under tension. When a textured yarn develops bulk, it shrinks, even under load. Crimp retention is relevant because it determines how much self expanding the yarn can undergo. Especially in the blood wetted state, this crimp retention parameter of the yarn determines how much fiber is required to completely scaffold and, ultimately, durably occlude a hollow anatomical structure.

Texturing methods are described in more detail by Peter R. Lord in the textbook titled "Handbook of Yarn Production", published in North America by CRC Press LLU, 2000 Corporate Blvd, NW, Boca Raton, Fla. 33431, USA in 2003, ISBN#0-8493-1781-9, which is hereby incorporated by reference herein in its entirety, and made a part of this specification.

One process for making a fibrous implant includes repeated stretching of the textured yarn to "unlock" the texture that has been associated with the yarn. In some embodiments, no additional heating or cooling is required. The fibers are mechanically and repeatedly stretched. Stretching can be performed by hand and/or by machine. In the case of yarns that have an air tack, this operation effectively removes the air tacks by untangling the tack. If the yarn does not have any air tacks, this operation still helps the spooled yarn regain its bulk since spooling tends to collapse some of the bulk due to the tension required to spool the yarn. Additional details on manufacturing various embodiments of the implant 10 and/or fibrous mass structure 12 are discussed below, in the section titled, "Manufacturing Occlusive Structures."

The long, continuous, thin fibers 14 of the fibrous mass structure 12 can be scrunched, e.g., compressed along a longitudinal axis of the fibrous mass structure such that the cross-sectional width of the fibrous mass structure 12 is increased to occlude the hollow anatomical structure 20. In some embodiments, the fibrous mass structure 12 has the ability to expand to several times the packed diameter upon exiting the delivery sheath 16, thus potentially obviating the need for scrunching. For example, the fibrous mass structure 12 in one embodiment is packed into a delivery sheath 16 having an inner diameter of about 2 mm. When the fibrous mass structure 12 is deployed from the delivery sheath 16 it can expand to fill a vein having a diameter of about 5 mm, or less, to about 20 mm, or more. In some embodiments, when the fibrous mass structure 12 is deployed from the delivery sheath 16 it can expand to fill a vein having a diameter of about 4 mm, or less, to about 20 mm, or more. In some embodiments, expansion of the fibrous mass 12 and hollow anatomical structure filling can rely on the fiber texturing, but may alternatively use the twists and turns made by the fibers 14 as they buckle during delivery so that subsequent delivery of the material tightly packs and compresses the previously deposited material to more completely fill the hollow anatomical structure 20.

As shown in FIG. 3, in some embodiments, a pull string 30 can be coupled with the fibrous mass structure 12. In one embodiment, the pull string 30 is coupled with a distal end 32 of the fibrous mass structure 12. The pull string 30 can be actuated by the user or constrained without actuation and in combination with a proximal push sheath (not shown) to cause the fibrous mass structure 12 to "scrunch," e.g., to shorten and thicken along the longitudinal axis, and expand radially, when deployed in the hollow anatomical structure, as will be described further below. In some embodiments, the pull string 30 can be automatically actuated. As shown in FIG. 4, in another embodiment, a pull string 30 is coupled with a distal end 32 of the fibrous mass structure 12 and the pull string 30 can be actuated by the user to fold the fibrous mass structure 12, as will be described further below. As shown in FIG. 5, in one embodiment, the pull string 30 is woven in and out of the fibrous mass structure 12 for better scrunch uniformity. Weaving the pull string 30 through the fibrous mass structure 12 can produce "accordion-like" bending along the fibrous mass to improve the expansion characteristics, as will be described further below.

In some embodiments, the pull string 30 can be used to "scrunch" the fibrous mass structure against a distal portion of the delivery sheath 16, or against the push rod 18. In some embodiments, the pull string 30, or an anchor string or tether string 40, can be used for retrieval or repositioning of the implant 10.

An anchor string 40 can be coupled to the fibrous mass structure 12 to pull or reposition the whole implant 10. The push rod 18 can also be used in some embodiments to push or reposition the whole implant 10 by pushing on the distal end and putting the implant 10 into tension. The distal portion of the delivery sheath 16 can also be used for repositioning while constraining the pull string 30. The action of repositioning and/or moving the implant 10 within the hollow anatomical structure can improve occlusion by disturbing/denuding the endothelial cell lining in the hollow anatomical structure 20. Additionally, the anchor string 40 can be fixed at the access site acting as a fixation element and/or anchoring mechanism to prevent the fibrous mass structure 12 from migrating within the hollow anatomical structure 20. Other mechanical means associated with the fibrous mass structure 12 on its distal or proximal end or along the implant length can be contemplated to secure the fibrous mass structure 12 to the hollow anatomical structure 20 for controlling implant migration including but not limited to hooks, barbs, self-expanding radial structures, wish-bone shaped expanding anchor wires, coil shaped hooks, radially expanding umbrella shapes, etc. Some or all of these can be made from non-bioresorbing and/or bioresorbing materials. Fibrous mass structure migration can also be controlled by first sealing/occluding the hollow anatomical structure using RF energy, heating coil energy, laser energy, or surgical techniques like vessel ligation as well as external manual compression of the hollow anatomical structure can be use to prevent acute migration. Additional fixation techniques and structures are described in more detail below.

In some embodiments, a balloon can be positioned within the fibrous mass structure 12. The balloon can be inflated to expand the fibrous mass structure 12 upon deployment. The balloon can then be deflated and withdrawn, leaving the expanded fibrous mass structure 12 in place. Advantages of using a balloon include displacing or minimizing the native fluid, such as blood present in the lumen, effectively stopping the blood flow thereby promoting the coagulation of the residual blood, preventing the implant 10 from migrating by anchoring the implant to the wall of the hollow anatomical structure 20. The balloon can also have a lubricious coating so that the clot and/or implant 10 does not stick to the balloon. Additionally, the balloon can also be made micro porous which can deliver sclerosant, thrombin, other bioactive agents to the implant site.

In some embodiments, the implant 10 comprises, or is coupled with, a marker. The marker can be used for visualization of the implant 10. The marker can be echogenic and/or radiopaque for visualization under ultrasound, x-ray, or other visualization means. In some embodiments, other visualization methods and markers can be used. In some embodiments, a first marker is positioned on a first end of the fibrous mass structure 12, and a second marker is positioned on a second end of the fibrous mass structure 12. In some embodiments, the fibers 14 and/or the fibrous mass structure 12 can incorporate trace metals including powdered tantalum, powdered tungsten, bismuth oxide, or barium sulfate to improve visualization. In some embodiments, the fiber composition can incorporate a physiologic/biologic marker which allows monitoring of implant 10 degradation byproducts as they transport during the degradation cycle.

In some embodiments, a push rod 18 can be used to deliver, deploy or secure the implant 10. In one embodiment, the push rod 18 is positioned within the fibrous mass structure 12 of the implant 10. In another embodiment, the push rod 18 is positioned proximal to the structure 12. In some embodiments, the push rod 18 engages the fibrous mass structure 12 to hold it in place while the delivery sheath 16 is withdrawn. As will be described further below, the push rod 18 can be used to deliver the fibrous mass structure 12 from the delivery sheath 16 into the hollow anatomical structure 20. In some embodiments, the fibrous mass structure 12 can be self-actuating. In other embodiments, the push rod 16 and fibrous mass structure 12 can be configured to cooperate such that the user can actuate the fibrous mass structure 12 to the scrunched configuration. In some embodiments the fibrous mass does not have an outer sheath. The fibrous mass is preferably placed using a push rod 16 with an atraumatic tip. This embodiment has the advantage of minimizing the time that the fibrous mass 12 is compressed within the sheath 16 thereby improving the expansion characteristics of the implant 10. Furthermore, having no delivery sheath allows more fibers 14 to be placed into the hollow anatomical structure 20 without the need to increase the size of the access port.

The various embodiments of the implant 10/310 disclosed herein can be employed to implement methods of forming an initial, partial occlusion of a hollow anatomical structure (such as a blood vessel or varicose vein), and then forming a subsequent, complete, substantially complete or more complete occlusion of the hollow anatomical structure. (In some embodiments, as the occlusion becomes more and more complete, the implant 10/310 will begin to be absorbed within the body; nonetheless, as the implant becomes completely or nearly completely absorbed, the corresponding more complete, more complete or substantially complete occlusion is considered to have been caused by the implant.)

One embodiment of such a method can be practiced as follows. The implant 10 is first inserted or implanted using any suitable technique disclosed herein, or any other suitable technique. The insertion preferably causes the fibers 14 of the implant 10 to span or substantially span the lumen of the hollow anatomical structure (or otherwise span or substantially span the cross section of the hollow anatomical structure), along some or all of the length of the implant 10. Where the hollow anatomical structure has a native fluid flow (e.g. a blood vessel or varicose vein), the inserted implant 10 forms an upstream or retrograde end where the implant 10 terminates 10 and faces upstream against the prevailing native blood flow, and a downstream or antegrade end where the implant 10 terminates and faces downstream. (As applied to the implant 10, the terms upstream, downstream, antegrade and retrograde should be interpreted with respect to the blood flow direction prevailing at time of treatment; e.g. for a refluxing vein the blood flow direction for purposes of interpreting these terms will be the abnormal, reversed flow direction.) The inserted implant 10 thus extends longitudinally, downstream and antegrade, from its upstream/retrograde end to its downstream/antegrade end.

The inserted implant 10 preferably forms an initial, partial occlusion of the hollow anatomical structure. The radially bulked, crimped or self-expanding property of the fibers 14 tends to create voids and fluid flow paths through the inserted implant 10. These flow paths preferably extend generally longitudinally through the inserted implant 10, in the antegrade direction from the upstream end thereof to the downstream end. Thus, the native fluid flow will initially proceed through the inserted implant 10 through these flow paths, preferably at a reduced flow rate relative to the previous, unobstructed hollow anatomical structure.

The flow paths also extend radially within the implant 10, such that flow is permitted through the inserted implant 10, even when not all of the length of the implant is inserted within the treated hollow anatomical structure (see, e.g., FIGS. 37A-37E). Thus, in an inserted implant 10, the flow paths can be considered to extend, and permit fluid flow, from a first inserted end of the implant 10, to a second inserted end thereof.

In certain embodiments, the initial, partial occlusion formed by the inserted implant 10 causes a reduction in fluid flow past the implant 10, or past its insertion site, by 10%-90%, or 20%-80%, or 25%-75%.

Gradually, the inserted implant 10 forms a complete or substantially complete occlusion of the hollow anatomical structure. Where the hollow anatomical structure is a blood vessel, the blood flowing between and through the fibers 14 begins to clot, which gradually closes off the flow paths through the implant 10. In some embodiments, tissue ingrowth proceeds from the hollow anatomical structure wall (or vessel wall) adjacent the inserted implant 10, into the fibers 14. Where present, this ingrowth also gradually closes off the flow paths between the fibers 14, leading to complete occlusion.

In some circumstances, this ingrowth can be fibrotic in nature, as fibroblast cells migrate and proliferate into the implant and lay down collagen within the implant, leaving a collagenous material that fills in the voids within the implant, and eventually consumes the implant fibers 14. Accordingly, in these circumstances, the natural wound healing cascade is employed to cause an initial partial occlusion followed by a (more) complete occlusion. The insertion of the implant 10 into the hollow anatomical structure can thus be considered a method which further involves initiating the wound healing cascade, causing an initial partial occlusion and eventually a (more) complete occlusion.

Certain embodiments of these methods of partial occlusion followed by (substantially) complete occlusion therefore preferably comprise irritating the hollow anatomical structure wall (or vessel wall) at or near the insertion site of the implant 10, or otherwise adjacent the implant 10. Where the hollow anatomical structure comprises a blood vessel, this irritating can comprise at least partially denuding the endothelial layer of the vessel wall at or near the (target) insertion site of the implant 10 (the location within the vessel where the implant 10 is (intended to be) placed), and/or in the vessel upstream and downstream of the implant 10 or its (target) insertion site, and/or otherwise adjacent the implant 10. Irritating can be performed using any suitable technique or apparatus disclosed herein (e.g. a brush of the type shown in FIG. 30, or where the sides of the implant 10 are sufficiently abrasive as disclosed herein, by irritating with the sides of the implant).

The creation of an initial partial occlusion of the hollow anatomical structure can advantageously inhibit movement or migration of the inserted implant 10, especially where the hollow anatomical structure has a native fluid flow (e.g., a blood vessel). By avoiding an acute, substantially complete occlusion, the partial occlusion inhibits migration of the implant 10 by a fluid pressure head that can develop at the upstream end of the implant, if insufficient fluid is permitted to pass through the implant. In addition, such a pressure buildup can cause the vessel walls to dilate, also leading to loosening and migration of the inserted implant 10. With an initial partial occlusion, the inserted implant 10 preferably has sufficient time to become securely fixed to the hollow anatomical structure walls, so that it can resist the fluid pressure that develops when the implant later creates an increasingly complete occlusion of the anatomical structure.

Delivery Techniques

In one embodiment, a kit for treating a hollow anatomical structure comprises a bioabsorbable fibrous implant 10, and a sheath 16 sized for insertion into the hollow anatomical structure 20 having an inner diameter configured to receive the implant 10 for delivery of the implant into the hollow anatomical structure. A pushrod 18 is sized for insertion into the sheath 16 and configured to advance the implant 10 through the sheath 16 for delivery of the implant 10 into the hollow anatomical structure 20. According to some variations, the sheath 16 comprises an abrasive element on its outer diameter. The abrasive element can be configured to engage a surface of the hollow anatomical structure 20 when the sheath 16 is inserted within the hollow anatomical structure 20. The kit can additionally comprise an implant locking mechanism 50. The implant locking mechanism 50 can comprise a pull string 30 configured to be coupled with the implant 10. The implant locking mechanism 50 can comprise a funnel 52 coupled with the implant 10. The pull string 30 can be knotted 54. The pull string 30 can comprise a plurality of bumps 56 along at least a portion thereof.

In another embodiment, a method of treating a hollow anatomical structure 20 comprises delivering into the hollow anatomical structure 20 an implant 10 comprising a plurality of loose tortuous fibers 14 formed from one or more bioabsorbable materials. For example, according to one technique, a method of treating a hollow anatomical structure 20 having a diameter of 4 mm or more comprises inserting into the hollow anatomical structure 20 a catheter having a size of 8

French or less. A bioabsorbable fibrous implant 10 is passed through the catheter and into the hollow anatomical structure 20. With the implant 10, the patency of the hollow anatomical structure 20 can be reduced. In some embodiments, the method further comprises occluding the hollow anatomical structure with the implant 10. The implant 10 can be expanded to a treatment state within the hollow anatomical structure 20 in some methods. The method can include promoting occlusive ingrowth with the implant 10 when the implant 10 is in the hollow anatomical structure 20. The hollow anatomical structure 20 can comprise a vein. In some embodiments, the hollow anatomical structure 20 comprises a greater saphenous vein. Inserting the catheter can comprise inserting the catheter at an insertion site spaced from the sapheno-femoral junction, and further comprise advancing the implant 10 from the insertion site to the sapheno-femoral junction. The hollow anatomical structure 20 can have a diameter of 4-12 mm in some embodiments. The hollow anatomical structure 20 can have a diameter of 4-20 mm in some embodiments.

In another embodiment, a method of treating a vein comprises accessing the vein at an access point spaced from a sapheno-femoral junction. A bioabsorbable fibrous body 12 is implanted into the vein through the access point. The body 12 is moved in the vein toward the sapheno-femoral junction. In some embodiments, the method additionally comprises securing the body 12 in the hollow anatomical structure 20 to limit migration of the body 12 within the vein. A sheath 16 can be inserted through the access point and the body 12 can be pushed with a pushrod 18 through the sheath 16 into the vein in some methods. A heat treatment can be performed on the vein, and the heat treatment can comprise one or more of delivering radio frequency energy, delivering heat energy from a resistive element, and delivering energy from a laser. The method can additionally comprise moving an end of the body 12 in the vein to the sapheno-femoral junction.

As shown in FIG. 6, according to one technique, an implant 10, e.g., a fibrous mass structure 12, is provided. A delivery sheath 16 and a push rod 18 are also provided. The implant 10 is loaded onto the push rod 18. The implant 10 is stretched and collapsed onto the push rod 18. The push rod 18 is used to load the implant 10 into the delivery sheath 16. Once a distal portion of the delivery sheath 16 has been positioned within a hollow anatomical structure 20, the push rod 18 is used to push the implant 10 out of the delivery sheath 16 or, alternatively, the push rod 18 is held still while the outer sheath 16 is retracted. The implant 10 expands partially upon exiting the delivery sheath 16. The implant 10 is further expanded and scrunched as the delivery sheath 16 is pushed forward and the pull string 30 is pulled backward or held still constraining its movement.

According to one technique, ultrasound can be used to determine the diameter of the hollow anatomical structure 20 to be occluded. The compressibility of the hollow anatomical structure 20 can be determined and a color-flow Doppler flow assessment can be performed. An appropriate access site is selected. Local anesthetic can be administered at the selected access site. An introducer sheath 16, cannula, or other access device can be positioned into an access vessel. In one embodiment, a 6 F sheath is used. In another embodiment, a 12 Ga cannula can be used. Any suitable access device can be used.

A delivery device, e.g., a delivery catheter or sheath 16, is inserted into the hollow anatomical structure 20 until a tip of the sheath is positioned at a distal portion of the treatment segment. The fibrous mass structure 20 preferably is positioned within the delivery device as will be described in more detail below. The location of the fibrous mass structure 12 preferably is verified using any suitable visualization technique, e.g., ultrasound, x-ray. In some embodiments, a marker can be positioned on the fibrous mass structure 12 such that it is clearly visible. The fibrous mass structure 12 is delivered into the hollow anatomical structure 20. If desired, the fibrous mass structure 12 can be positioned or repositioned within the hollow anatomical structure 20 under visualization. In some cases, it may be advantageous for one user to position the fibrous mass structure 12, while another user manipulates the visualization equipment.

The fibrous mass structure 12 preferably is deployed to an expanded configuration. Any suitable deployment technique and/or expansion technique can be used. As shown in FIG. 3, in one embodiment, a pull string 30 coupled to a distal portion 32 of the fibrous mass structure 12 is pulled to scrunch the fibrous mass structure 12. Scrunching the fibrous mass structure 12 increases the density of the fibers 14 in a given cross-section. As shown in FIG. 4, in another embodiment, a pull string 30 coupled to a distal portion 32 of the fibrous mass structure 12 is pulled to cause the fibrous mass structure 12 to fold over on itself. Folding the fibrous mass structure 12 increases the density of fibers in a given cross-section. As shown in FIG. 5, in another embodiment, a pull string 30 is coupled to a distal portion 32 of the fibrous mass structure 12 and is woven through intermediate portions of the fibrous mass structure 12. Intertwining the pull string 30 with the fibrous mass structure 12 results in controlled scrunching of the fibrous mass structure 12 and increases the density of fibers 14 in a given cross-section.

In some embodiments, the implant 10 is held in the scrunched position by a locking device 50. Any suitable locking device 50 can be used. In one embodiment, the implant 10 comprises a ring locking mechanism 50. As shown in FIG. 7, a stop 56 is positioned on the pull string 30. The pull string 30 is coupled with the distal end 32 of the implant 10 and is threaded through a relatively small funnel shaped portion 52 that is coupled with a proximal portion 34 of the implant 10. The pull string 30 is pulled through the funnel 52 with the delivery sheath 16 helping to hold the implant 10 (and thereby the funnel 52) still. The stop 56 is pulled through the funnel 52, but is sized large enough that it will not slide back through the funnel 52 in the opposite direction. Accordingly, the implant 10 is locked in the expanded scrunched configuration and the push rod 18 and delivery sheath 16 are removed.

In another embodiment, the implant 10 comprises a knot locking mechanism 50. As shown in FIG. 8, a knot 54 is loosely tied in the pull string 30 around the push rod 18. The knot 54 is located near a proximal portion 34 of the implant 10. The knot 54 is prevented from fully tightening before the push rod 18 is withdrawn. The pull string 30 is coupled with the distal end 32 of the implant 10. When the implant 10 is scrunched, the push rod 18 is removed and the knot 54 in the pull string 30 can be tightened to keep the implant 10 scrunched. Accordingly, the implant 10 is locked in the expanded scrunched configuration and the push rod 18 and delivery sheath 16 are removed.

Figure 9A:
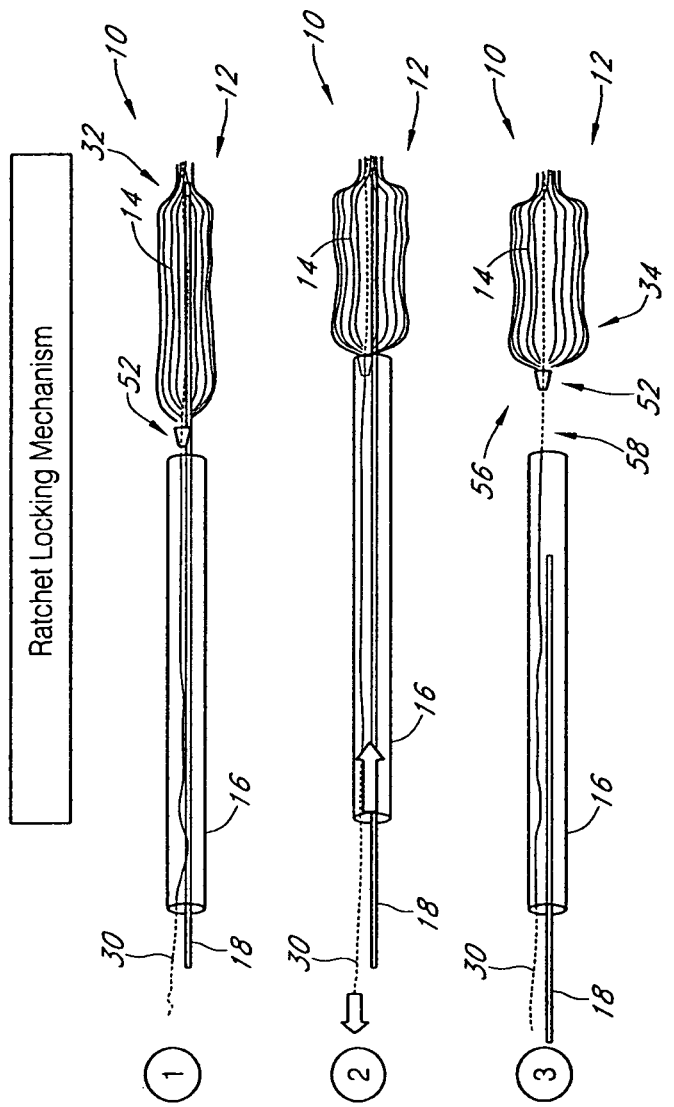
FIG. 9A illustrates the use of a ratchet locking mechanism in deploying a fibrous mass structure.

In another embodiment, the implant 10 comprises a ratchet locking mechanism 50. As shown in FIG. 9A, a plurality of detents or stops 58, are positioned along the pull string 30. In one embodiment, the stops 58 are similar to a cable-tie or zip-tie. The stops 58 can be positioned along part, or all, of the pull string 30. The pull string 30 is coupled with the distal end 32 of the implant 10 and is threaded through a relatively small funnel 52 shaped portion that is coupled with a proximal portion 34 of the implant 10. The pull string 30 is pulled through the funnel 52 with the delivery sheath 16 helping to hold the implant 10 (and thereby the funnel 52) still. The stops 58 are pulled through the funnel 52, but they are too large to slide back through the funnel 52 in the opposite direction. Accordingly, the implant 10 is sufficiently scrunched and then locked in the expanded scrunched configuration and the push rod 18 and delivery sheath 16 are removed.

After the implant 10 is delivered into the hollow anatomical structure 20, the fibrous mass structure 12 can be positioned or repositioned within the hollow anatomical structure 20 under visualization. The push rod 18 and anchor string 40 can be used to manipulate the implant 10. The delivery catheter can be withdrawn. The push rod 18 can be withdrawn. External compression may be applied during removal of the push rod 18 to help the implant 10 retain its position. The sheath 16 can be withdrawn. External compression may be applied during removal of the sheath 16 to help the implant 10 retain its position.

In some techniques, the implant 10 is permitted to dwell for a time period. The implant preferably is permitted to dwell for between about 1 min, or less, to about 30 minutes, or more. In some techniques, external compression can be applied to force the walls of the hollow anatomical structure 20 to collapse and stick to the implant 10. In some techniques, a vasoconstrictor can be applied to force the walls of a hollow anatomical structure 20 to collapse and stick to the implant 10. Following the dwell period, the position of the implant 10 is confirmed using any suitable method. In some cases, the position of the implant 10 is confirmed using a visualization technique, e.g., ultrasound, x-ray. In some cases, the position of the implant 10 is confirmed using palpation. Occlusion can be verified using any suitable method. For example, colorflow doppler can be used to evaluate or assess the occlusion.

Figure 9B:
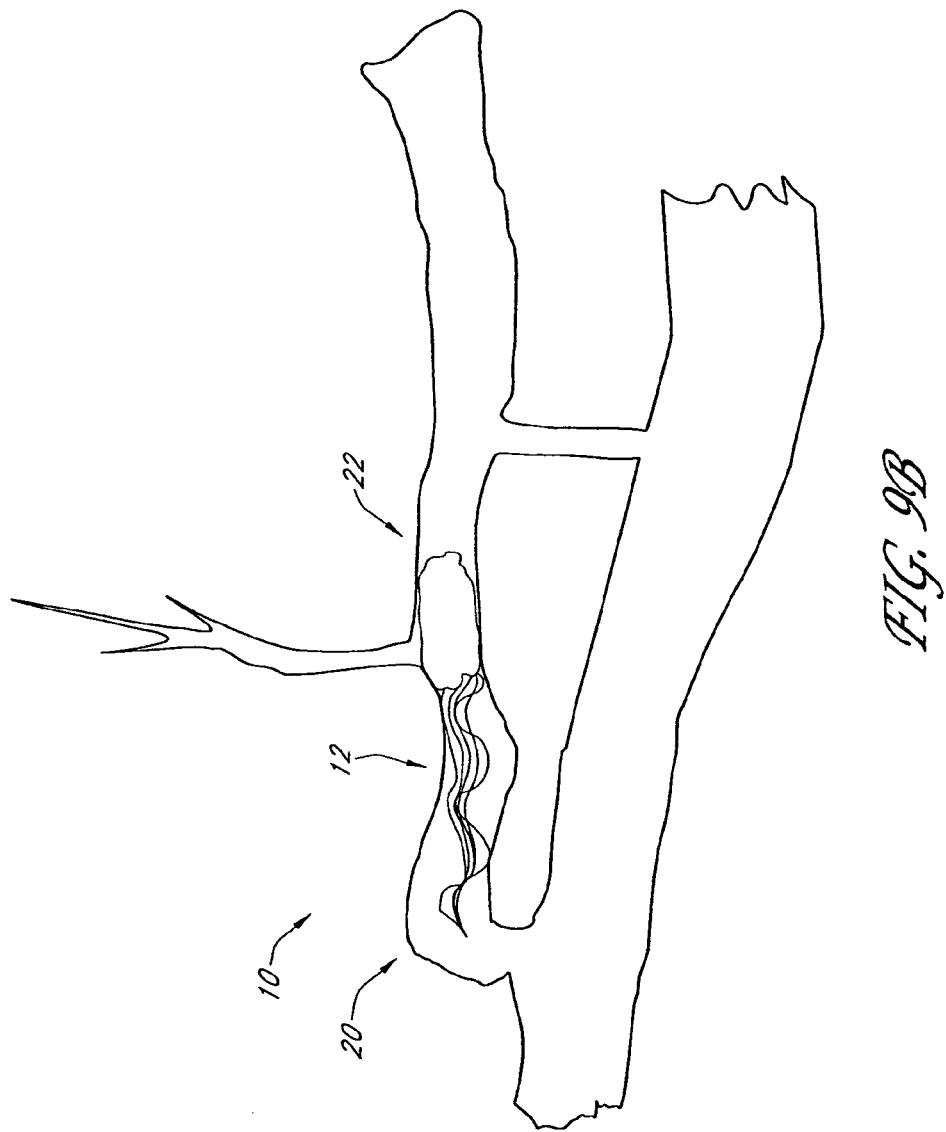
FIG. 9B illustrates another method and apparatus for occlusion of a hollow anatomical structure such as a vein.

As shown in FIG. 9B, according to another embodiment, an occluding device or implant 10 comprises a fibrous mass structure 12 and an injectable gelatin 22 or any other occlusive materials (as listed above) deployed simultaneously or sequentially into the hollow anatomical structure. The two materials can either be intermingled, or remain separated linearly along the hollow anatomical structure. The properties of the two materials are chosen and deployed in such a manner that the flowable material is prevented from migrating by the other material.

In some techniques, delivery of the implant 10 can be followed by an injection of sclerosant, hydrogel, or another active agent 22 and/or drug, as shown in FIG. 9B. Injection can be accomplished via use of a micro porous balloon catheter used to both deploy the fibrous mass 12 and to inject an active agent 22. In some techniques, the implant 10 can be pre-soaked in an active agent 22 in the operating room prior to delivery of the implant 10 to the treatment site. In some techniques, the implant is pre-soaked in an active agent 22 prior to packaging the device during manufacturing. In some embodiments, the implant 10 comprises active agents 22 as an integrated part of the device. The implant 10 can comprise a coating or drug-eluting technologies that function as an active agent 22. In some techniques, delivery of the implant 10 can be followed or preceded by non-localized delivery of an active agent 22. For example, the active agent 22 can be delivered orally or as a topical paste.

Blood preferably collects and coagulates in and/or around the fibers 14 of the implant 10. Initially, a thrombus is formed and preferably organizes as part of the foreign body natural healing process to create a fibrotic tissue occlusion. In some techniques, a growth factor can be used to promote fibrotic tissue growth. In some embodiments, a thrombin coating or seeding of the implant can initiate and promote the coagulation cascade in order to increase tissue ingrowth. There are many ways to stimulate tissue ingrowth in a biodegradable polymer. One method is to create a loose polymer scaffold (e.g., with any of the embodiments of the implant 10 disclosed herein) and fill the interstitial space with hydrogel, e.g., fibrin gel. Fibrin gel induces tissue ingrowth. Tissue growth factor, e.g., fibroblast growth factor, can also be incorporated into the implant 10 with the hydrogel to promote tissue ingrowth. In this approach, the scaffold is delivered first, and then fibrinogen, thrombin, and/or growth factor solution is injected into the vein. The solution fills in the interstitial space and polymerizes to form hydrogel, which serves as a matrix for rapid tissue ingrowth. An alternative approach to the fibrin gel is to directly mix autogenous blood with thrombin and inject the mixed blood into the vein. This creates a blood clot-like structure to fill the space and the clot's property can be controlled by thrombin concentration. This is also a good matrix to induce tissue ingrowth and has advantages over un-aided natural clotting. Another alternative, is to inject a fibrin or thrombin liquid rather than hydrogel into the sheath before the device is deployed to soak the implant 10 prior to introduction. As well, the implant 10 can be presoaked with this bioactive liquid and then dried as part of the fabrication process prior to clinical use in a clinical setting, or as part of a manufacturing process. According to another technique, a mix of autologous blood and fibrin is injected just before the device is deployed so that it develops or soaks the implant 10 in the outer sheath 16 before it is introduced into the hollow anatomical structure 20.

Additionally, there are other surface modifications or pretreatments that can be made to the implant 10. The surface of the fiber(s) 14 of the implant 10, as well as the material polymeric chain itself, can be modified or pretreated, e.g., charged, roughened, to be preferentially Fibrinogen-philic over Albumin-philic. The first thing that happens, e.g., within the first 1-3 seconds after implantation, with any hydrophobic implant material in the blood plasma stream is protein adsorption on the surface. Just as immediately, Factor XIIa is activated, starting the clotting cascade. If Albumin preferentially lays down on the implant 10 it will tend to passivate the surface rendering it less reactive. Thus, it is advantageous to prevent or limit Albumin adsorption and to preferentially adsorb Fibrinogen onto the surface by adjusting the polymer, or surface of the polymer, charging the surface, or by hydrophobicity. In some embodiments, pre-absorption of Fibrinogen onto the implant 10 promotes a non-passivation. In some embodiments, making surface modifications can improve fibrotic occlusion, with or without adding Thrombin. By the intrinsic clotting cascade mechanism, Thrombin acts on the Fibrinogen (a reactive protein monomer circulating in blood plasma, liquid) to become Fibrin monomers which are then cross linked by Factor XIII to become Fibrin (a solid). This cross linked Fibrin is an organized thrombus (i.e., a fibrotic occlusion). One example of this type of mechanism is Dacron (rough surface) which can be used on coils for occluding Berry Aneurysm's in the brain, as well as for woven and knitted grafts. Dacron is nicely hydrophobic, as well. Its surface preferentially adsorbs Fibrinogen over Albumin, quickly creating Fibrin and thus mural (wall) thrombus (all inside 10 minutes after implant) which helps to prevent endothelialization. However, silicones & polyurethanes are both very biocompatible and do not activate the clotting cascade as aggressively because they both adsorb Albumin more preferentially than Fibrinogen.

Other mechanisms that improve performance include inhibiting the natural fibrinolytic system in the region of the implant. As mentioned earlier, Factor XIIa starts the clotting cascade, but it also converts plasminogen to plasmin. Plasmin is not desired because it is an enzyme that lyses a thrombus (e.g., a clot). By inhibiting the conversion of plasminogen to plasmin, one can substantially prevent the natural tendency toward lysation of the desired blood clot adjacent to the implant. Plasmin is similar to Thrombin, except that Thrombin only cleaves fibrinogen to create fibrin monomers, which is desired. While Plasmin cleaves both fibrinogen and fibrin creating fibrin split products (FSPs) or fibrin degradation products. These FSPs are preferably removed in order to limit their inhibition of clot formation. These FSPs are preferably removed in order to limit their inhibition of clot formation. These FSPs inhibit cross linking of the fibrin monomers by preventing them from contacting each other so they can't create a fibrotic occlusion. For example, Tissue Plasminogen Activator (tPA) can be used for thrombolysis, as well as other drugs like ReoPro (a GPIIb/IIIa inhibitor that basically binds to human platelet IIb/IIIa receptors to prevent platelet aggregation). Therefore, drugs, surface coatings, and pre-treatments with bioactive agents are preferably used or administered to do the opposite, i.e., instead cause platelets to aggregate more aggressively and/or aggressively inhibit activation of plasminegin plasminogen in the region of the implant 10.

In some embodiments, bioactive agents that illicit the coagulation cascade to stabilize thrombus formation and promote a more durable foreign body response and fibrotic occlusion are desired. For example, in some embodiments, the implant 10 may be pre-treated with desirable therapeutic and clinical agents such as growth factors, tissue attachment factors, clotting factors, chemotherapeutic agents, chemotactic factors, and anti-bacterial agents. These agents may be covalently bonded, ionically or hydrophobically bonded, coated, compounded, physically absorbed into the implant, or otherwise combined with the implant. Some bioactive agents include but are not limited to: antibiotics such as tobramycin, entamycin, and vancomycin; clotting factors such as Factors I-VIII, thrombin, and fibrinogen; cytokines for example basic fibroblast growth factor (bFGF), platelet derived growth factor (PDGF), vascular endothelial growth factor (VEGF), transforming growth factor beta (TGF-$\beta$), TNF$\alpha$, NGF, GM-CSF, IGF$\alpha$, IL-1, IL-8, and IL-6; inflammatory microcrystals such as crystalline minerals and silicates; tissue attachment factors such as fibronectin, laminin, and vitronectin; protease inhibitors such aprotinin; extracellular matrix molecules such as collagen and fibronectin; trace metals; irritants such as trace amounts of talcum powder, metallic beryllium and silica; trace amounts of polymers such as polylysine and ethylenevinylacetate; other adhesion inducing agents such as monocyte chemotactic protein, fibroblast stimulating factor I, histamine, endothelin-1, angiotensin II, bromocriptine, methysergide, methotrexate, N-carboxybutyl chitosan, carbon tetrachloride, thioacetamide, quartz dust, fibrosin, and ethanol; or other molecules that stabilize thrombus formation or inhibit clot lysis for example proteins including Factor XIII, $\alpha$2-antiplasmin, plasminogen activator inhibitor-1 (PAI-1) or the like; as well as sclerosing agents such as morrhuate sodium, ethanolamine oleate, and sodium tetradecyl sulfate and anti-bacterial/anti-infective agents or antibiotic drugs like amoxicillin; ampicillin; benzylpenicillin; chloramphenicol; clindamycin; erythromycin; lincomycin; rifampicin or materials like silver or silver ions, colloidal silver, silver sulfadiazine, and/or silver nitrate.

The access site can be closed using any appropriate method, including through use of a fibrous mass structure 12. In some cases, a steri-strip can be used to close the access site. In some cases, the access site can be closed with a suture. Compression bandages can be placed on the patient. For example, where the surgical site is in a patient's leg, compression bandages can be positioned over the entire leg. Compression bandages preferably are left in place for about three days according to one technique. After about three days, the site can be scanned for deep vein thrombosis and/or extension of thrombus from the superficial to the deep system. The position of the implant is confirmed using a visualization technique, e.g., ultrasound, x-ray, or by palpation. Occlusion can be verified using any suitable method, e.g., color-flow Doppler, or contrast enhanced fluorographic x-ray.

Manufacturing Occlusive Structures

Figure 10:
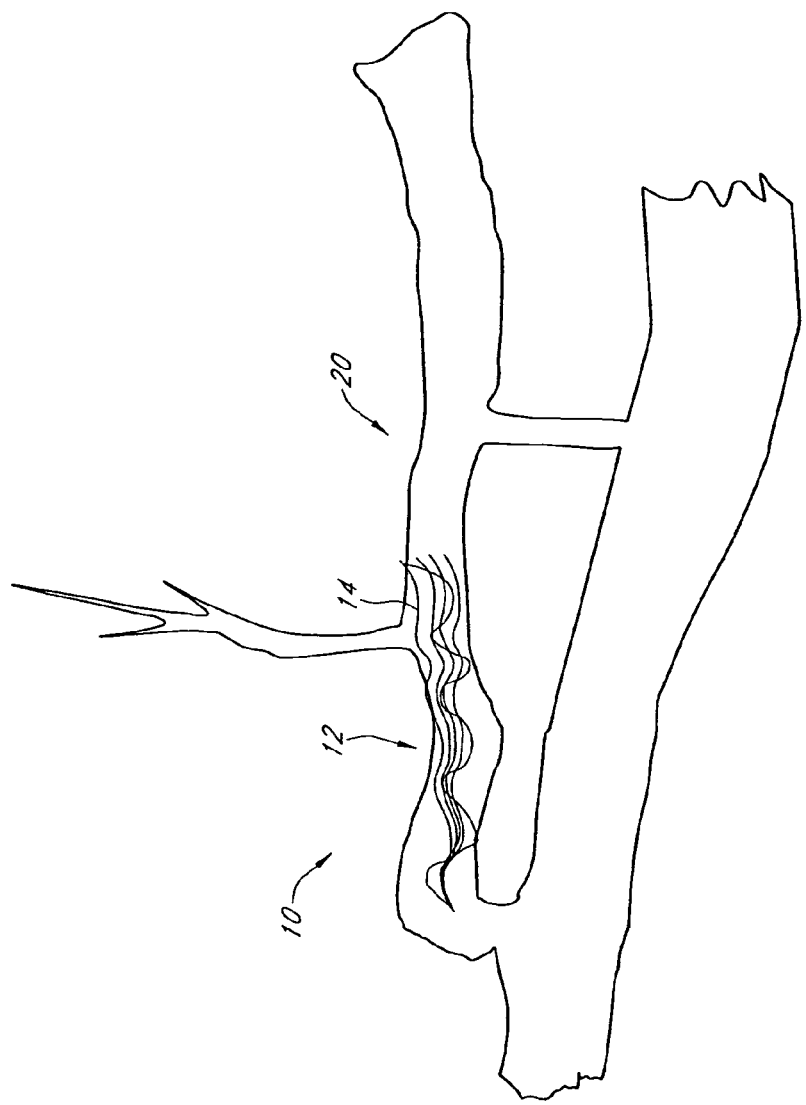
FIG. 10 illustrates another method and apparatus for occlusion of a hollow anatomical structure such as a vein.
Figure 11:
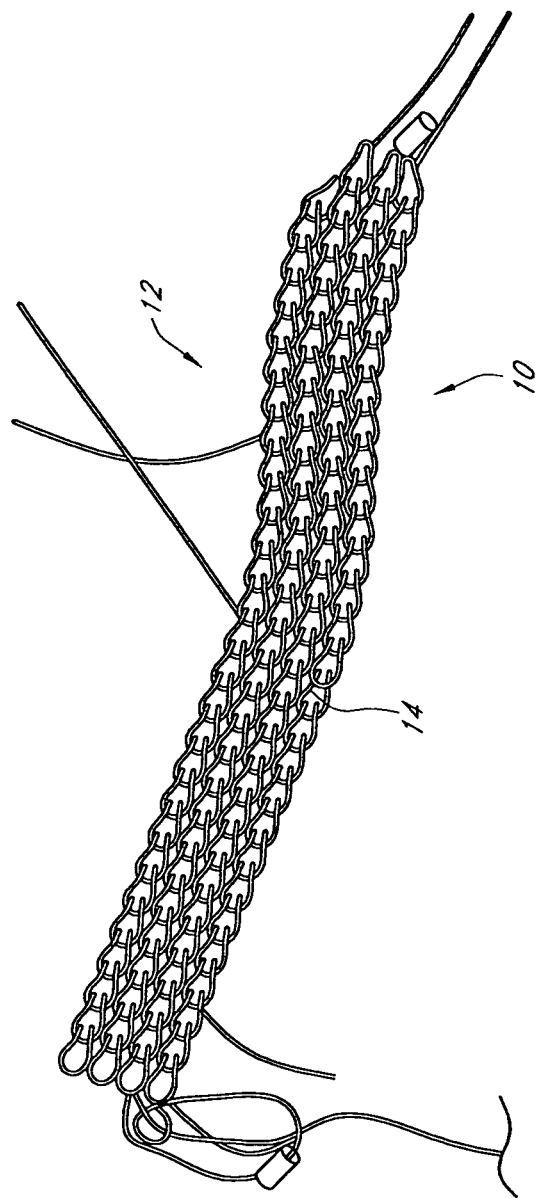
FIG. 11 illustrates a woven sock for occlusion of a hollow anatomical structure such as a vein.
Figure 12:
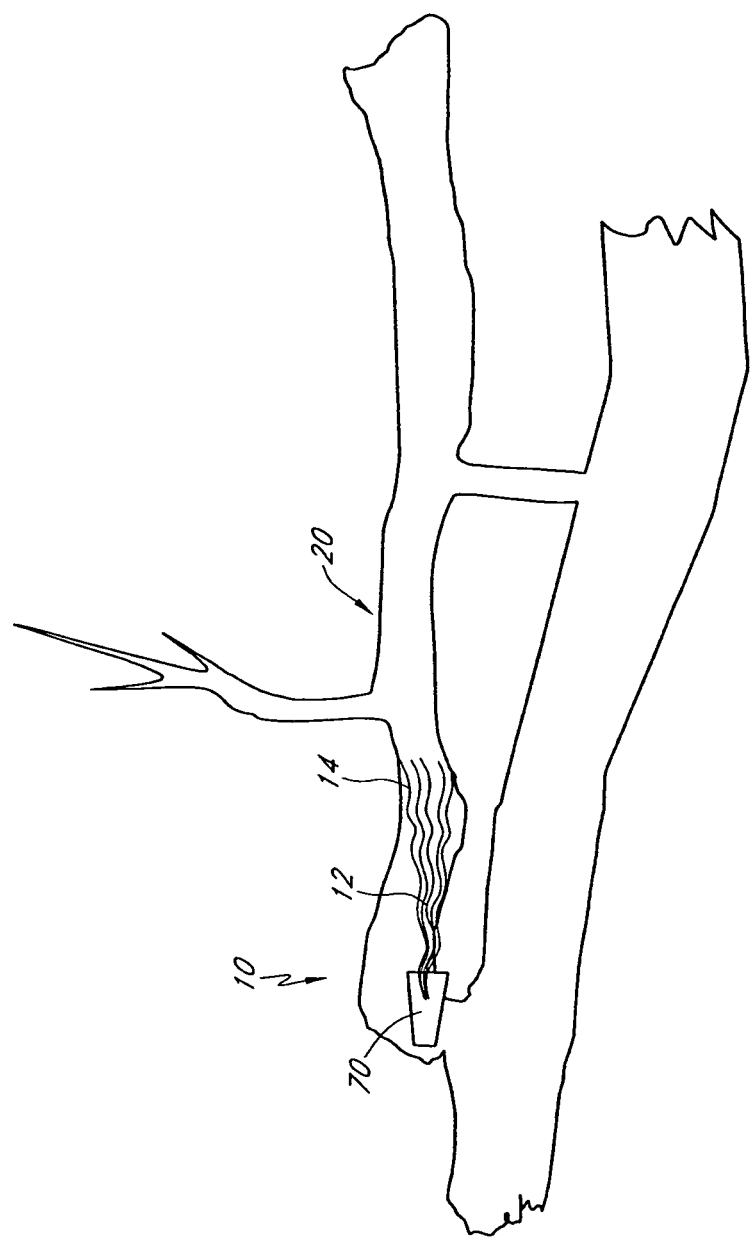
FIG. 12 illustrates another method and apparatus for occlusion of a hollow anatomical structure such as a vein.

The fibrous mass structure 12 can comprise any suitable shape and configuration. In one embodiment, the fibrous mass structure 12 is simply a bundle of long, thin fibers 14. In another embodiment, as shown in FIG. 10, the fibrous mass structure 12 is a bundle of long thin fibers 14 coupled together at one end, generally resembling a tassel or an "octopus." In another embodiment, the fibrous mass structure 12 is a bundle of long thin fibers 14 coupled together at a first end and a second end, as shown in FIGS. 2-9A. As shown in FIG. 11, in one embodiment, long, thin fibers 14 can be arranged to form yarn that can be processed into a tubular shaped structure, such as a sock. In some embodiments, the fibrous mass structure 12 can be coupled with another occlusive device. For example, as shown in FIG. 12, in one embodiment, a bullet-shaped bioresorbable plug 70 can be coupled with a bundle of long, thin fibers 14. In some embodiments, one or more of the fibers 14 preferably has a fiber diameter of between about 5 microns, or less, to about 30 microns, or more. In some embodiments, the fibers can have varying outward axial dimensions. The plug 70 can be positioned within a hollow anatomical structure 20, and the plug 70 and fibers 14 can occlude the hollow anatomical structure 20.

Figure 13:
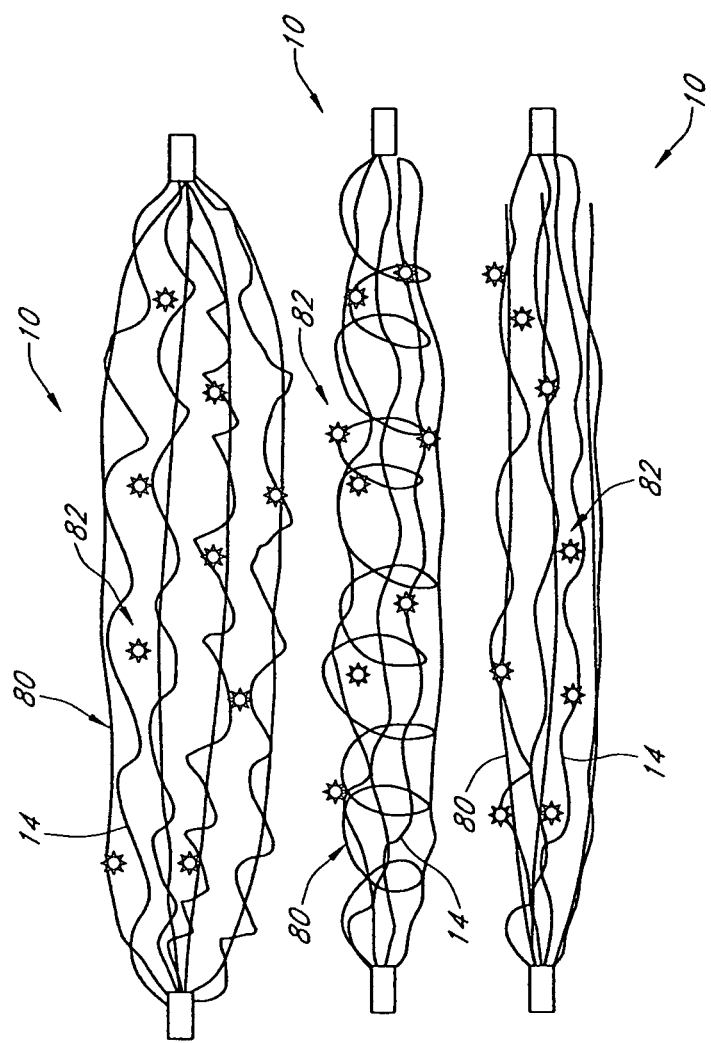
FIG. 13 illustrates further details of a fibrous mass structure.

As shown in FIG. 13, in some embodiments the implant 10 has a self-expanding element 80, e.g., a lattice, carcass, or coil, made from the same biodegradable material as the fibers 14 (or other biodegradable material) to hold the fibers 14 or strands more open to better fill the lumen space. The lattice, carcass, or coil structure 80 self expands once deployed in blood stream. The fibers 14 and the carcass 80 can be coupled at the proximal and/or distal end by any suitable coupling mechanism or, alternatively, coupled throughout the implant 10. Thrombin, fibrinogen, or other active proteins, peptides, and/or agents 82, can be applied to surface of the fiber material 14 or combined into an outer atomic layer of bioresorbable material to promote the surface to develop a fibrotic occlusion.

As described above, a self expanding internal element 80 can be provided, in some embodiments. This self expanding internal element may also be made from a bioresorbable material (e.g., a 0.010 inch, or less, to 0.012 inches, or more, monofilament). The self expanding internal element 80 can comprise, e.g., a carcass, a cage, a coil, a stent body, a braid, and/or another suitable lattice structure. The element 80 preferably is intertwined with a basic fibrous mass structure 12 described herein. The element 80 can be provided to improve volume filling to allow for treating larger vessels. The element 80 can improve implant to vessel wall contact to provide more consistent and reliable biologic occlusion. In some embodiments, the element 80 can be a short section coupled with a portion of the fibrous mass material 12. In other embodiments, the element 80 can extend along approximately the full length of the implant 10. In some embodiments, the element 80 can provide both anchoring properties and can reduce blood flow to facilitate better biologic occlusion. In some embodiments, portions of the fibrous mass structure 12 spaced from the self expanding element 80 can have a more loose texture, void content and scaffold, which can allow for some blood flow so that a pressure head is not developed which could extend the vessel diameter and may lead to implant migration.

Any suitable method can be used for manufacturing an implant 10 having a fibrous mass structure 12. Some methods for manufacturing the fibrous mass structure 12 can comprise one or more of knitting, weaving, felting, tangling, injection molding, heat forming, casting, spin casting, melt spun, electro spun, solvent casting, laser cutting, application of solvents, application of adhesives, extrusion, drawing, crimping, and other fiber processing techniques.

In one embodiment, the fibrous mass structure 12 can be formed by knitting fibers. In one embodiment a tubular fibrous mass structure 12 is knit with a knitting fixture, e.g., knitting knobby, knitting nelly. The size of the knitting fixture can be selected to produce an appropriately sized tubular fibrous mass structure 12. Any suitable number of cables can be used. A knitting fixture having an appropriate number of pins can be selected based on the desired number of cables needed to achieve the desired thread count and the desired porosity of the finished weave. In one embodiment, the fibrous mass structure 12 can be formed by weaving the fiber materials to form a tubular fibrous mass 12. In another embodiment, the fibrous mass structure 12 can be formed by felting the fiber materials to form a dense non-woven mesh. Non-continuous or staple yarns can also be used to form the fibrous mass 12. Carding, drawing, ring spinning, roving, general texturing by heat setting the filaments into a crimped or convoluted form are used to process the fibers. It is also possible to mechanically lock the fibers or to tangle the fibers when heat setting has a detrimental effect on the biodegradable material properties such as in air jet texturing.

A combination of staple and filament yarns can also be used to make the fibrous mass 12. An example of this involves wrapping of continuous filaments around the staple fiber bundles or low twist staple yarns. The staple and filament yarns can be composed of different base materials.

According to one embodiment, fiber processing can comprise applying a spin finish to the materials to allow for a false twist texturing. The false twist texturing can be used to bulk up the yarn. An S-twist can be applied to the yarn. The yarn is heated in the twisted configuration. The yarn is preferably heated to between about 60 degrees C., or less and about 150 degrees C., or more depending on the base material's inherent transition temperatures. In other embodiments, temperatures outside of this range, and/or partially overlapping this range, can also be used. The yarn is then cooled and untwisted. Downstream annealing, detorquing, elongation reduction steps may be eliminated to enhance the texturing of the implant. The material can also be heated, stretched and relaxed several times to further bulk the yarn.

In another embodiment, the fibrous mass structure 12 can be formed by injection molding. Materials can be heated above their melting points and injected into a space between a positive mold and a negative mold to form the fibrous mass structure 12. In some embodiments, the materials are injected only into the negative mold. In another embodiment, the fibrous mass structure can be formed by heat forming. Materials can be pressed between a positive mold and a negative mold and heating below the melting point to retain the molded shape. In one embodiment, PLA, PGA, or other material yarn can be heat set into shapes while retaining the original loft of the yarn.

In another embodiment, the fibrous mass structure 12 can be formed by casting. For example, in one embodiment, gelatin, or another material, can be poured into tubes to form the fibrous mass structure 12. In another embodiment, the fibrous mass structure 12 can be formed by spin casting. In another embodiment, the fibrous mass structure 12 can be formed by solvent casting. For example, in one embodiment, a positive mold can be dipped into a solution to form the fibrous mass structure 12. In another embodiment, a solution can be poured into a negative mold to form the fibrous mass structure 12. In another embodiment, a solution can be poured into the space between a negative mold and a positive mold to form the fibrous mass structure 12. In another embodiment, porous structures or foam castings created during solvent casting can be made by adding water dissolvable substances, e.g., salt, to the materials during casting and then dissolving the salt after curing. For example, solvent casting PLLA in methylene chloride or other solvent in the presence of a porogen such as salt crystals. In another embodiment, porous structures can be made by adding ammonium bicarbonate to form gas-filled voids in the materials forming the fibrous mass structure 12. In another embodiment, solvent casting techniques can be used to create a fibrous mass structure 12. Fiber bonding is accomplished by immersing PGA fibers in a PLLA solution. When the solvent evaporates, the network of PGA fibers is embedded in PLLA. Further heating allows the formation of a matrix of the two fibers. Methylene chloride or other solvent is then used to dissolve the PLLA, leaving behind a PGA fibrous mass structure 12.

In some embodiments, secondary processing can include laser cutting, application of solvents, and/or application of adhesives to further define the fibrous mass structure 12. For example, in one embodiment, PLA and methylene chloride or other solvent can be used to prepare the fibrous mass structure 12.

Bioresorbable Materials

Suitable materials for forming fibers 14 and/or other components can include one or more biodegradable polymers. For example, suitable biodegradable polymers can include alpha-hydroxy acids, such as polyglycolides, polylactides, and copolymers of lactic acid and glycolic acid. Poly(lactic-glycolic acid) (PLGA) is a suitable material in some embodiments. PLGA is a synthetic absorbable copolymer of glycolide and lactide marketed under the trade name VICRYL™ (a Polyglactin 910 manufactured by Ethicon, a division of Johnson & Johnson of Somerset, N.J.). It is absorbed though enzymatic degradation by hydrolysis. Polyglycolic acid (PGA) is a synthetic absorbable polymer. Polylactide (PLA) is prepared from the cyclic diester of lactic acid (lactide). Foams made from bioresorbable PLAs and/or PGAs are particularly preferred.

The fibrous mass structure 12 preferably comprises fibers and/or other components formed from one or more biodegradable polymers described herein, and/or disclosed in U.S. Provisional Patent Application No. 60/605,843, filed Aug. 31, 2004, titled APPARATUS AND MATERIAL COMPOSITION FOR PERMANENT OCCLUSION OF A HOLLOW ANATOMICAL STRUCTURE; in U.S. patent application Ser. No. 11/212,539, filed Aug. 26, 2005, titled APPARATUS AND MATERIAL COMPOSITION FOR PERMANENT OCCLUSION OF A HOLLOW ANATOMICAL STRUCTURE; Ser. No. 09/859,899, filed May 16, 2001, titled STENT GRAFTS WITH BIOACTIVE COATINGS; Ser. No. 09/861,182, filed May 18, 2001, titled INJECTABLE DRUG DELIVERY SYSTEMS WITH CYCLODEXTRINE POLYMER BASED HYDROGELS; and U.S. Pat. No. 4,938,763, issued Jul. 3, 1990; U.S. Pat. No. 5,456,693, issued Oct. 10, 1995; U.S. Pat. No. 6,423,085, issued Jul. 23, 2002; U.S. Pat. No. 6,676,971, issued Jan. 13, 2004, and U.S. Pat. No. 6,699,272, issued Mar. 2, 2004, which are all hereby incorporated by reference herein in their entireties and made a part of this specification.

For example, in one embodiment, the fibrous mass structure 12 can include fibers 14 and/or other components formed from polylactides and/or polyglycolides. As stated above, Polyglycolide (PGA) is a synthetic absorbable polymer. Polyglycolide, which exhibits hydrolytic susceptibility, is typically absorbed within a few months post-implantation. Polylactide (PLA) and polyglycolide (PGA) are prepared from their cyclic diesters of lactide and/or glycolide by ring opening polymerization to synthesize higher molecular weight polymers or by direct polycondensation of lactic acid and/or glycolic acid to synthesize lower molecular weight polymers. Lactic acid is a chiral molecule existing in two optical isomers or enantiomers yielding three stereo configurations. The L-enantiomer is the biologic metabolite, while the D-enantiomer and a D,L racemic mixture results from the synthetic preparation of lactic acid. The time required for poly-L-lactide to be absorbed by the body is relatively long compared to other bioabsorbable materials especially when in the high molecular weight form. In some embodiments, the fibrous mass structure can comprise fibers and/or other components formed from epsilon-caprolactone, PEG, collagen, gelatin, starch, poly(acrylamide-co-hydrazide), and/or other bioresorbable materials described herein.

Many resorbable homopolymers and copolymers may be used for this device and include but are not limited to the following: polymers derived from lactide, glycolide, and caprolactone which are common in clinical use and are characterized by degradation times ranging from days to years depending on the formulation and initial Mw (Molecular Weight). Lactic acid is a chiral molecule, existing in L and D isomers (the L isomer is the biological metabolite), and thus "polylactic acid" actually refers to a family of polymers: pure poly-L-lactic acid (L-PLA), pure poly-D-lactic acid (D-PLA), and poly-D,L-lactic acid (DL-PLA). Homopolymers of L-PLA as well as poly-caprolactone (PCL) have been useful clinically and are acceptable candidates. Additionally, polyglycolic acid (PGA), poly-glycolic/poly-L-lactic acid copolymers, poly(dioxanone), poly(trimethylene carbonate) copolymers, and poly(hydroxybutyrate) (PHB) and copolymers of hydroxybutyrate with hydroxyvalerate as well as polyanhydrides, polyorthoesters, polyphosphazenes, and others including natural biodegradables like collagen, elastin, fibrinogen, fibronectin, vitronectin, laminin, gelatin and lyophilized small intestine submucosa and combinations thereof are potential candidate material choices for this device.

In some embodiments, the degradation rate of the fibrous mass structure can be selected by varying the ratio of bioresorbable materials with pre-determined individual degradation rates. For example, in one embodiment, the fibrous mass structure comprises about 50% PGA and about 50% PLA. In another embodiment, the fibrous mass structure comprises about 65% PGA and about 35% PLA. In another embodiment, the fibrous mass structure comprises about 70% PGA and about 30% PLA. In another embodiment, the fibrous mass structure comprises about 80% PGA and about 30% PLA. In another embodiment, the fibrous mass structure comprises about 90% PGA and about 10% PLA. In another embodiment, the fibrous mass structure comprises about 100% PGA. In another embodiment, the fibrous mass structure comprises about 100% PLA.

The selection of the degradation period is based on maintaining a durable occlusion. The material degradation term preferably is chosen to ensure durable fibrotic occlusion through tissue ingrowth, but not too quickly that occlusion is unable to mature or that the material embolizes before occlusion. As tissue grows in, the implant preferably is going away. If the implant resides too long then there is potential for the patient to have a palpable cord along the leg.

In some embodiments, materials having molecular weights within a certain range are chosen to achieve a certain degradation time. For example, materials can have a molecular weight of between about 1,000, or less, to about 100,000, or more Daltons, to produce a desired degradation time period. Materials having intrinsic viscosities of between about 0.1 dl/gm, or less, to about 4 dl/gm, or more, can affect the degradation rate and the ease of processing of the materials. In some embodiments, the degradation time period preferably is between about 2 weeks, or less, to about 2 years, or more. In some embodiments, one or more of the materials can produce a desired inflammatory response within the patient. In some embodiments, one or more of the materials can produce a localized reaction, e.g., a pH change, as the material biodegrades.

In one embodiment, yarn fibers can be formed from one or more of the materials described. In some embodiments, the fibrous mass structure 12 can be between about 40 denier, or less, to about 7200 denier, or more. In some embodiments, the fibrous mass structure 12 can be between about 200 denier, or less, to about 15000 denier, or more. A fibrous mass structure 12 can comprise between about 1 fiber to about 24 fibers, or more, in some embodiments. A fibrous mass structure 12 can comprise between about 24 fibers to about 600 fibers, or more, in some embodiments. One or more of the fibers preferably has a fiber diameter of between about 5 micron, or less, to about 30 micron, or more, in some embodiments. In other embodiments, the fibers can be from 0.1 denier to 10 denier and the implant can comprise between 500 and 100,000 fibers in some embodiments. In some embodiments, the implant can comprise between 500 and 500,000 fibers. In some embodiments, the fibers can be from 5 denier to 50 denier in some embodiments. In some embodiments, the implant can comprise between 10 and 1,000 fibers in some embodiments.

In some embodiments, different copolymer fibers 14 can be mixed into a larger yarn for differential biodegradation along the length of the fibrous mass structure 12. For example, in one embodiment, different fibers 14 can be intertwined with the yarn near a front end of the fibrous mass structure 12 to act as a filter for the back end. In another embodiment, different fibers 14 can be intertwined with the yarn such that the fibrous mass structure 12 has different rates of degradation at different portions of the fibrous mass structure 12. In one embodiment, for example, the fibrous mass structure 12 has different rates of degradation throughout the cross section thereof to promote tissue ingrowth.

Figure 14:
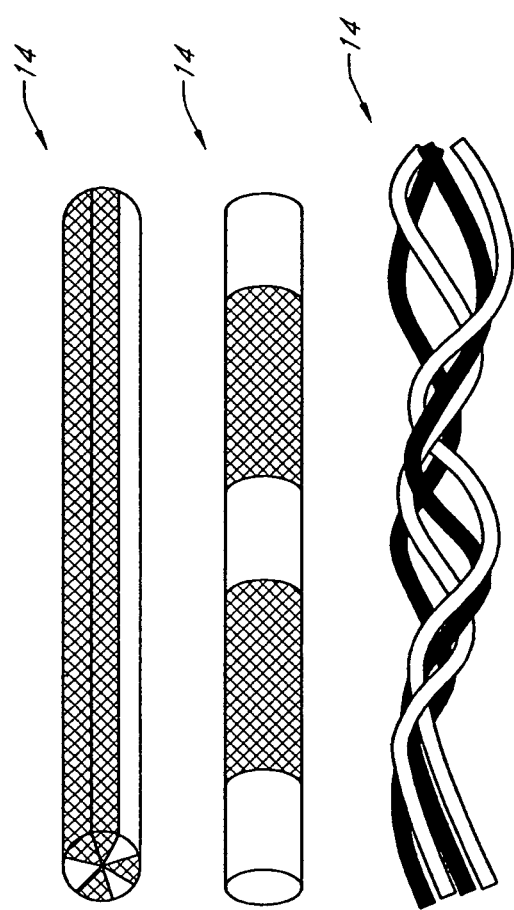
FIG. 14 illustrates fibers for use in a fibrous mass structure.

In some embodiments, as shown in FIG. 14, multiple materials can be combined to produce a fiber 14 having a customized degradation profile. The degradation rate of a particular fiber 14 can be different along different portions of the fiber. Additionally, the degradation rate of the implant 10 can be different along different portions of the implant 10. In one embodiment, a particular fiber 14 has a first portion, for example, along about 25% of the length of the fiber, having a relatively slower degradation rate and a second portion, for example, along about 75% of the length of the fiber, having a relatively faster degradation rate. In one embodiment, the first portion degrades more slowly that the second portion, so that the first portion acts like a plug to prevent blood flow in the hollow anatomical structure 20. In another embodiment, the center-most fibers may be comprised of a different material than the outer-most fibers, thereby causing a differential absorption rate through the radial dimension. In some embodiments, multiple materials can be coextruded to form fibers 14 having desired characteristics, as shown in the upper view of FIG. 14. In some embodiments, multiple materials can be sequentially extruded to form fibers 14 having desired characteristics, as shown in the middle view of FIG. 14. In some embodiments, multiple materials can be stranded together to form fibers 14 having desired characteristics, as shown in the lower view of FIG. 14.

Figure 15:
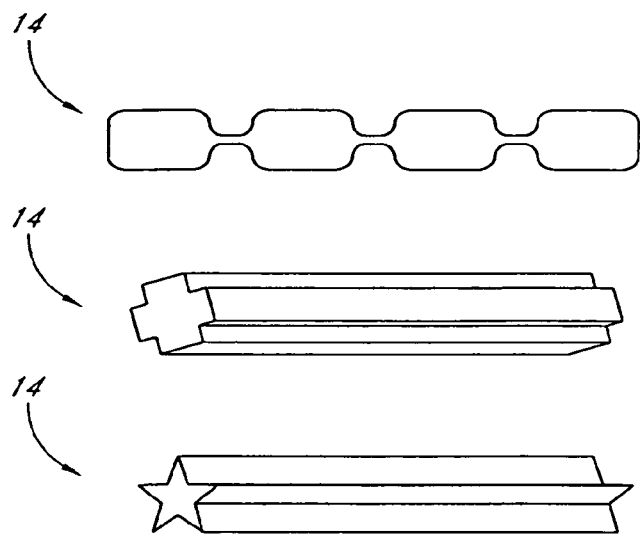
FIG. 15 illustrates fibers for use in a fibrous mass structure.
Figure 16:
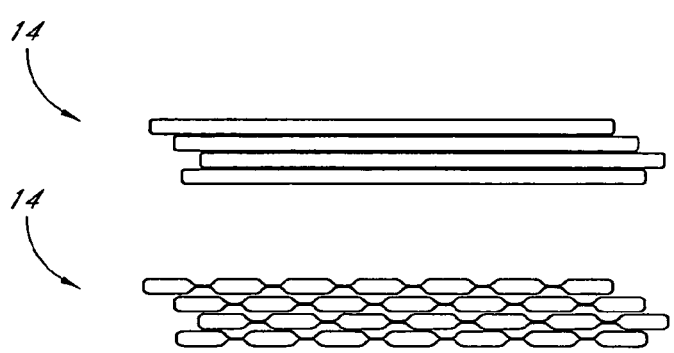
FIG. 16 illustrates fibers for use in a fibrous mass structure.
Figure 17:
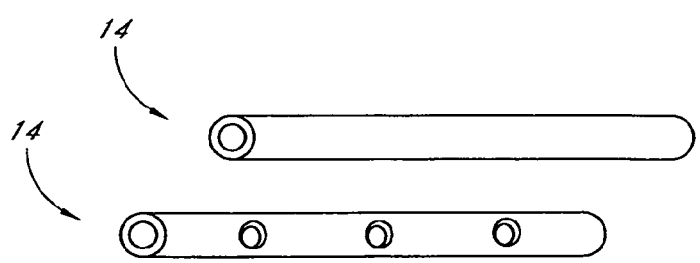
FIG. 17 illustrates fibers for use in a fibrous mass structure.

In some embodiments, as shown in FIG. 15, fibers 14 can have variable cross sections to accelerate degradation while retaining a constant fiber outer diameter. Some variable thickness strands 14 comprise areas with small cross-sections that degrade quickly, as shown in the upper view of FIG. 15. Some strands 14 having non-circular cross sections have an increased surface area to volume ratio to speed degradation, as shown in the middle and lower views of FIG. 15. Variable thickness strands also keep structures porous and open to provide scaffolding even when multiple fibers are positioned near each other. As shown in FIG. 16, in some embodiments there are no gaps between the strands 14 when packed together, while in other embodiments there are gaps between variable thickness strands 14 even when they are packed together. Additionally, as shown in FIG. 17, in some embodiments hollow fibers 14 are used. Hollow fibers 14 wick blood into the fiber, allowing for more surface area contact leading to faster degradation. Additionally, perforations along the length of the fiber 14 can be used in some embodiments, especially if the desired fiber length is longer than the distance that blood can travel by capillary action alone.

In some embodiments an implant 10 can comprise a multi-material yarn. In one embodiment, a bicomponent fiber can be used. Some U.S. bicomponent fiber producers include: BASF Corporation; DuPont Company; Fiber Innovation Technology, Inc.; KoSa; and Solutia Inc. A bicomponent fiber is comprised of two polymers of different chemical and/or physical properties extruded from the same spinneret with both polymers within the same filament or fiber. Some advantages, capabilities, and properties of bicomponent fibers include: thermal bonding; self bulking; very fine fibers; unique cross-sections; and the functionality of special polymers or additives at reduced cost. Most commercially available bicomponent fibers are configured in a sheath/core, side-by-side, or eccentric sheath/core arrangement. Bicomponent fibers can advantageously provide for variable degradation rates of a fibrous mass structure 12. Self bulking bicomponent fibers are created most often with side-by-side or eccentric cross sections. The variation in orientation across the fiber causes crimping due to differential shrinkage or strain with applied heat or relaxation.

Continuous Feed Delivery Systems

In some embodiments, a system for treating a hollow anatomical structure comprises a bioabsorbable fibrous implant (such as one or more of the embodiments shown in FIGS. 2-13) sized for insertion into the hollow anatomical structure. A continuous feed mechanism can be configured or employed to deliver the implant into the hollow anatomical structure.

FIGS. 18-23 illustrate embodiments of continuous feed hollow anatomical structure occlusion systems 200. The embodiments of FIGS. 18-23 generally involve structures capable of continuously delivering sections of a fibrous mass structure 210 into a hollow anatomical structure 220, thereby allowing substantially larger veins and/or longer sections of a hollow anatomical structure to be occluded with a fibrous mass structure 210.

The fibrous mass structure 210 used in connection with a continuous feed hollow anatomical structure occlusion system can include any suitable fibrous occlusive structure, such as those described elsewhere herein. For example, the fibrous mass structure can comprise a plurality of fibers of bioresorbable or other materials. In some embodiments, the fibers can be loosely arranged such that they can be "scrunched" to form masses of higher density fibrous structures. In alternative embodiments, the fibrous mass structure may include a plurality of knots or other relatively high density masses positioned at intervals along the elongate structure. In some embodiments, the elongate fibrous mass structure can have an un-compressed length that is longer than a delivery device. For example, in some embodiments the fibrous mass structure can have an un-compressed length between about 1 m and about 30 m, and in one particular embodiment, the fibrous mass structure has an un-compressed length of about 3 m. In an implanted state, a fibrous mass structure is typically compressed to occupy a substantially shorter length and smaller volume than in a loose uncompressed state. Post-implantation the fibrous mass structure can have a compressed length within the hollow anatomical structure between about 5 cm or less to about 30 cm or more, in some embodiments from 10 cm or less to 20 cm or more.

FIGS. 18-23 illustrate embodiments of a continuous feed hollow anatomical structure occlusion system comprising a continuous length of a fibrous mass 210 and an axially reciprocating delivery member 230 within an outer sheath 232. The axially reciprocating member 230 is generally configured to eject portions of the fibrous mass 210 from the distal end 240 of the outer sheath 232. The axially reciprocating member 230 is generally configured to engage the fibrous mass 210 as the reciprocating member 230 moves in the distal direction relative to the outer sheath 232, thereby ejecting a segment of the elongate fibrous mass 210 out the distal end 240 of the sheath 232. In some embodiments, the axially reciprocating member 230 is further configured to disengage the fibrous mass structure 210 as the member 230 moves in the proximal direction, thereby allowing the reciprocating member 230 to move proximally relative to the sheath 232 and fibrous mass 210 without pulling the fibrous mass 210 proximally.

Figure 18:
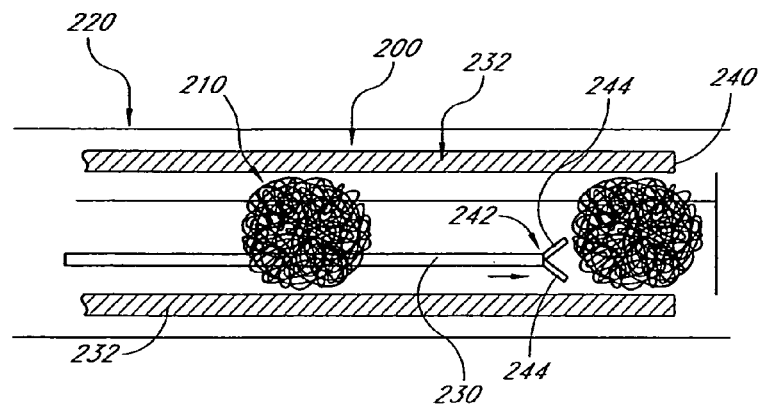
FIG. 18 is a schematic cross-sectional view of one embodiment of a continuous feed hollow anatomical structure occlusion system in a first position.
Figure 19:
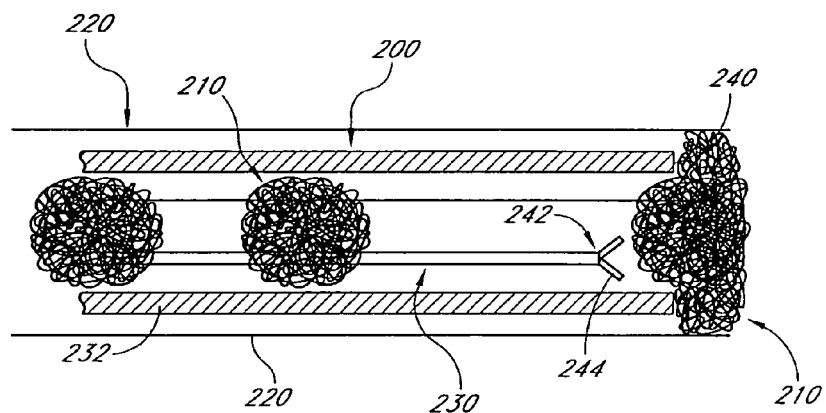
FIG. 19 is a schematic cross-sectional view of the system of FIG. 18 in a second position, a first segment of fibrous mass structure having been deployed.
Figure 20:
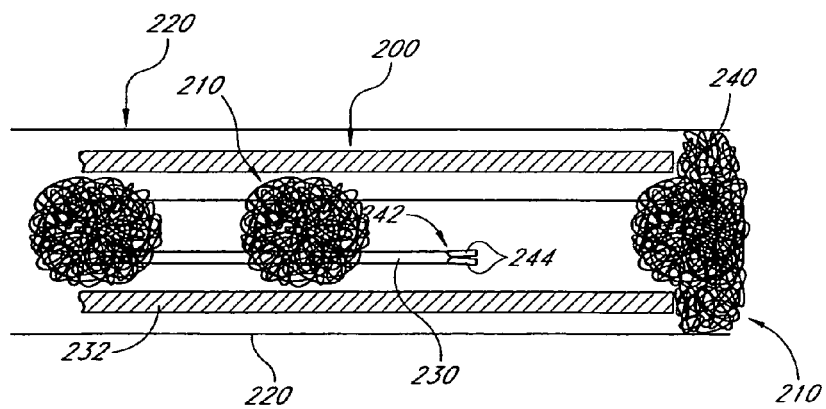
FIG. 20 is a schematic cross-sectional view of the system of FIG. 18 in a third position, illustrating the retraction of a pusher rod.

In one embodiment, illustrated for example in FIGS. 18-20, the reciprocating member 230 comprises an elongate push rod positioned within the outer sheath 232 and alongside the elongate fibrous mass structure 210. The reciprocating member 230 of this embodiment can comprise a distal pusher head 242 that is movable between a first position in which the head 242 engages the fibrous mass 210, and a second position in which the head 242 disengages the fibrous mass 210 during proximal movement of the push rod 230.

In the embodiment of FIGS. 18-20, the push rod comprises a material and construction with a sufficient column strength to transfer an axial force applied at the proximal end of the rod to the fibrous mass structure 210 via the pusher head 242 at the distal end of the rod. The push rod is also preferably sufficiently flexible to allow the entire device to be navigated through a patient's vasculature to a desired delivery site.

Figure 21:
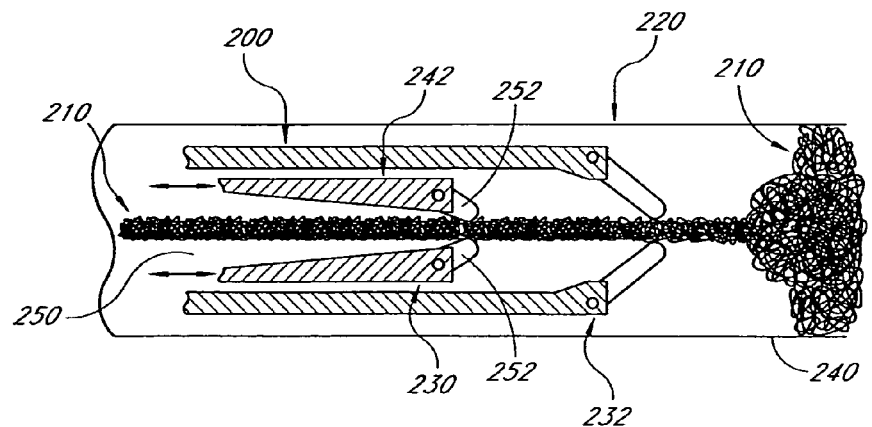
FIG. 21 is a schematic cross-sectional view of an alternative embodiment of a continuous feed hollow anatomical structure occlusion system.

In the embodiment illustrated in FIG. 21, the pusher head 242 comprises a pair of hinged legs 244 configured to pivot between a first (open) position, and a second (closed) position. In one embodiment, the legs 244 are biased outwards by a spring or other resilient biasing member. In such an embodiment, the biasing force is preferably sufficiently small that the legs deflect towards the second position as the push rod is pulled proximally relative to the fibrous mass structure 210. In an alternative embodiment, the legs 244 can be manually moved between the first and second positions by an actuation member, such as a pull and/or push wire.

In another embodiment, a pusher head can include a plurality of legs made of a rigid, resilient material. The legs can be biased radially outwards toward a first, expanded position in which the legs engage the elongate fibrous mass structure. The legs can further include a sufficiently small biasing force that they disengage the fibrous mass structure as the rod is pulled proximally. In still another embodiment, a pusher head can be provided with a single radially expandable and contractible member configured to engage the fibrous mass structure on distal movement of the reciprocating member. And in still another embodiment, a pusher head can be made of a rigid material. The legs can be fork or "V" shaped to engage the fibers as the fork is pushed forward to deliver the fibrous mass structure and does not engage the fibers as the fork is pulled relative to the delivered fibrous mass structure. A multitude of pusher head shapes can be envisioned and are within the scope of this invention.

Figure 22:
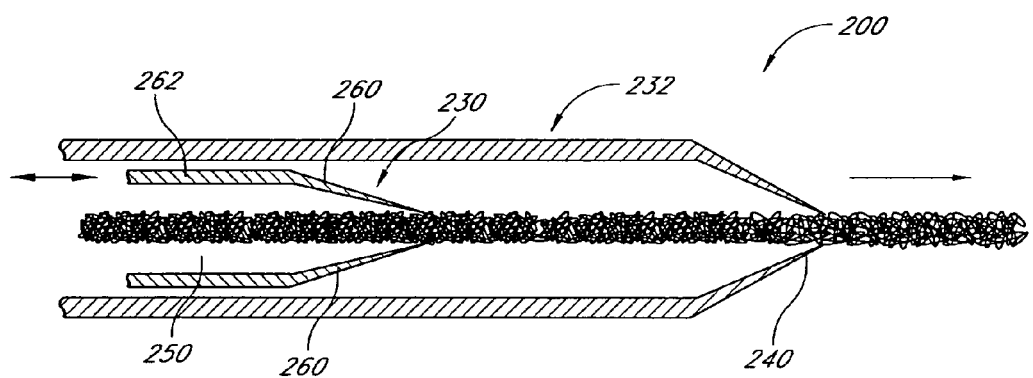
FIG. 22 is a schematic cross-sectional view of an alternative embodiment of a continuous feed hollow anatomical structure occlusion system.
Figure 23:
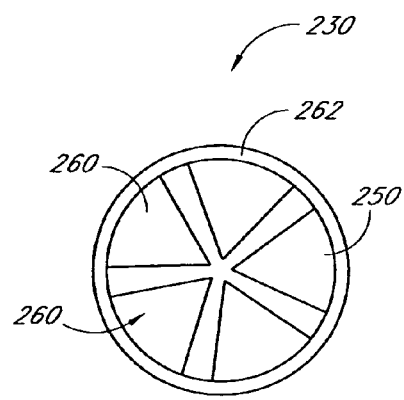
FIG. 23 is a distal elevation view of a distal end of the inner sheath of the device of FIG. 22.

FIGS. 21-23 illustrate alternative embodiments of a continuous-feed hollow anatomical structure occlusion system. In the embodiments of FIGS. 21-23, the axially-reciprocating member 230 comprises an internal lumen 250 through which the elongate fibrous mass structure 210 extends. The axially reciprocating members 230 of these embodiments also preferably include distal pusher heads 242 configured to push the fibrous mass structure 210 distally as the reciprocating member 230 is moved distally relative to the outer sheath 230. As in the previous embodiments, the pusher heads 230 are preferably configured to disengage the fibrous mass structure 210 as the head 230 is moved proximally relative to the outer sheath 232 and the fibrous mass structure.

In the embodiment of FIG. 21, the pusher head 230 comprises a pair of hinged gripper members 252. In alternative embodiments, a pusher head may comprise anywhere from one to four or more gripper members. Each of the gripper members 252 is resiliently biased inward in order to pinch the fibrous mass structure extending between the grippers 252. The gripper members 252 are preferably configured such that the friction between the gripper members 252 and the elongate fibrous structure 210 is sufficient to cause the gripper members 252 to pivot inwards, thereby gripping the fibrous structure 210 on distal movement of the reciprocating member 230. The gripper members 252 are also preferably configured to disengage the fibrous structure 210 on proximal movement of the reciprocating member 230. These characteristics can be achieved by providing teeth on the gripper members 252 or by varying a length and/or bias force of the gripping members 252.

The embodiment of FIGS. 22 and 23 comprises a pusher head 230 having a plurality of claws 260 extending from the distal end of an inner sheath 262. The claws 260 are generally biased radially inwards such that they will pinch the fibrous mass, particularly during movement of the inner sheath 262 in the distal direction. The claws 260 can be formed by cutting a cylindrical section of tubing to form pointed segments. The claws 260 can then be bent inwards in order to engage the fibrous mass 210. In alternative embodiments, the distal section of the inner sheath can include a section of reducing diameter, such as a conically shaped section with a distal opening sized to allow a fibrous mass to be pulled therethrough in the distal direction, but preventing the fibrous mass from being pushed proximally into the distal opening. In other embodiments, the outer sheath 232 can also comprise the plurality of claws 260 extending from the distal end of the outer sheath 232 or alternatively may be comprised of a resilient polymeric material of cone shape and reduced diameter at its distal end, a heat formed polymeric duck-bill shape, or machined metallic claw feature. A multitude of alternative embodiments can be envisioned and are within the scope of this invention.

Figure 24:
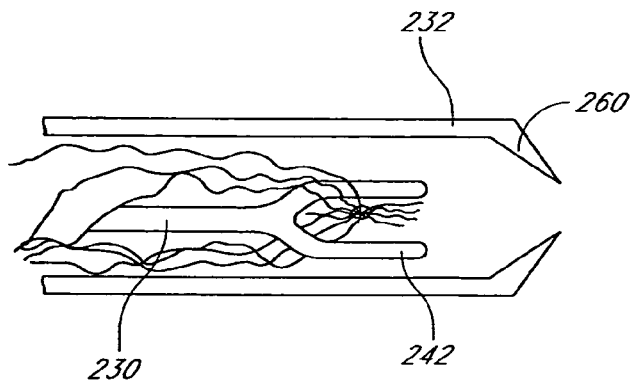
FIGS. 24-26 illustrate a continuous feed hollow anatomical structure occlusion system.
Figure 25:
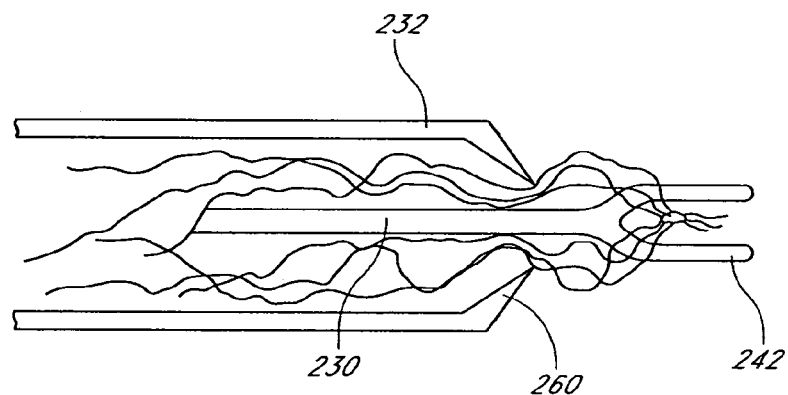
Figure 26:
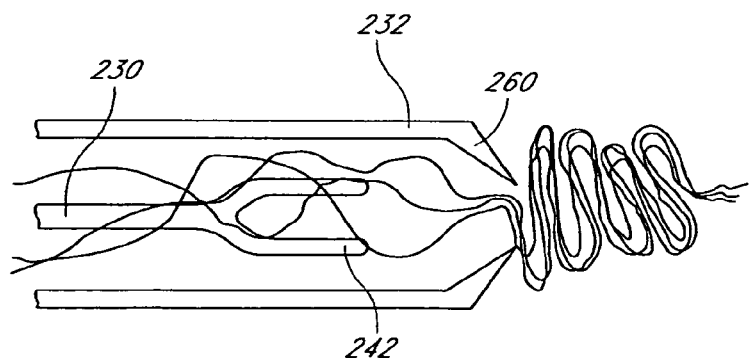

The embodiment of FIGS. 24-26 comprises a reciprocating member 230 with a rigid fork shaped pusher head 242 used to deliver the fibrous mass structure 210. The pusher head 242 engages the distal end of the fibrous mass structure 210 and forces it past the claws 260 on the outer sheath 232 as shown in FIG. 25. This interaction preferentially delivers a portion of the fibrous mass structure into the hollow anatomical structure. The reciprocating member 230 is then retracted and disengages from the fibrous mass structure 210. In this embodiment, any reverse movement of the fibrous mass structure 210 back into the outer sheath 232 is prevented by the claws 260. This action also allows the pusher head 242 to fully disengage from the fibrous mass structure 210 as it is delivered as shown in FIG. 26. The reciprocating member 230 is again actuated forward, the pusher head 242 again engages the fibrous mass structure 210 in a different location along its length and delivers more fibrous mass structure 210 out the outer sheath 232 and into the hollow anatomical structure. This cycle is repeated continuously until the desired quantity of fibrous mass structure is delivered or the desired treatment length is achieved.

In some embodiments, it is desirable to temporarily hold the fibrous mass 210 substantially stationary in order to prevent the axially reciprocating member 230 from pulling the fibrous mass proximally during proximal movement of the axially reciprocating member 230. In some embodiments, the fibrous mass may be held against movement in the proximal direction by simply abutting the distal edge of the outer sheath after having been ejected from the sheath 232 as shown in FIG. 19. In alternative embodiments, the outer sheath can include a plurality of claws or a section of reducing diameter or other structures similar to the pusher heads described above.

Figure 27A:
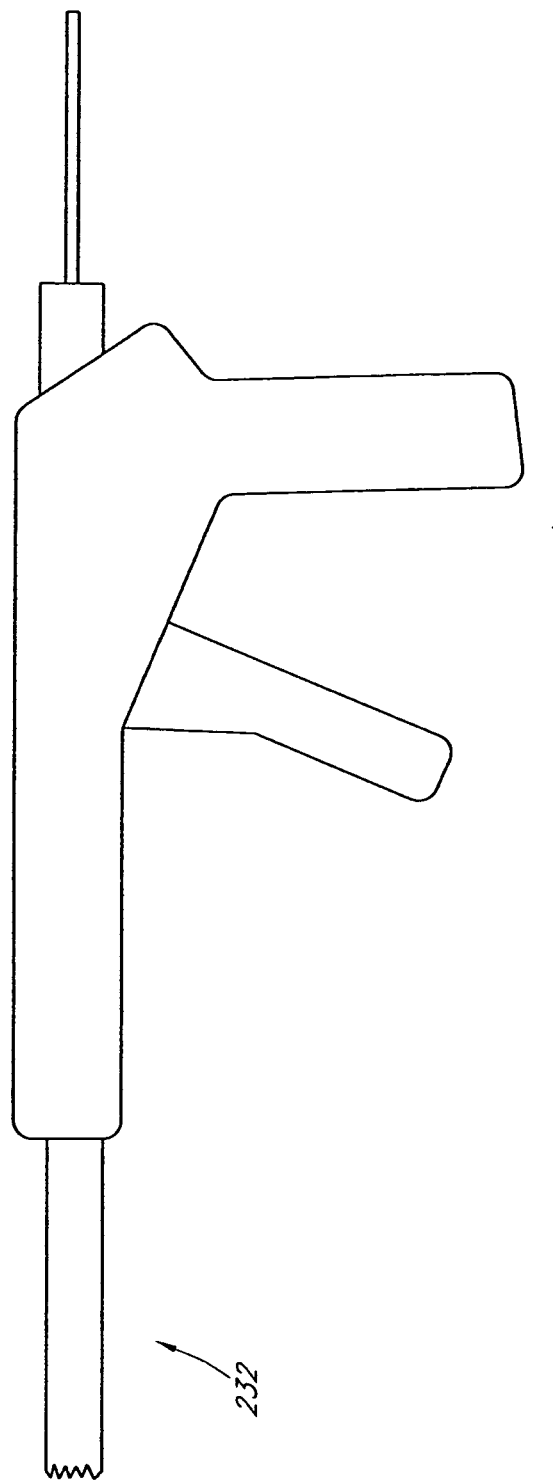
FIGS. 27a-27c illustrate a pistol grip handle used for delivery of a fibrous mass structure.
Figure 27B:
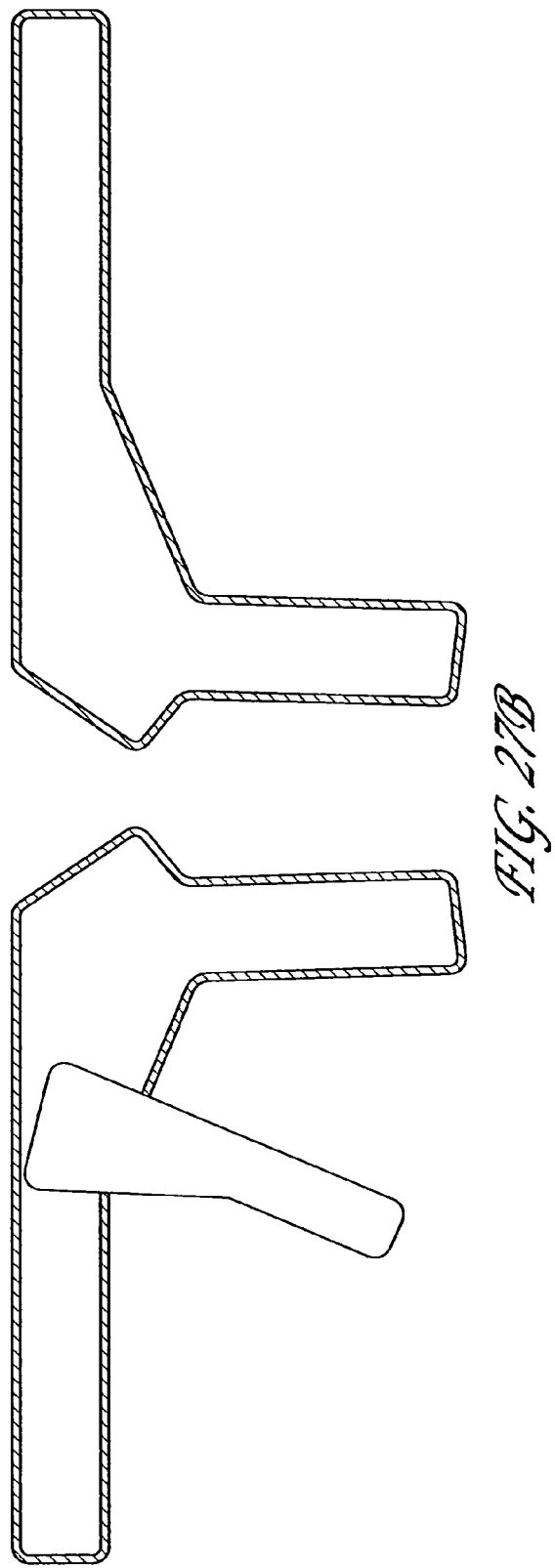
Figure 27C:
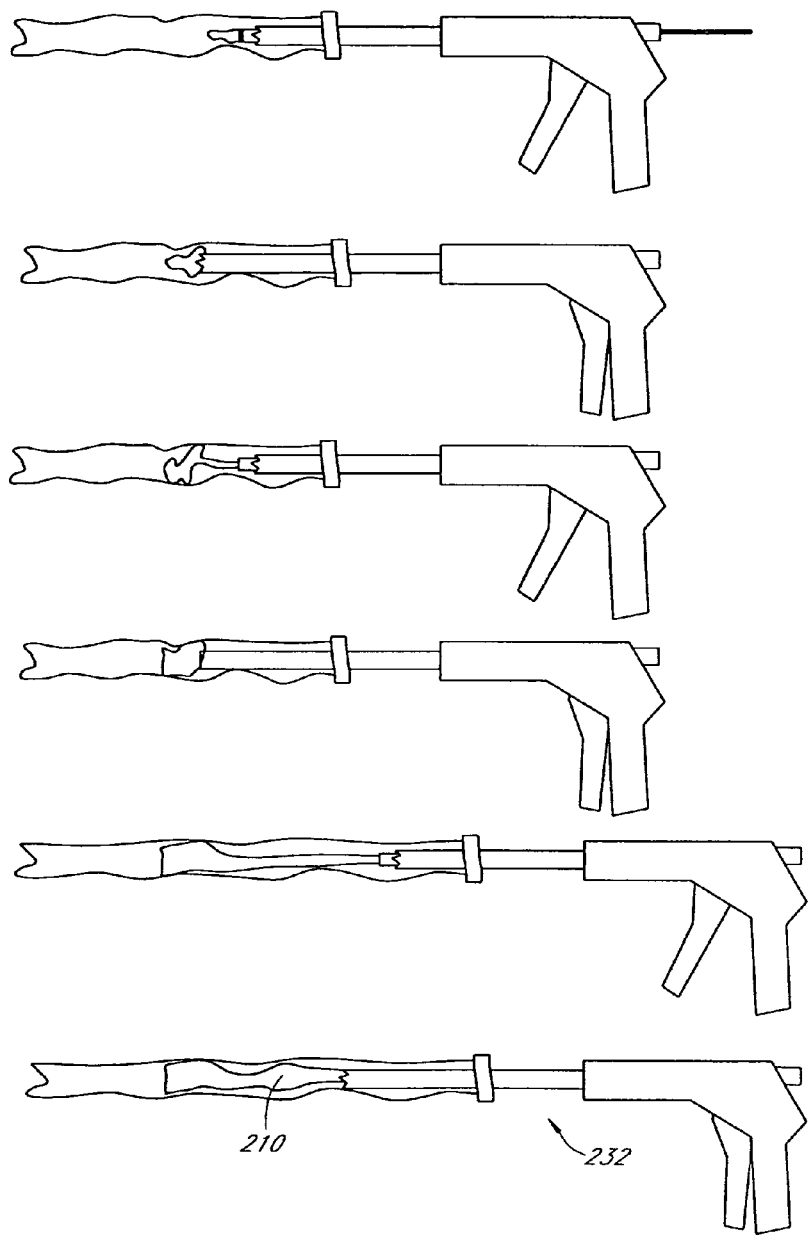

In some embodiments, it is desirable to associate the reciprocating member 230 and the outer sheath 232 with an automated or manual pistol grip handle allowing for single handed, easy and continuous delivery of the fibrous mass structure 210 as shown if FIGS. 27a-27c. As shown in FIG. 27c, first, a push rod is used to get the implant material started. Then the handle is actuated to engage and advance the implant material. Then the handle is released leaving the implant material dispensed into the hollow anatomical structure. Then, the handle is actuated again, packing more implant material into the same location. Then, the handle is released only partially. If the friction between the implant material already deployed and the hollow anatomical structure wall is sufficient, additional material will be deposited. Manual compression may also be used to keep the implant material from going backward with the handle. Then, the handle is actuated again, and implant material is deposited along the vein tract. This can be repeated until desired treatment length is filled.

Figure 28:
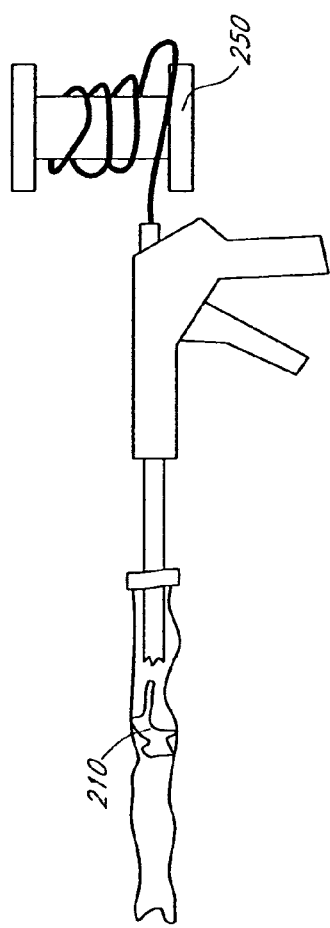
FIG. 28 illustrate the pistol grip handle with the fibrous mass structure on a coil.

In an additional embodiment, for fibrous mass structures 210 longer than the outer sheath 232, the fibrous mass structure 210 may be coiled onto a spool 250 or contained in a cartridge (not shown) and configured to feed off the spool 250 or cartridge into the proximal end of the outer sheath 232 as the distal end of the fibrous mass structure 210 is continuously advanced into the hollow anatomical structure as shown in FIG. 28.

In an alternative embodiment, the fibrous mass can be deployed into the vessel using a small volume stream of compressed gas (e.g. $CO_2$) to eject the material into vessel, thereby obviating the need for a push rod.

Figure 29:
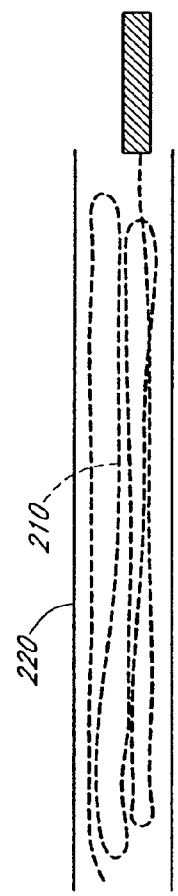
FIG. 29 illustrates an overlapping delivery configuration of the fibrous mass structure.

In another embodiment, the fibrous mass structure 210 can be introduced in a long overlapping manner rather than short packed segments. In such embodiments, the fibrous mass structure 210 is delivered along the entire treatment length while the entire catheter assembly is retracted. The entire catheter assembly is then advanced forward and another segment of fibrous mass structure 210 is delivered along the entire treatment length. This cycle can be repeated to deliver the fibrous mass structure 210 over a long treatment length. One embodiment of such an over-lapping deployment system is shown in FIG. 29.

Figure 30:
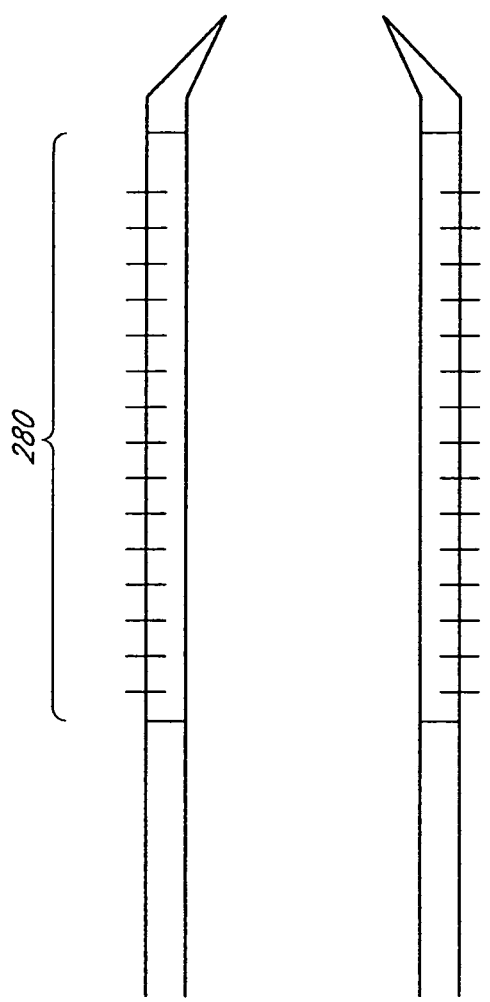
FIG. 30 illustrates a scraping end of a delivery sheath.

As shown in FIG. 30, in still another embodiment, the outside of the outer sheath 232 can also include a scraping portion 280 at the distal end extending a length of 2 cm or less to 10 cm or more that acts to brush and scrape the intimal lining of the vessel as the catheter is advanced to the treatment site. This effectively denudes and disrupts the endothelial cells lining the vessel as well as the internal elastic lamina within the intima of the vessel. This combination allows for simultaneous denudation of the intimal lining of the vessel as the catheter carrying the fibrous mass structure 210 is advanced to the treatment site, obviating any need for an additional separate step to injure the intima of the vessel prior to deploying the fibrous mass structure. Disrupting the intimal structure of the vessel allows for a more durable occlusion by allowing for improved tissue in-growth and integration of the fibrous mass structure to the vessel wall during the coagulation cascade and body healing process. Alternatives for implementing the scraping portion 280 include but are not limited to: bristle brush elements extending from the catheter; a simple scuffed surface formed by, e.g., beadblasting; an etched surface; micromachined miniature cutting blades; a polymeric raised flap; specially designed and separate machined component associated with the outer sheath surface, etc.

Figure 31:
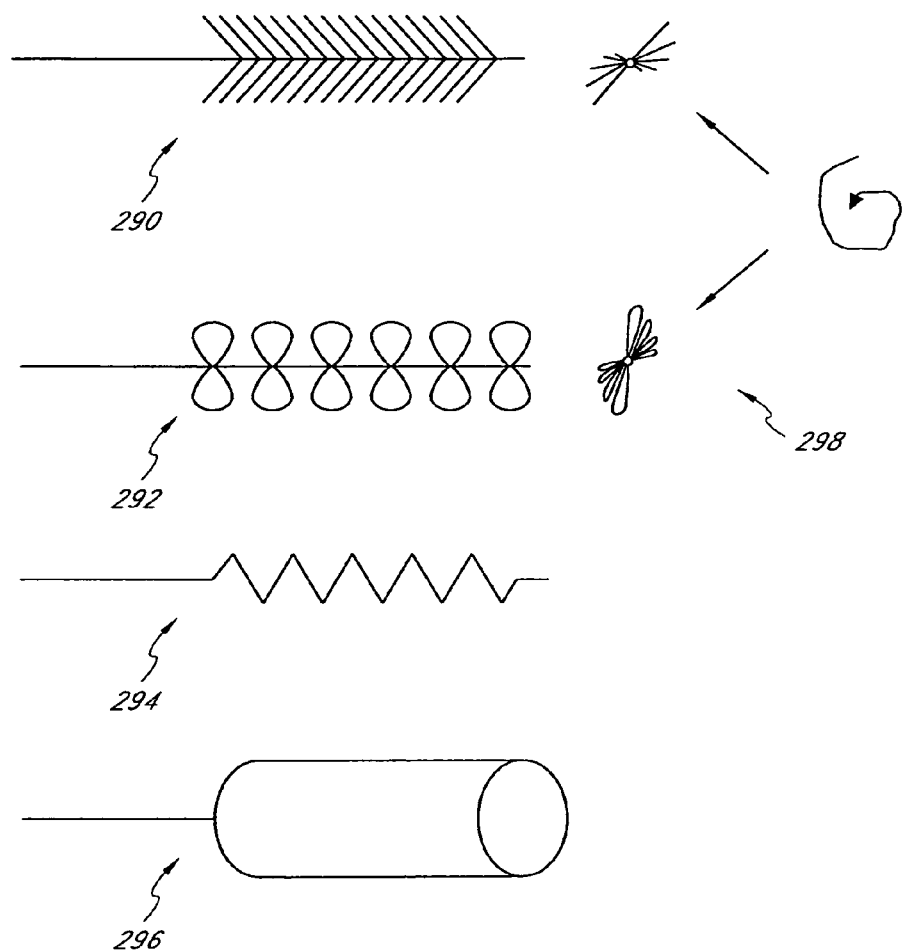
FIG. 31 illustrates several abrasive elements for contacting an inner surface of a hollow anatomical structure.
Figure 32:
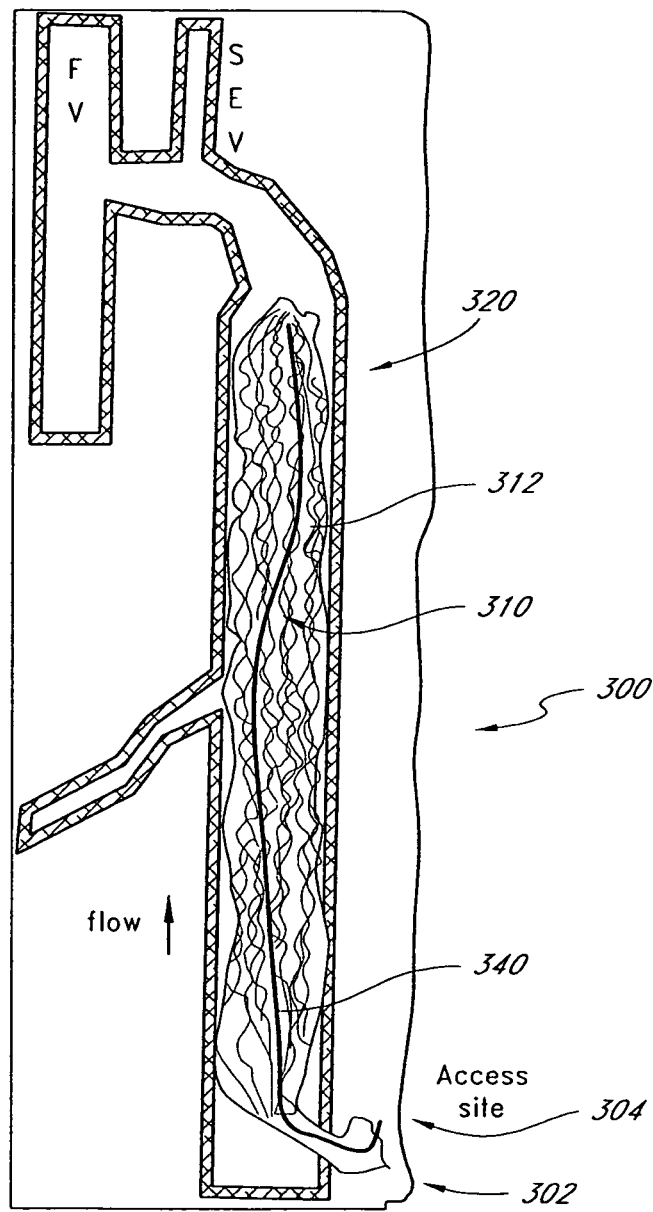
FIGS. 32-35 illustrate one method of fixation of an implant at an access site location according to one embodiment.

As shown in FIG. 31, in some embodiments, an abrasive surface can be provided on a sheath, a catheter, a tool, a scraper and/or an implant to engage a surface of a hollow anatomical structure. In some embodiments, the abrasive surface can comprise a brush and/or a rasp. According to one technique, during delivery of an implant, the surface of a hollow anatomical structure can be engaged by the abrasive surface for endothelial denudation to set up better biologic occlusion. For example, a brush like component could be attached to the outer surface of the delivery system or a separate brush can be used prior to implant delivery. The purpose of the brush is denuding the endothelial cells that line the lumen and disrupting vessel internal elastic lamina. Both actions improve tissue in-growth and fixation in the chronic phase. The brush material can be left in place as an occluder in some embodiments. The brush can be made out of bioabsorbable materials or from non-absorbable materials. As shown in FIG. 31, in some embodiments, the abrasive surface can comprise one or more of a fishbone configuration 290, a propeller configuration 292, a zig-zag configuration 294, a sponge and/or foam brush configuration 296, and one or more bristles configured to wrap around a shaft in a secondary spiral shape 298.

Termination and Fixation

With reference to FIGS. 32-57C, according to some embodiments, an apparatus 300 for treating a hollow anatomical structure 320 comprises a bioabsorbable fibrous body 312. A fixation member 302 is associated with the body 312 and configured to limit migration of the body 312 when implanted in the hollow anatomical structure 320. According to one aspect of the embodiments, the fixation member 302 comprises a tether 340. According to another aspect of the embodiments, the fixation member 302 comprises an anchor 360. According to another aspect of the embodiments, the fixation member comprises an expandable element 380. According to another aspect of the embodiments, the fixation member comprises a braid 382. These and other embodiments, methods, techniques and aspects are described further herein.

In some embodiments, implants 310 are configured to be securely positioned within a hollow anatomical structure 320. Fixation within a hollow anatomical structure 320 can reduce the likelihood of implant migration. Several fixation techniques and structures are described in more detail below. Other suitable fixation techniques and structures can also be used to limit implant migration. In one embodiment, a bioresorbable occlusive scaffold implant 310 is configured for delivery through a catheter, e.g., an 8 F catheter. In some embodiments, the bioresorbable occlusive scaffold implant 310 is preferably supplied in a length long enough to provide sufficient material to treat the hollow anatomical structure 320 along the entire desired implantation length and to allow for excess material of the scaffold implant to be trimmed away. According to one fixation technique described further below, the scaffold implant 310 can be cut off at the skin surface near the access site 304. A portion of the scaffold implant 310 can be tucked under the skin if desired. In some embodiments, a tether 340 preferably is coupled with the scaffold implant 310 at a distal portion of the scaffold 310. The tether 340 preferably extends through the access site 304 and is secured to the patient's skin near the access site 304.

Fixation Methods

According to one technique, a method of treating a hollow anatomical structure comprises implanting a bioabsorbable fibrous body 312 in a hollow anatomical structure 320 and securing the body 312 in the hollow anatomical structure 320 to limit migration of the body 312 within the hollow anatomical structure 320. According to one aspect of the technique, securing the body 312 comprises anchoring the body 312 at an access site 304 of the hollow anatomical structure 320. According to another aspect of the technique, securing the body 312 comprises implanting an expandable anchor 380 near the body 312 in the hollow anatomical structure 320. According to another aspect of the technique, securing the body 312 comprises thermally shrinking the hollow anatomical structure 320 near an implant location in the hollow anatomical structure 320. Implanting the body 312 preferably comprises implanting the body at the implant location. According to another aspect of the technique, securing the body 312 comprises securing the body 312 with a fenestration anchor 360. According to another aspect of the technique, securing the body 312 comprises anchoring the body at a percutaneous retrograde access site 306. These and additional aspects, techniques, methods, and embodiments are described in more detail below.

Access Site Anchor

Figure 33:
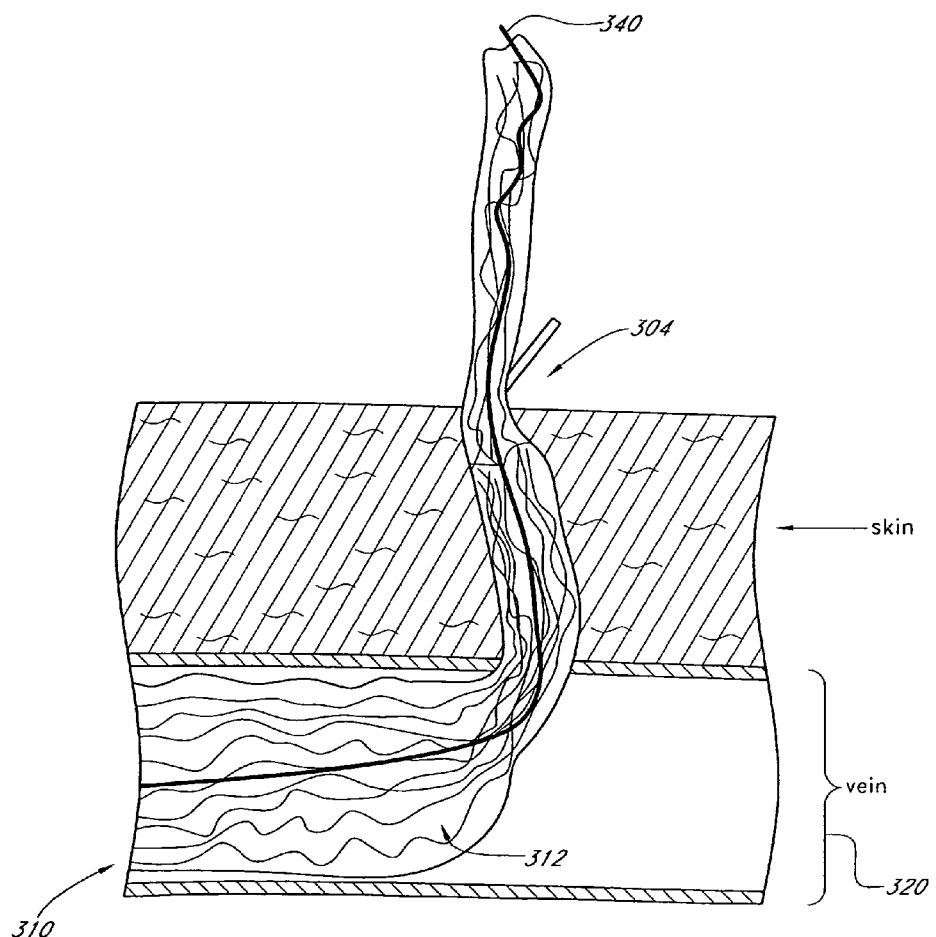
Figure 34:
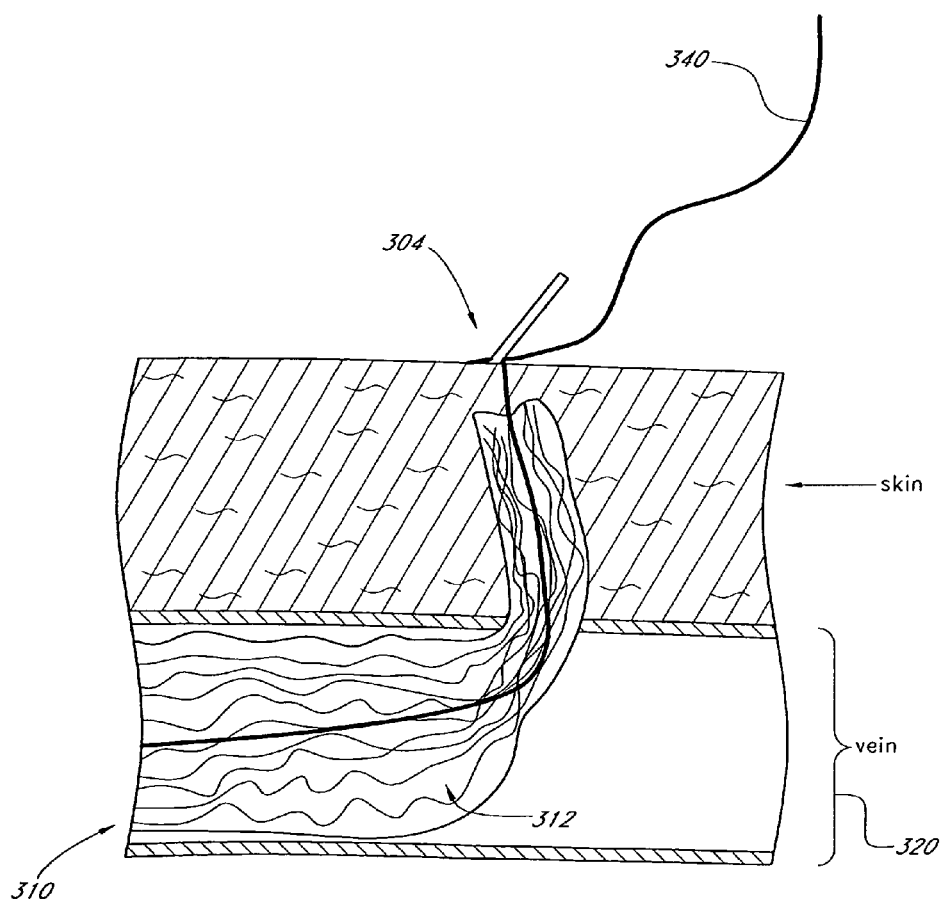
Figure 35:
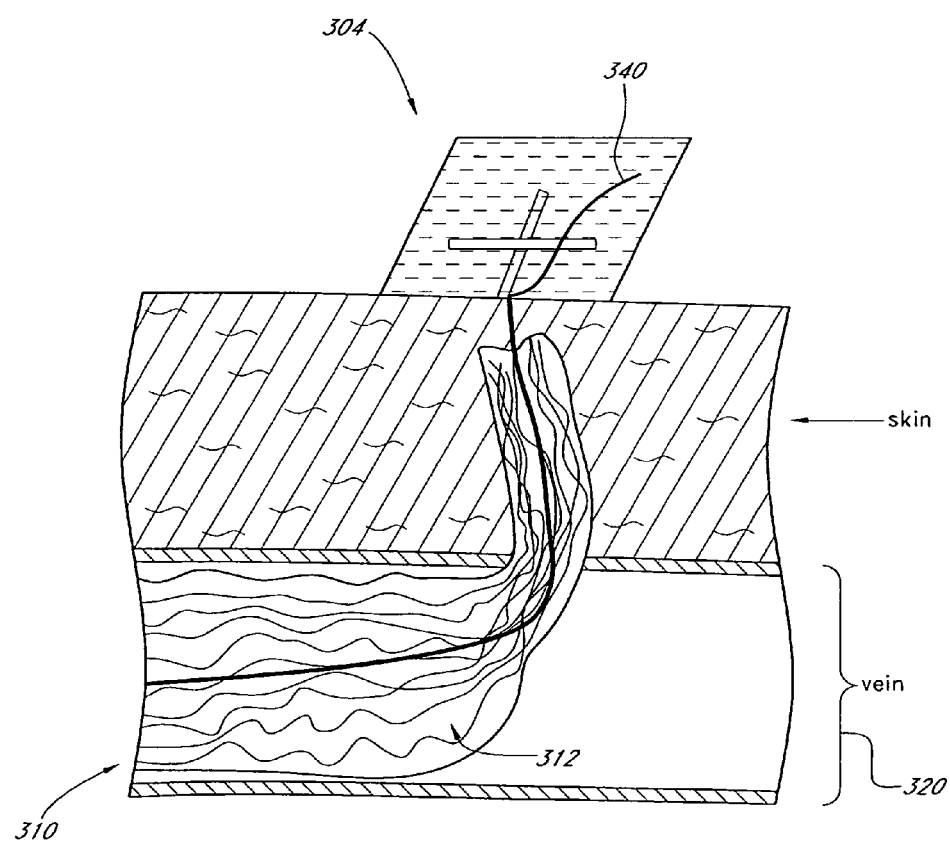
Figure 36:
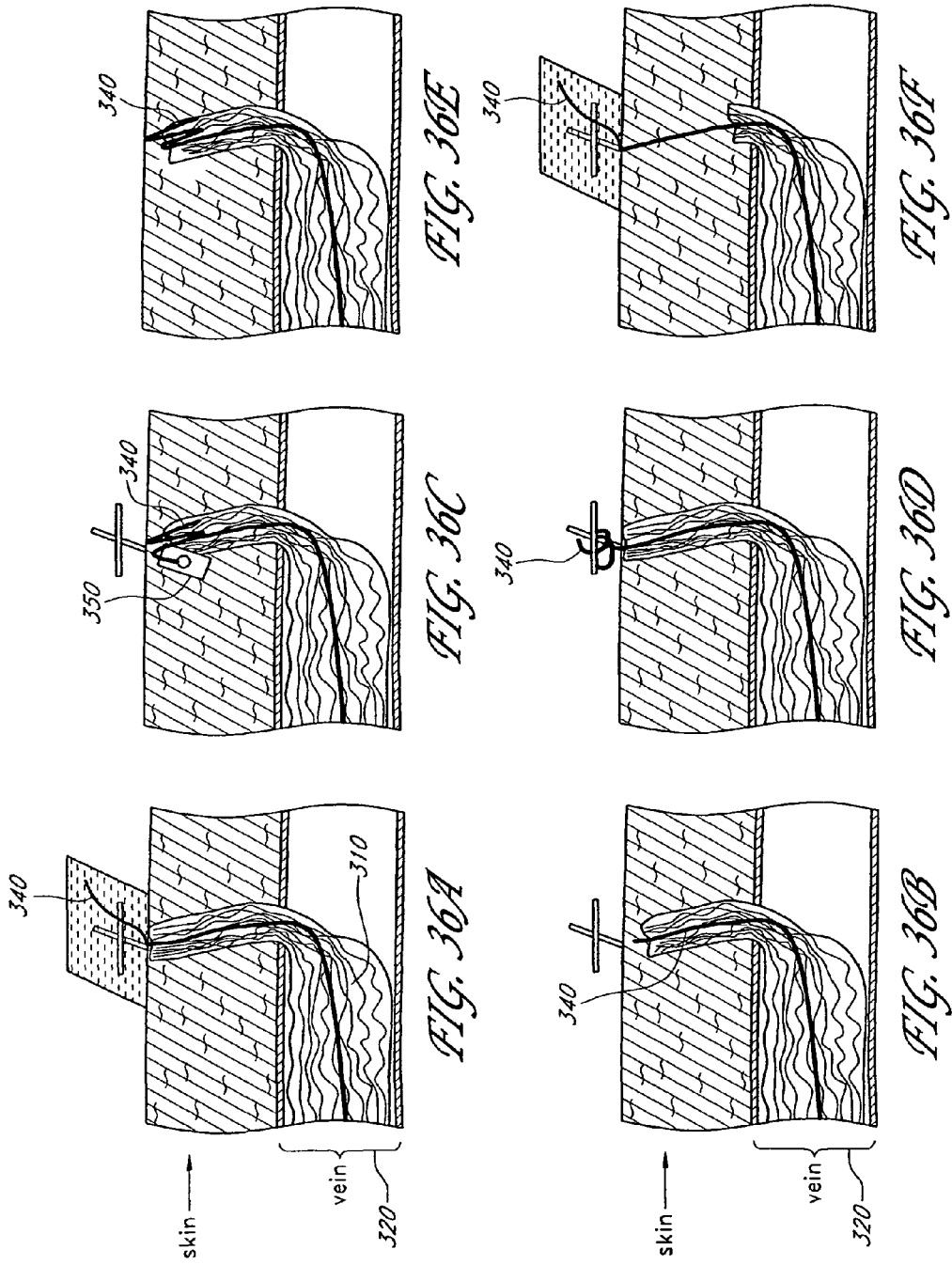
FIGS. 36A-F illustrate several alternative fixation techniques according to several embodiments.
Figure 37:
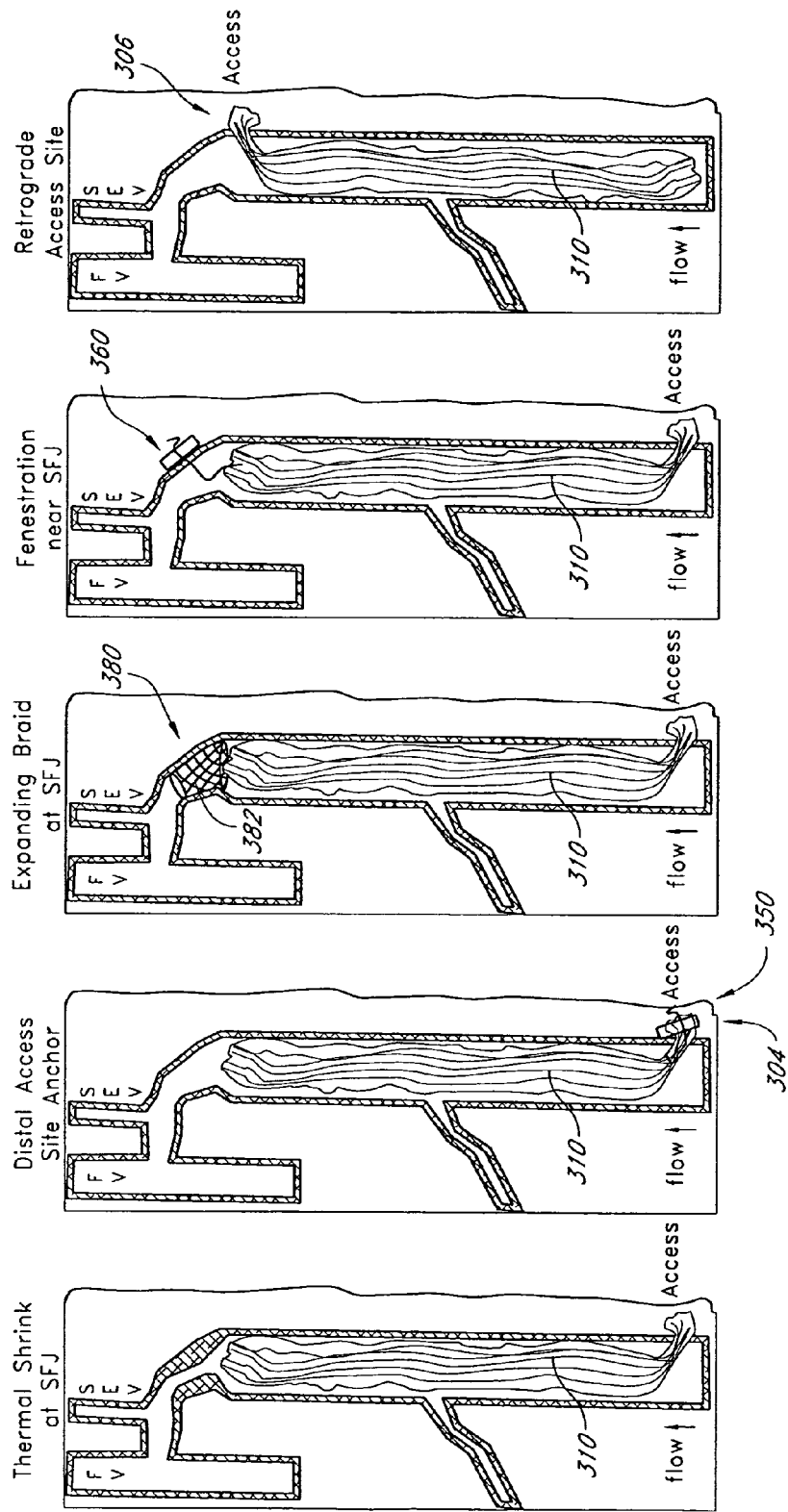
FIGS. 37A-E illustrate several alternative fixation methods according to several embodiments.

As stated above and as shown in FIGS. 32-36 and 37B, according to one aspect of the technique, securing the body 312 comprises anchoring the body 312 at an access site 304 of the hollow anatomical structure 320. According to another aspect of the technique, the method further comprises positioning the body 312 so that a portion of the body 312 extends out of the hollow anatomical structure 320 through the skin of the patient at an access site 304 on the skin, as shown in FIG. 33. According to another aspect of the technique, the body further comprises a tether 340, and the method further comprises trimming an end portion of the body 312 so that it is substantially flush with the skin and so that the tether 340 extends beyond the body 312 through the access site 304, as shown in FIG. 34. According to another aspect of the technique, the method further comprises securing the tether 340 near the access site 304, as shown in FIG. 35. These and other aspects, techniques, methods and embodiments are described further herein.

The hollow anatomical structure to be treated is preferably accessed at a site proximal to the segment to be treated using the Seldinger technique. An introducer sheath (preferably sized from 6F to 8F) is inserted at the site for use during implant delivery. According to this aspect, the implant 310 is coupled to the vein 320 at the access site 304. Several methods and structures for coupling the body 312 to the hollow anatomical structure 320 at the access site 304 are described herein.

According to one embodiment, a bioabsorbable full length fibrous mass structure 312 is configured to extend from near the sapheno-femoral junction through the vessel, across the access site 304, and terminate outside the body. An anchor string and/or tether 340 can run from a distal portion of the implant 310 proximally through a generally central portion of the implant 310 and can extend through the access site 304 and terminate outside the body when the implant 310 is positioned within a hollow anatomical structure 320 of the body. In some embodiments, the implant 310 itself preferably comprises any of the combinations disclosed herein. As described above, the fiber processing parameters preferably are selected to maximize fiber crimp retention which enhances the self expanding and/or volume filling properties of the implant 310. As described above, the implant 310 can be pre-folded over the tip of a pushrod and in some cases can be manually textured to entangle and create further bulk if necessary and/or desired. Termination outside the body can be performed by one or more active fixation techniques described herein or other suitable techniques to limit implant migration.

In some embodiments, an implant 310 comprises a tether string 340. The string 340 preferably is a multifilament string or a monofilament of a thicker cross section than the remainder of the implant, or braided suture material. In one embodiment, a first end portion of the string 340 is attached at a proximal end portion of the implant 310. In some embodiments, the string 340 is attached to the implant 310 at the distal end portion of the implant 310, and/or at a plurality of locations on the implant 310. A second end portion of the string 340 preferably is attached to the body tissue at the access site 304. According to one method of attachment, a knot is tied in the string 340 outside the wall of the hollow anatomical structure 320, as will be described in more detail below. The bulk of the knot preferably prevents the string 340 from sliding back though the wall of the hollow anatomical structure 320. For example, a knot, e.g., an overhand knot, can be tied in the free end of the tether string 340 to anchor the implant 310 at the access site 304. A blunt tool can be used to ensure that the knot tightens close to the exit point from the skin. Multiple knots can be formed. The end of the tether string 340 can be threaded into the tip of a knot pusher and/or a blunt cannula. The end of the string 340 can be pre-stiffened with cyanoacrylate to make threading the tether string easier. In some embodiments, Loctite 4061 can be used to pre-stiffen the tether string 340. A tether string 340 comprising a monofilament suture may or may not require stiffening in some embodiments. The knot pusher is advanced to the knot and then used to push the knot below the surface of the skin. The knot pusher is then removed. Accordingly, the knot is positioned outside the wall of the hollow anatomical structure 320, but below the skin surface. Excess tether string can be cut off just below the skin surface. Additional wound closure techniques can be used at the incision site, e.g., steri-strips and/or tissue adhesives.

Figure 38:
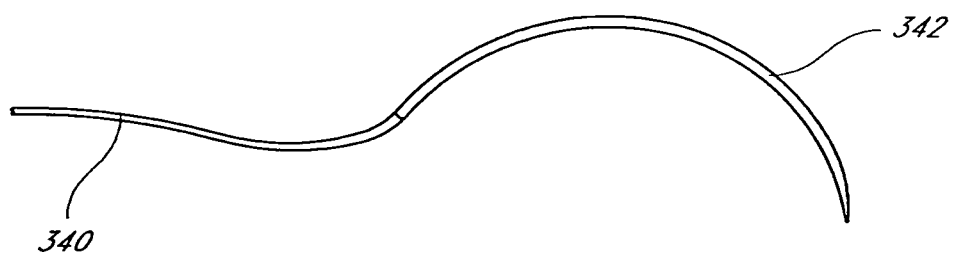
FIG. 38 illustrates a tether string comprising a needle point according to one embodiment.
Figure 39:
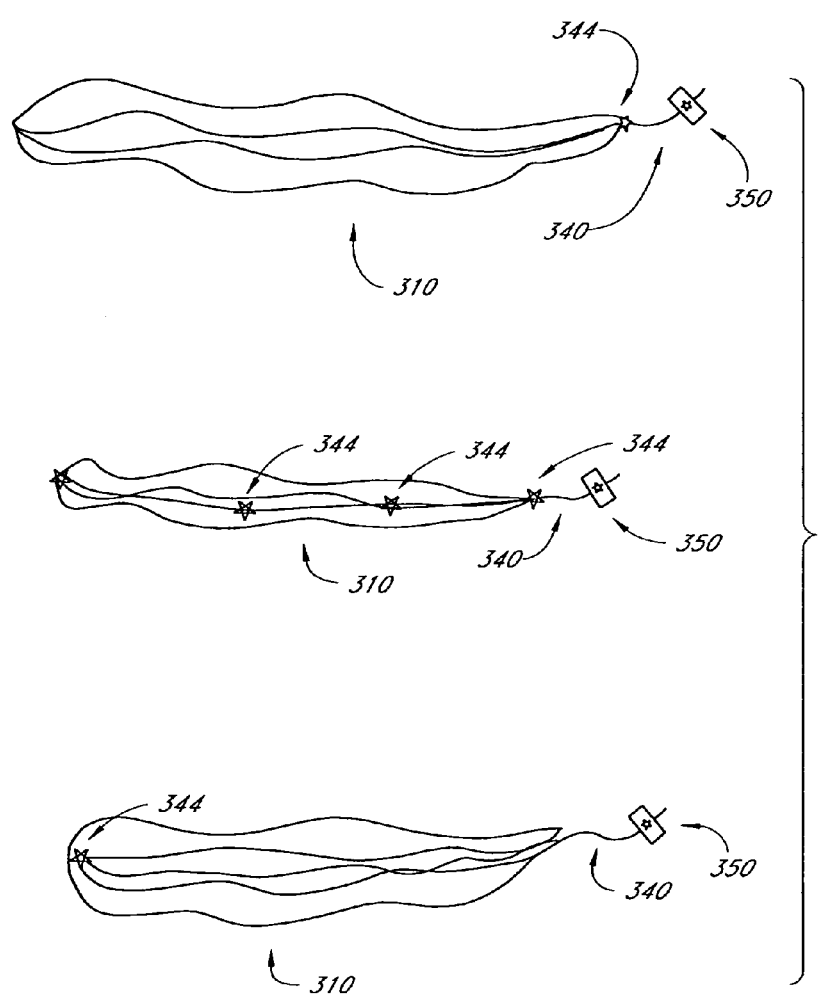
FIG. 39 illustrates a tether string coupled with an implant at one or more locations according to several embodiments.

According to another method of attachment, the string 340 can terminate in a needle 342, as shown in FIG. 38, or be coupled with a needle, e.g., threaded through a separate needle, and then tied or sutured to the subcutaneous tissue or to the skin. The knot can reside in the subcutaneous tissue outside the hollow anatomical structure 320 and absorb into the tissue over time. In some embodiments, the string 340 can be made of the same material as the implant 310. It is possible to attach a monofilament, braided, and/or multifilament string 340 at any one or more locations along the length of the implant 310, as shown in FIG. 39. According to some embodiments, coupling the tether string 340 to multiple locations along the length of the implant 310 can facilitate anchoring the implant 310 in a desired location and can also prevent movement of the implant 310 at an end of the implant 310 opposite the anchor site. By coupling the tether string 340 at multiple locations, the implant 310 may be less likely to change dimensions. In some embodiments, the string material can also comprise one or more bioabsorbable materials that degrade more slowly than the implant 310. Additionally, the geometry and/or configuration of the string 340 can influence its degradation rate. For example, a string 340 made of the same material as the implant 310 may nonetheless degrade more slowly if the diameter of the fibers in the string 340 are significantly larger than the diameter of the fibers 314 that form the implant 310.

In some embodiments, the implant 310 itself can form the anchor. At least a portion of the implant 310 can exit the hollow anatomical structure 320 at the access site 304 and can be left in the subcutaneous tissue and/or positioned across the skin. According to another aspect of the technique, the method further comprises positioning the body 312 so that a portion of the body 312 extends out of the hollow anatomical structure through the skin of the patient at an access site 304 on the skin. According to another aspect of the technique, the body further comprises a tether 340, and the method further comprises trimming an end portion of the body 312 so that it is substantially flush with the skin and so that the tether 340 extends beyond the body through the access site 304. According to another aspect of the technique, the method further comprises securing the tether 340 near the access site 304. Alternatively, in some embodiments, both the tether string and the fibrous mass are cut flush to skin and/or tucked under the skin, such that nothing extends through the skin of the patient at the incision.

In some embodiments, a bioabsorbable tab 350 is provided. The bioabsorbable tab 350 preferably is a separate component. It is preferably deployed on the outside of the hollow anatomical structure 320 in the subcutaneous tissue. The bioabsorbable tab 350 preferably is connected to the implant 310 via a tether string 340 that crosses the wall of the hollow anatomical structure 320. Alternatively, the bioabsorbable tab 350 may be connected directly to the implant 310. For example, at least a portion of the implant 310 can comprise and/or be coupled with a bioabsorbable tab 350. At least the portion of the implant 310 with the tab 350 can extend through the access site 304 such that the bioabsorbable tab 350 can be coupled to the subcutaneous tissue. In some embodiment, the tab 350 can have dimensions of about 1 mm×2 mm×10 mm. In other embodiments, the tab 350 can be smaller or larger. The tab 350 can be made out of PLA, 50/50 PLGA, and/or other bioabsorbable polymers, e.g., some bioabsorbable polymers may be particularly suitable for injection molding. The tab 350 preferably has a geometry and dimensions such that it can be deployed through the same delivery sheath as the implant 310 (e.g., 8 F). The tether string 340 preferably comprises a flexible (suture-like) material. In some embodiments, the tether string 340 can be a monofilament or multifilament braided and/or multifilament yarn. In some embodiments comprising a tether string 340, a first portion of the tether string 340 is preferably coupled to the bioabsorbable tab 350 and a second portion of the tether string 340 is preferably coupled to the implant 310. The attachment at the implant 310 can be on the distal or proximal portions of the implant 310 or in a middle portion, or at any combination of locations. The tether string 340 can control how much the implant 310 is able to stretch when implanted in a hollow anatomical structure 320. As shown in FIG. 39 the tether string 340 can be coupled at a proximal portion of the implant 310, at a plurality of locations on the implant 310, and/or at a distal portion of the implant 310 with one or more knots 344. Additionally, the tether string 340, in some embodiments can be coupled only at a middle and/or intermediate portion of the implant. FIG. 39 also shows a portion of the tether string 340 coupled with a tab 350. In some other embodiments, the tether string 340 can be coupled with another type of anchor and or coupled directly with a portion of the patient's anatomy, e.g., as described herein. Fastening the tether 340 to the distal end portion of the implant 310 effectively fixes that end portion of the implant 310 relative to the access site 304. The tether string 340 can be attached to the tab 350 in any suitable manner. In some embodiments, the tether 340 is coupled to the tab 350 using one or more of a bioabsorbable cyanoacrylate adhesive, a thermal bonding technique, and a mechanical connection, e.g., a knot tied in the tether 340 can prevent it from sliding through a hole in the tab 350 as shown in FIG. 37B.

FIGS. 36A-F illustrate several techniques for fixing the implant 310 relative to the access site 304, for some of the embodiments which have been described above. FIG. 36A illustrates a fixation procedure wherein the implant 310 is cut generally flush with the patient's skin and the tether string 340 is cut off about 5 cm (2 inches) beyond the skin. The wound is preferably closed with a steri-strip, Tegaderm™, or other suitable wound closure element. The tether 340 is then taped to the skin of the patient. The tape can be removed after several days and the tether is cut flush with the skin. FIG. 36B illustrates a fixation procedure wherein the implant 310 and the tether 340 extend across the wall of the hollow anatomical structure 320 and are both cut generally flush with the patient's skin. The wound is closed and the implant 310 and tether 340 are held within the subcutaneous tissue. FIG. 36C illustrates a fixation procedure wherein the implant 310 is cut generally flush with the patient's skin and a bioabsorbable tab 350 is attached to the tether string 340. The tab 350 is coupled to the subcutaneous tissue under the skin to anchor the implant 310 and the wound is closed. According to one technique, the anchor tab 350 is threaded onto the free end of the tether string 340 and the tether string 340 is knotted close to the exit point from the skin to act as a stopper knot to retain the anchor tab 350. One end of the anchor 350 is inserted into the incision. A cannula or blunt tool can be used to push the anchor 350 below the skin surface. Accordingly, the anchor 350 can be positioned outside the vein, but below the skin surface. Additional wound closure techniques can be used at the incision site, e.g., steri-strips and/or tissue adhesives. FIG. 36D illustrates a fixation procedure wherein the tether string 340 attached to a needle 342. The wound is closed and the tether 340 is stitched into the tissue to anchor the implant 310. FIG. 36E illustrates a fixation procedure wherein the tether string 340 is cut off about 5 cm (2 inches) beyond the skin. The tether is then tucked under the skin and the wound is closed. FIG. 36F illustrates a fixation procedure wherein the implant 310 is stretched, cut, and allowed to slide back towards the hollow anatomical structure 320 to minimize expansion of the incision. The anchor string 340 exits the incision and is coupled, e.g., taped, to the skin. The implant thickness preferably does not dilate the incision. The anchor string 340 preferably is low-profile to allow the incision to fully close upon procedure completion. Variations and combinations of the techniques of FIGS. 36A-36F can also be used.

Advantages of some embodiments and techniques using an access site anchor include the ability to mechanically couple the implant with a wall of the hollow anatomical structure and/or surrounding tissue. The procedure is relatively easy and fast and no additional anesthesia is required.

Expandable Anchor

As stated above and as shown in FIG. 37C, according to another aspect of the technique, securing the body 312 comprises implanting an expandable anchor 380 near the body 312 in the hollow anatomical structure 320. For example, in one embodiment, an expandable structure 380, e.g., a braid 382, can be deployed through a catheter and expanded in a vein near the sapheno-femoral junction as shown in FIG. 37C. The structure 380 preferably has sufficient radial force to engage the vein wall and anchor the implant 310 in place. The proximal end portion of the implant 310 preferably is coupled to the braid 382. The braid 382 can comprise bioabsorbable materials. In some embodiments, monofilaments are preferred for forming the braid 382, due to their higher flexural modulus compared to multifilament braids or multifilament yarns. However, multifilament braids or multifilament yarns could be used in some embodiments. Monofilament fibers can provide increased radial strength. In some embodiments, the braid 382, when deployed, is about 2 cm long. In other embodiments the braid 382 can be longer or shorter. When packed into the delivery catheter, the braid 382 elongates. For example, the 2 cm long braid 382 can elongate to about 8 cm long when packed in the delivery catheter. The braid 382 provides a sufficiently large expansion ratio for a given volume of material. The expansion ratio of the braid 382 typically is larger than the expansion ratio for knit or woven structures. However, knit or woven expandable structures can be used in some embodiments. The motion of axially compressing the braid 382 can result in a substantial diameter increase because the individual strands of the braid 382 are allowed to slide relative to each other. In some embodiments, structures 380 can expand from about 6 F to about 20 mm.

In some other embodiments, a braid 382 can comprise a serrated and/or abrasive material to provide increased friction against the wall of a hollow anatomical structure 320. In some embodiments, the braid 382 can be inverted by pulling on one end of the braid 382. Inverting the braid 382 can increase the radial force applied by the braid and/or increase the diameter of the braid. Increasing the number of fibers in a given cross-section over the inverted length also increases the occlusive properties of the braid 382. Additionally, in some embodiments, a separate component associated with the braid 382 can be formed to have teeth or serrations in one or both directions. The separate component can be located on an outer portion of the braid 382 to improve friction with the vessel wall 320. In some embodiments, an expandable structure 380 can be deployed at one or more portions of the implant 310. For example, one or more expandable structures 380 can be deployed at one or more of a proximal portion, a distal portion, and an intermediate portion of the implant 310. Expandable structures 380 can provide a completely endovascular fixation element for the implant 310. In some embodiments, the expandable structure 380 can be larger or smaller in diameter, and/or can have additional or fewer filaments based on the size of the hollow anatomical structure 320. Where the vessel size is smaller, the expandable structure 380 can be made smaller in diameter and/or with fewer filaments to advantageously fit in a smaller delivery sheath.

Figure 40A:
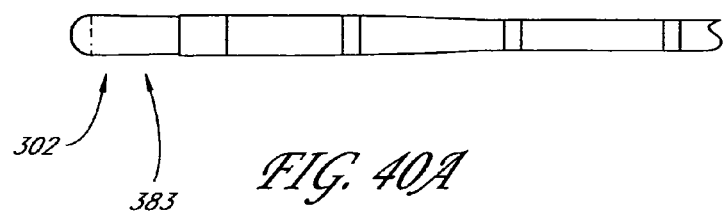
FIGS. 40A-C illustrate a blunt tip "V"-shaped fixation element according to one embodiment.
Figure 40B:
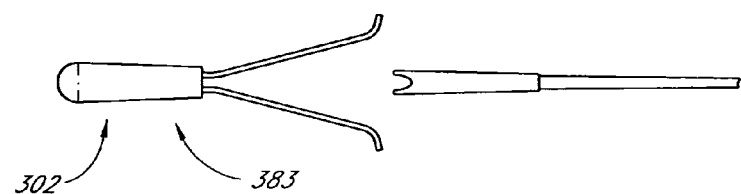
Figure 40C:
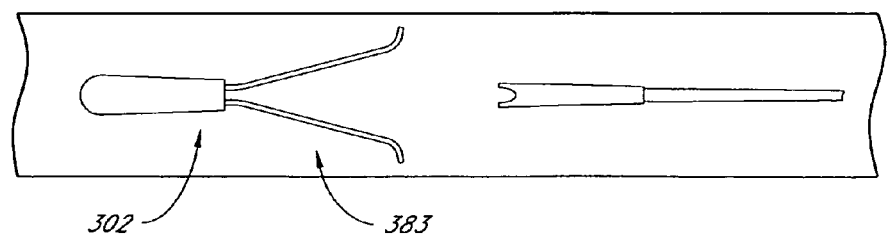

According to another embodiment, a blunt inverse "V"-shaped anchor 383 can be provided as a fixation element 302, e.g., as shown in FIGS. 40A-C. The blunt head of the anchor preferably protrudes from the delivery catheter and functions as an atraumatic tip. The arms collapse slightly while positioned within the catheter and expand when deployed. The ends of the arms are preferably bent outward to provide a better grip against the vessel wall. In some embodiments, at least a portion of the anchor is biodegradable.

Figure 41:
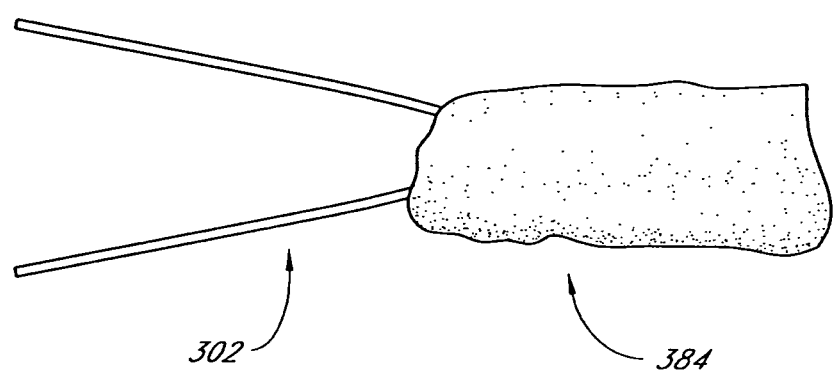
FIG. 41 illustrates a "U"-shaped fixation element according to one embodiment.

According to another embodiment, a "U"-shaped clip 384 can be provided as a fixation element 302, e.g., as shown in FIG. 41. The clip preferably has solid rounded arms that collapse slightly when positioned within the catheter and expand when deployed. The ends can be moderately sharp in some embodiments.

Figure 42A:
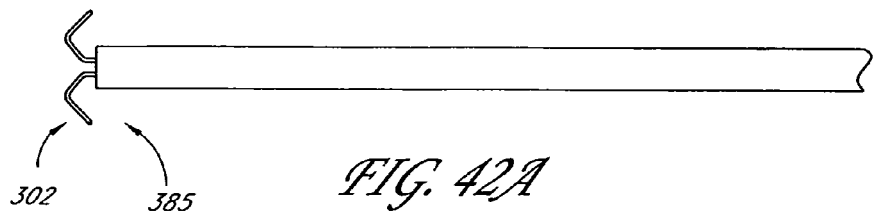
FIGS. 42A-C illustrate an expandable hoop shaped fixation element according to one embodiment.
Figure 42B:
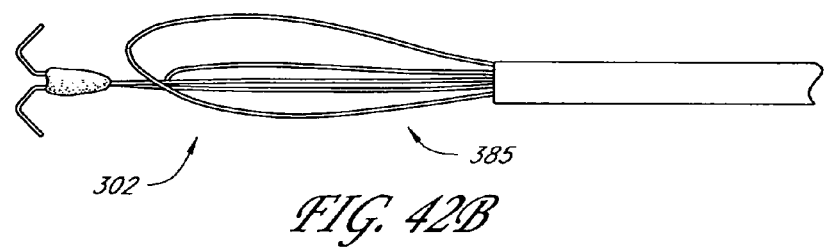
Figure 42C:
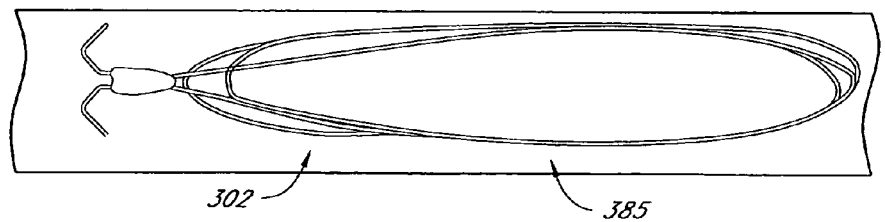

According to another embodiment, expanding wire loops 385 can be provided as a fixation element 302, e.g., as shown in FIGS. 42A-C. The wire loops preferably collapse during delivery and expand when deployed. In some embodiments, hooks are provided at a distal end to provide additional anchoring to the wall of the hollow anatomical structure. The anchor can comprise nickel titanium wire and can be coupled with PLA thread.

Figure 43A:
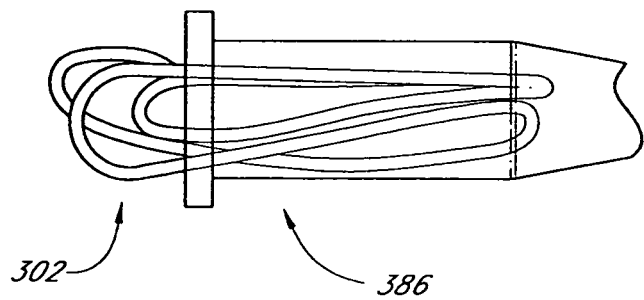
FIGS. 43A-B illustrate an expandable sine wave shaped stent fixation element according to one embodiment.
Figure 43B:
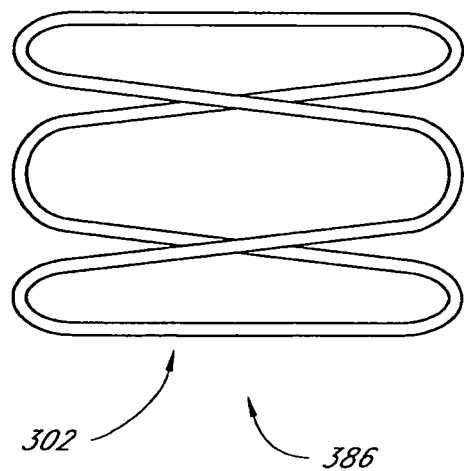
Figure 44A:
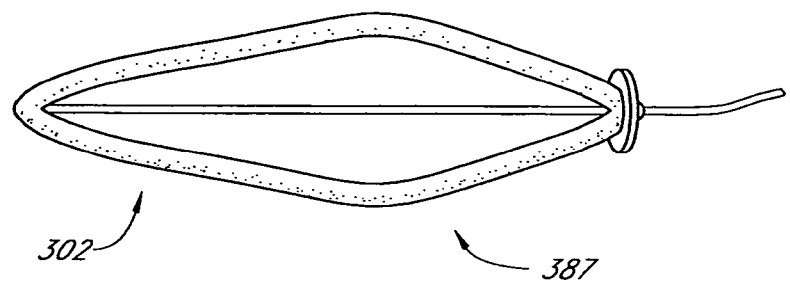
FIGS. 44A-B illustrate an expandable diamond shaped stent fixation element according to one embodiment.
Figure 44B:
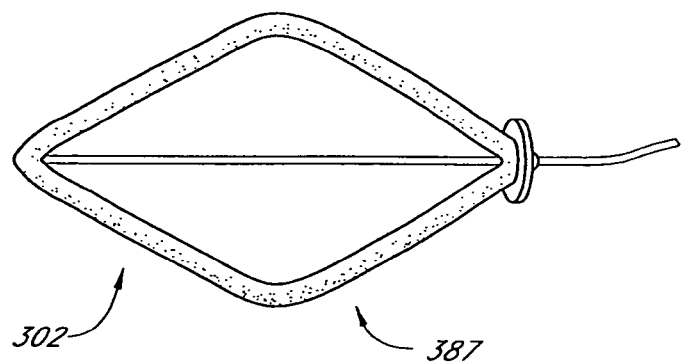

According to another embodiment, an expandable "sine wave" shaped stent 386 can be provided as a fixation element 302, e.g., as shown in FIGS. 43A-B. The stent preferably collapses during delivery and expands when deployed. The stent comprises a solvent-sprayed PLA yarn in some embodiments. In some other embodiments, the stent can have a diamond shape 387, as shown in FIGS. 44A-B. A string can be provided to pull end portions of the diamond closer together, causing the intermediate portions to buckle outward and press against the wall of the hollow anatomical structure.

In some other embodiments, the stent can be a knit tube 388 forming a fixation element 302, e.g., as shown in FIGS. 45A-C. In some embodiments the knit stent can be relatively short, e.g., about 2 cm long, as shown in FIGS. 45B-C. In some embodiments the knit stent can be longer, e.g., up to about 35 cm or more, as shown in FIG. 45A. The knit stent like structures can comprise PLA yarn sprayed with solvent, knit using 8 plies on a four pin knitting machine. In some other embodiments, a braided stent 389 can provided as a fixation element 302, as shown in FIGS. 46A-C. The braided stent can be deployed before the implant is deployed in some embodiments. The braid preferably exhibits some self-expansion. A pull string can be coupled with the braid to aid in further expansion.

Figure 47A:
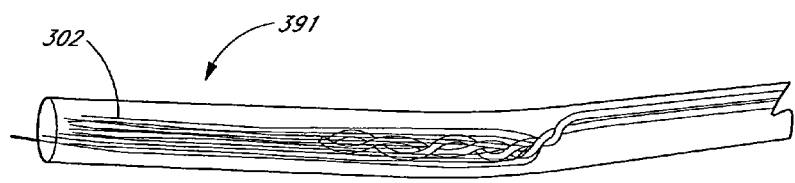
FIGS. 47A-B illustrate an expandable multifilament fixation element according to one embodiment.
Figure 47B:
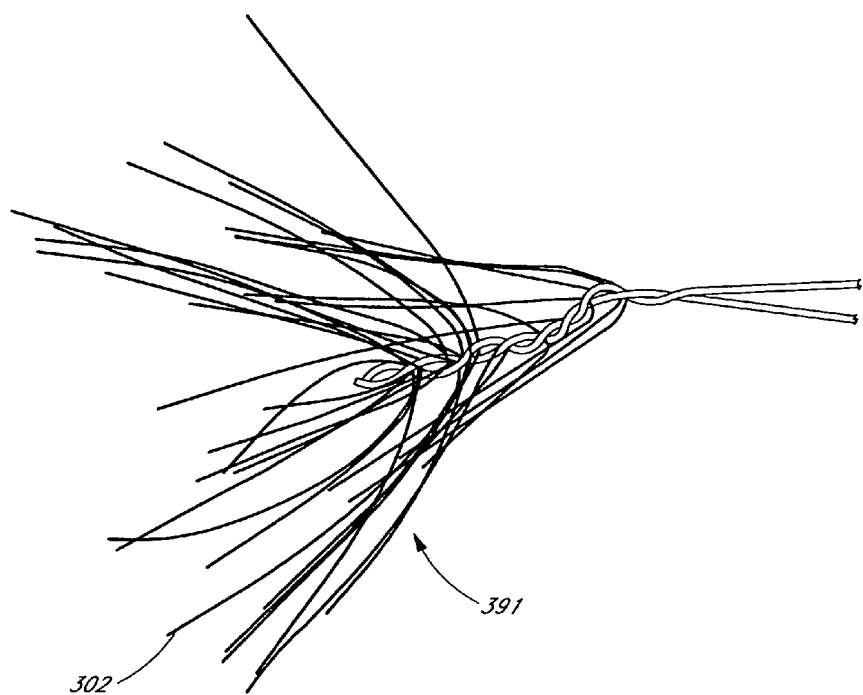

According to another embodiment, a multi-bristle expander 391 can be provided as a fixation element 302, e.g., as shown in FIG. 47A-B. The expander preferably collapses during delivery and expands when deployed. The expander comprises a plurality of monofilament polymer bristles that are moderately stiff. The combined effect of coupling the bristles together enables the expander to grab the wall of a hollow anatomical structure. The expander can comprise one or more bioabsorbable materials.

Advantages of some embodiments and techniques using an expandable anchor structure include the ability to combine delivery of the expandable anchor structure with the delivery of the implant in a single procedure. The expandable element is coupled within the hollow anatomical structure and relies on friction with the wall of the hollow anatomical structure to anchor the implant. Appropriately sized expandable structures can be selected. The expandable element may or may not be bioabsorbable.

Thermal Fixation and/or Vessel Shrinkage

As stated above and as shown in FIG. 37A, according to another aspect of the technique, securing the body 312 comprises thermally shrinking the hollow anatomical structure 320 near an implant location in the hollow anatomical structure 320. Implanting the body 312 preferably comprises implanting the body 312 at the implant location. For example, in one embodiment, heat is used to spot shrink an approximately 1 cm section of a vein near the sapheno-femoral junction. There are a number of ways to shrink a hollow anatomical structure 320. In one embodiment, a preferably self-contained and battery-operated heating coil can be located on the outer surface of the implant delivery catheter. Thus, a single catheter can be configured to perform the thermal shrink function and the implant delivery function. The battery may be contained in the handle of the catheter, or in a separate, rechargeable power base connected to the catheter via direct contact or an electrical cable. In other embodiment, any suitable energy tool and power supply can be used. In some embodiments, the handle can comprise one or more capacitors in lieu of, or in addition to, batteries. The energy delivered by a battery may be controlled by use of a timed on/off circuit. The capacitor value may be selected such that it delivers the desired amount of energy when discharged.

According to one technique for achieving thermal shrinkage, an implant 310, a 6 F delivery catheter comprising a coil heater, a 6 F sheath and dilator, a guidewire, a pushrod, and a sharp are provided. The sharp is pierced through the skin, subcutaneous tissue, and hollow anatomical structure wall to access the interior of the hollow anatomical structure. The guidewire is inserted through the sharp into the hollow anatomical structure. The sharp is removed leaving the guidewire in the hollow anatomical structure. The dilator and sheath assembly is threaded over the guidewire and into the hollow anatomical structure. The dilator and guidewire are removed, leaving the sheath in place. The implant 310 is prepared for loading into the delivery catheter. According to one embodiment, the implant 310 is a fibrous mass and comprises three strands of 600 denier PLA. The strands are preferably doubled over, effectively forming six strands. The implant 310 in some embodiments is preferably fused together at the tip with solvent to prevent blood from soaking into the implant and coagulating during the heating step. The anchor string preferably comprises size 3-0 silk. In some other embodiments, the anchor string preferably comprises Vicryl Rapide™. The anchor string is coupled to the distal end portion of the implant with a knot. The anchor string is preferably interlaced with strands of the implant along the length of the implant 310. The push rod can be a forked push rod formed from a 0.8 mm (0.03 inch) stainless steel mandrel. The implant 310 is preferably loaded onto the push rod. The three strands are preferably folded over the fork at the knot. The push rod is used to guide the implant 310 into the catheter. The push rod is advanced until the sheath and push rod tips match. In some embodiments, the push rod is advanced until a mark on the push rod reaches the sheath hub. The loaded catheter is inserted into the sheath. The catheter is advanced to the proximal end of the desired treatment area within the hollow anatomical structure. In some embodiments, tumescent anesthesia is delivered to the treatment site to provide anesthetic, heat sink, and compressive effects. The coil heater is activated by pressing a button on the catheter to deliver heat to shrink the hollow anatomical structure. The catheter is pulled back slightly and the outer sheath is withdrawn. The implant 310 is exposed while the push rod is held in place. Accordingly the implant 310 is deployed within the hollow anatomical structure behind the heat treated section. With the implant 310 fully deployed, the push rod and delivery catheter are withdrawn from the sheath. Finally the sheath is fully withdrawn. Additional fixation techniques can be performed if necessary and/or desired. Variations and modifications to the technique can be made.

The shrinkage may also be achieved via other thermal means such as a radio frequency (RF) emitting catheter (such as a VNUS Closure™ catheter) or endovenous laser. Additional disclosure regarding heating elements is provided in U.S. Pat. No. 6,401,719, issued Jun. 11, 2002, titled METHOD OF LIGATING HOLLOW ANATOMICAL STRUCTURES; or in U.S. Pat. No. 6,179,832, issued Jan. 30, 2001, titled EXPANDABLE CATHETER HAVING TWO SETS OF ELECTRODES; or in U.S. Pat. No. 6,769,433, issued Aug. 3, 2004, titled Expandable vein ligator catheter having multiple electrode leads, and method; or in U.S. Pat. No. 6,638,273, issued Oct. 28, 2003, titled Expandable catheter having improved electrode design, and method for applying energy; or U.S. patent application Ser. No. 11/222,069, filed Sep. 8, 2005, titled METHODS AND APPARATUS FOR TREATMENT OF HOLLOW ANATOMICAL STRUCTURES; or U.S. patent application Ser. No. 11/236, 316, filed Sep. 27, 2005, titled SYSTEMS AND METHODS FOR TREATING A HOLLOW ANATOMICAL STRUCTURE; or U.S. Provisional Patent Application No. 60/613, 415, filed Sep. 27, 2004, titled RESISTIVE ELEMENT SYSTEM. The above-mentioned U.S. Patents and Applications are hereby incorporated by reference herein and made a part of this specification.

Figure 48A:
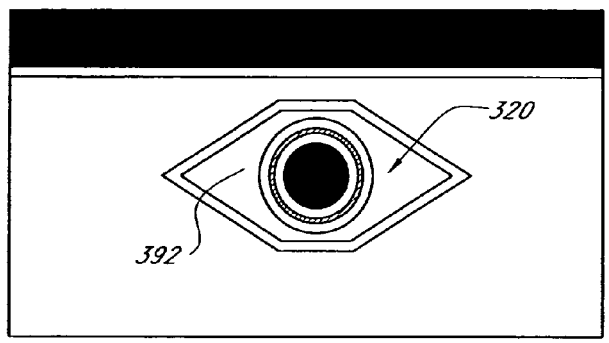
FIGS. 48A-C illustrate one embodiment of a method of providing bulking hollow anatomical structure.
Figure 48B:
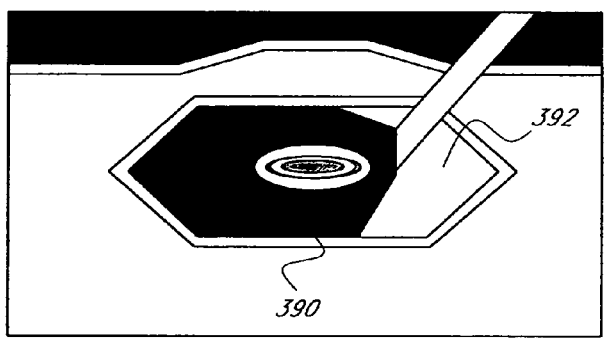
Figure 48C:
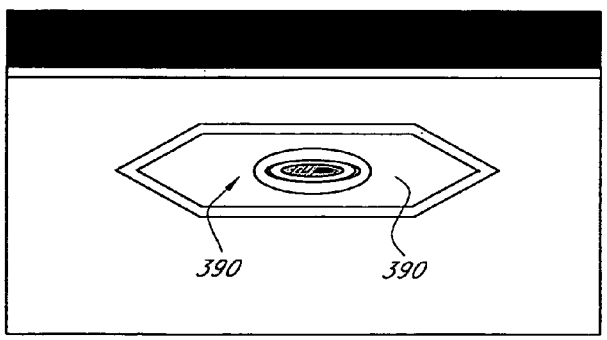

Alternatively, external bulking agents can be used, as is shown in FIGS. 48A-C. For example, FIG. 48A shows a vessel 320 prior to treatment with a bulking agent 390. As shown in FIG. 48B, bulking agents 390 can be injected into a compartment surrounding a vessel to compress the vessel 320. As shown in FIG. 48C, following treatment, bulking material 390 can be absorbed and replaced by tissue. Bulking agents 390 preferably are more viscous and comprise materials that are more long lasting than saline. Materials injected into the perivenous space 392 near the sapheno-femoral junction can temporarily occlude the vein for a period of days to weeks to limit implant migration and particle embolization. According to some embodiments, materials such as, for example, FloSeal, VNUSeal, and/or gelatin can be used if sufficiently large access, e.g., 6 F, is available. In some embodiments, TissueMend (degradable cyanoacrylate) and/or Atrigel (indictable PLA) can be used for smaller access sites. Additionally, in some embodiments, bulking materials 390 can comprise yarn delivered for example by a continuous feed mechanism as described herein.

Figure 49:
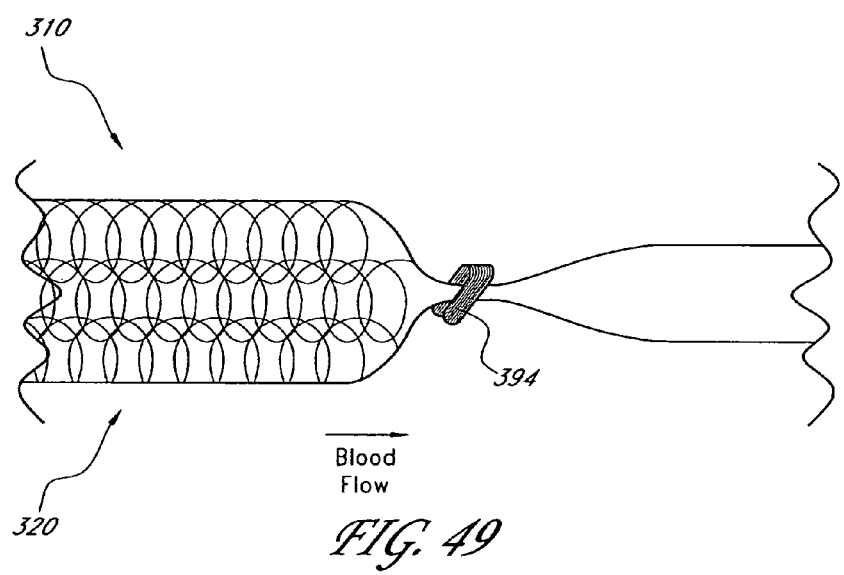
FIG. 49 illustrates a biodegradable clip fixation element according to one embodiment.

Alternatively, in some embodiments, the vessel 320 can be ligated from within the vessel or external to the vessel to prevent migration. One embodiment includes an external bioabsorbable (or non-absorbable) ligation clip 394 or suture to restrict the size of the hollow anatomical structure, as shown in FIG. 49. A reduction in diameter of the hollow anatomical structure acts a as flow restriction as well as a physical stop for the implant 310. The implant 310 is deployed behind the reduced diameter portion of the hollow anatomical structure 320.

Advantages of some embodiments and techniques using a thermal treatment and/or vessel shrinkage include the ability to create a physical barrier to implant migration using the natural tissue of the hollow anatomical structure. A reduction in the vessel size results in reduced blood flow. Reduced blood flow improves coagulation and reduces the flow challenge to the implant. Positioning accuracy for the implant in increased.

Fenestration Anchor

As stated above and as shown in FIG. 37D, according to another aspect of the technique, securing the body comprises securing the body 312 with a fenestration anchor 360. For example, in one embodiment, a fenestration anchor 360 is similar in structure to the bioabsorbable tab 350, except that the method of deploying the fenestration anchor 360 remotely and endoluminally from the access site 304 is more complex. In some embodiments, the deployment of the fenestration anchor 360 into a hollow anatomical structure 320, e.g., a vein, is similar to vein access using the Seldinger technique. However, instead of accessing the vein with a needle, proceeding from outside the body to inside the vein, the procedure is reversed. A needle-tipped steerable catheter can be used to access the perivascular space from a starting point inside the vein. In one technique, under ultrasound guidance, the needle preferably is positioned near the sapheno-femoral junction and punctures the vein wall. The dilating portion of the catheter and the implant delivery sheath are both advanced over the needle across the vein wall. The needle and dilator are removed, leaving the sheath lumen open to deliver the anchor and implant. The fenestration anchor is deployed into the perivascular space and the sheath is retracted, leaving the fenestration anchor on the outside of the vein. Further retraction of the sheath exposes the implant 310. As described above with the tab 350, the fenestration anchor 360 and the implant 310 preferably are connected through the vein wall by a tether string 340. Additional through-wall fenestration concepts are shown in FIGS. 50-54C.

Figure 50:
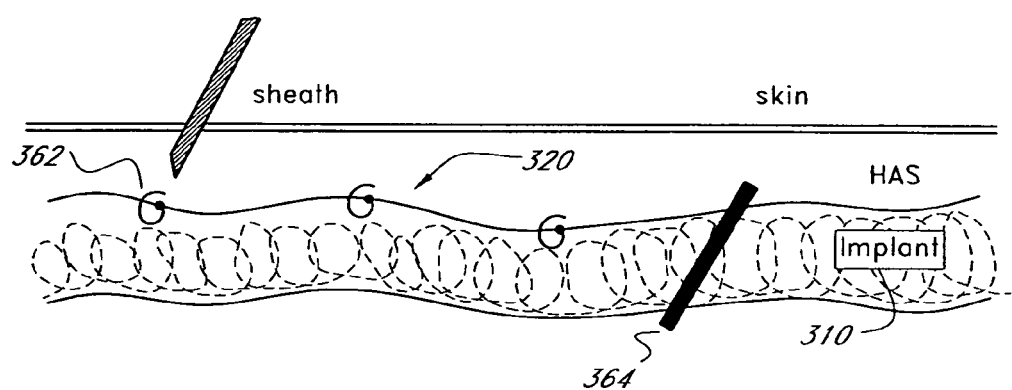
FIG. 50 illustrates a fenestration technique according to one embodiment.
Figure 51F:
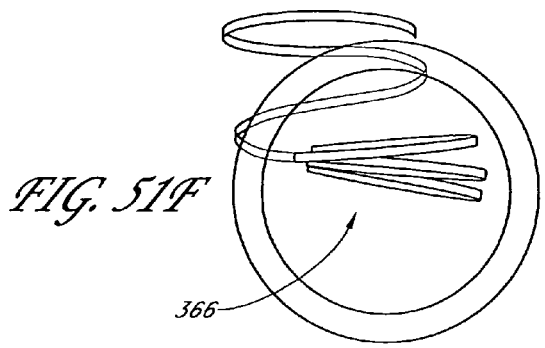
Figure 51G:
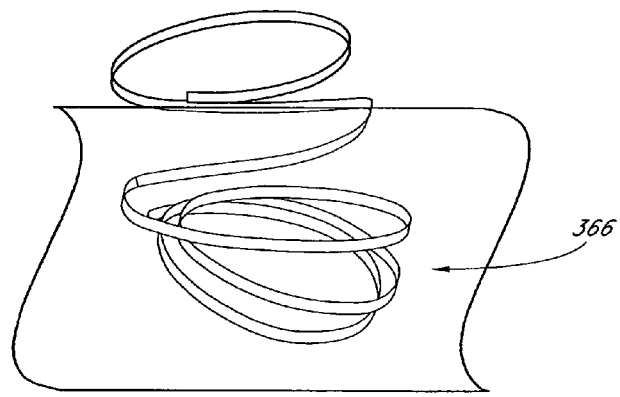
Figure 51H:
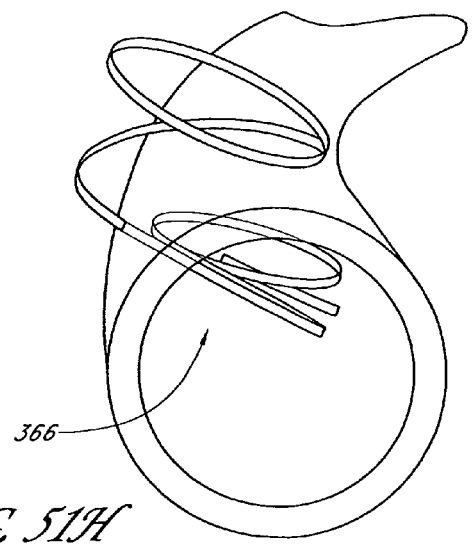

As shown in FIG. 50, according to another aspect of the technique, securing the body 312 comprises anchoring the body within the hollow anatomical structure by suturing the body within the hollow anatomical structure 320. For example, as shown in the illustrated embodiment, the implant 310 can be anchored by a single or series of external sutures 362 tied along the vessel 320 though the vessel wall and through the implant 310 to hold it in place. This technique can be accomplished by simple open surgical loops or by using a minimally invasive cannula and/or needle delivered knots, clips, and/or staples by fenestrating the vessel and/or guiding the needle with ultrasound. In some embodiments, fenestration clips and/or suture knots 362 hold the implant 310 to the vessel wall. In some embodiments, a bioabsorbable stake or pin 364 can be fenestrated through one or more walls of the hollow anatomical structure and through the implant 310.

Figure 52A:
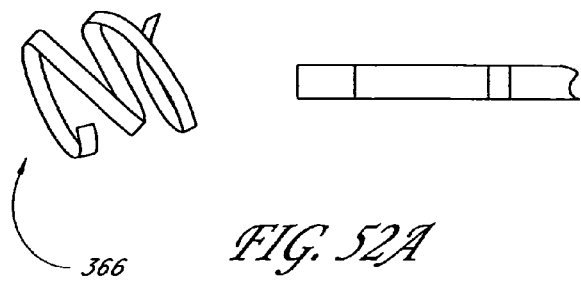
FIGS. 52A-B illustrate a polymer coil according to one fixation embodiment.
Figure 52B:
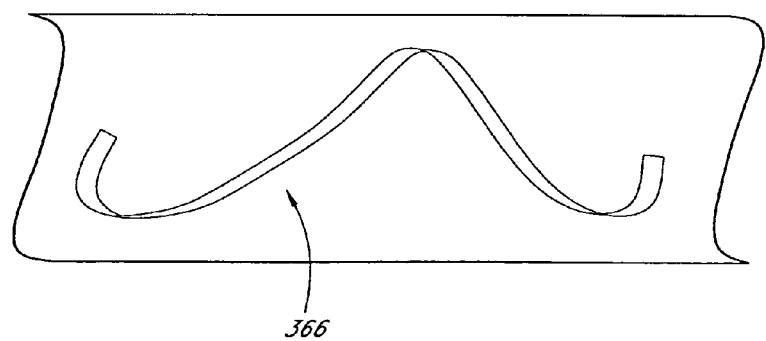

According to some other embodiments, fenestrating coils 366, such as those shown in FIGS. 51A-H can be used for fixation procedures. For example, in some embodiments, small coils can be deployed singly with the aid of a needle and suture. In some embodiments, larger coils can be deployed all at once by a delivery device. In some embodiments, fenestrating coils 366 can comprise nickel titanium wire having rectangular or rounded cross sections. A large diameter coil can act as a filter for large particles as well as an anchor in some embodiments. According to another embodiment, as shown in FIGS. 52A-B a polymer coil 366 can be provided in a fixation procedure. For example, a rectangular rod stock can be formed into a tight coil. The coil can be straightened and inserted into a delivery catheter. The coil can then be pushed out into a hollow anatomical structure where it regains at least a portion of its coil shape. In one embodiment the coil comprises polyethylene and can be inserted through a 6 F sheath.

Figure 53A:
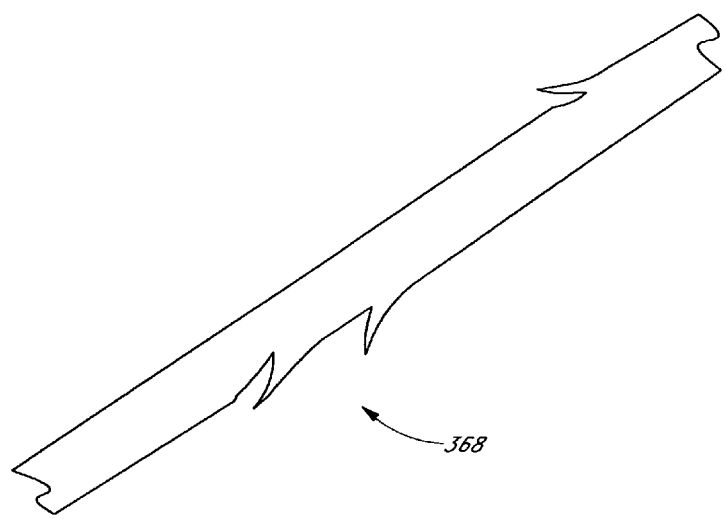
FIGS. 53A-B illustrate a barbed suture according to one fixation embodiment.
Figure 53B:
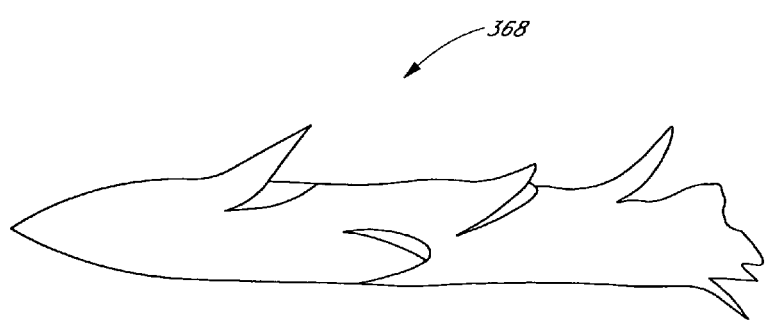

According to another embodiment, a barbed suture 368 can be provided as a fixation element, e.g., as shown in FIG. 53A-B. The barbed sutures 368 can be used for wound closures in some embodiments and for fixing an implant to a hollow anatomical structure in some embodiments. The barbed sutures 368 are preferably self-anchoring and may or may not be bioabsorbable in some embodiments.

Figure 54A:
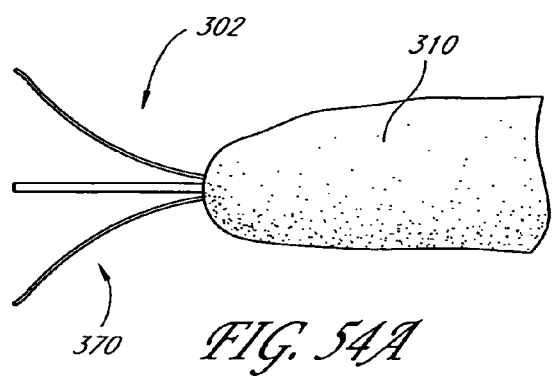
FIGS. 54A-C illustrate a multi-pronged expandable fixation element according to one embodiment.
Figure 54B:
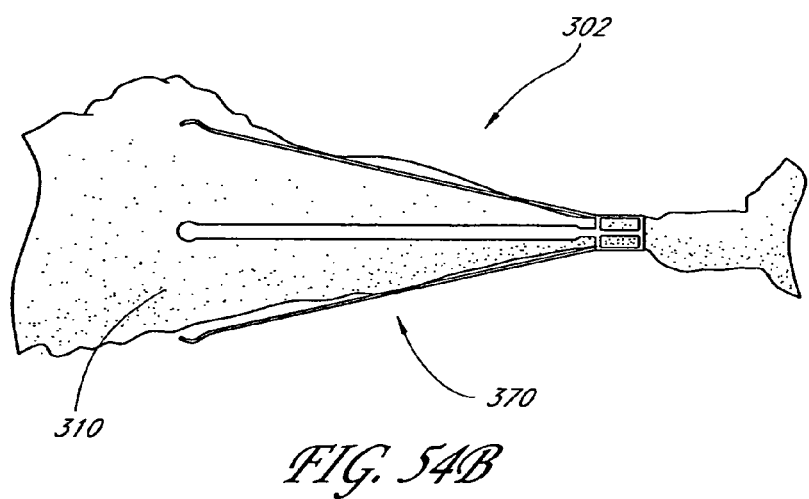
Figure 54C:
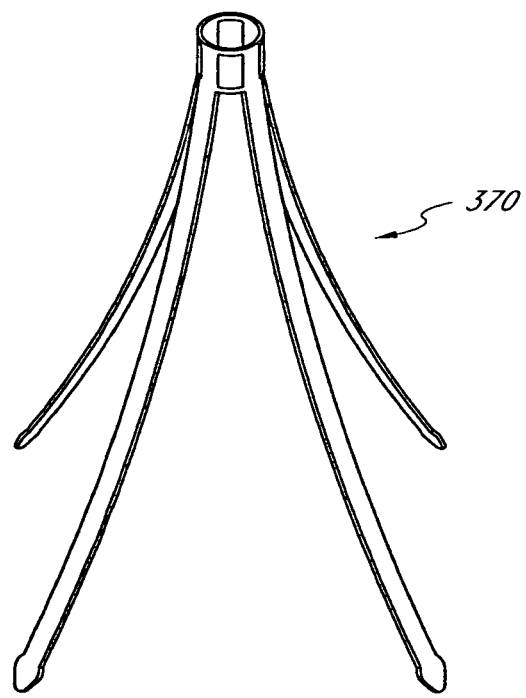

According to another embodiment, as shown in FIG. 54A-C, a multi-pronged expander 370 can be used as a fixation element 302. The element preferably has a plurality of thin, flat arms and/or prongs fixed at a first end portion, the arms bending away from one another near a second end portion of the fixation element 302. The element 302 can be compressed for delivery and can expand upon exiting the catheter. The fixation element 302 preferably is coupled with an implant 310. The fixation element 302 can be coupled at one or more of a proximal portion, a distal portion, and an intermediate portion of the implant 310. In some embodiments, the expander 370 can have more or less than four prongs. In some embodiments, as shown in FIG. 54C, the tips of the prongs are sharp to enable the expander 370 to grab and/or penetrate the walls of a hollow anatomical structure 320 when pushed forward.

According to one technique for deploying an implant and a fenestration anchor, an implant coupled with a fenestration anchor, a needle catheter, a 6 F sheath are provided. The catheter tip comprises a retractable needle. The needle is preferably retracted during initial insertion of the catheter into the hollow anatomical structure. The catheter is advanced through the sheath to a proximal end of the desired treatment area. Tumescent anesthesia preferably is delivered to the treatment area to provide anesthesia and to create a space outside the hollow anatomical structure to aim the needle and deploy the anchor. The needle is deployed and preferably locked in place. The needle catheter is advanced to pierce the wall of the hollow anatomical structure at the desired location. The catheter and sheath extend outside the wall of the hollow anatomical structure. The needle is unlocked and retracted, and the catheter is withdrawn leaving the sheath across the wall of the hollow anatomical structure. The implant is prepared for loading into the delivery catheter. A forked push rod is provided. According to one embodiment, the implant is a fibrous mass and comprises three strands of 600 denier PLA. The strands are preferably doubled over, effectively forming six strands. According to one embodiment, the anchor is a 1 mm×2 mm×10 mm bar with a hole through the center. An anchor string is provided. An end portion of the anchor string is formed into a stopper knot to retain the anchor. Another knot preferably fixes a distal end portion of the implant about 5 mm away from the anchor point. In some embodiments the distance between the anchor and the implant can be smaller or greater. The tether string preferably is interlaced with the strands of the implant along the length of the implant. The implant is loaded onto the push rod. The three strands are preferably folded over the fork at the knot on the implant. The anchor is pushed into the catheter. The push rod and the implant are fed into the catheter pushing the anchor in front of the implant. The anchor exits the tip of the catheter. The anchor preferably is completely deployed outside the catheter while the implant and pushrod are near the tip of the catheter. In some embodiments, the anchor and tip of the sheath are preferably doped with barium sulfate and/or air bubbles or other suitable indicators to make the anchor and tip more visible under ultrasound. The catheter is then retracted. Initially, the anchor will follow as the catheter is retracted. The configuration of the anchor prevents it from reentering the hollow anatomical structure. The implant is exposed as the catheter continues to retract until the implant is fully exposed. Variations and modifications to the technique can be made.

Advantages of some embodiments and techniques using a fenestration anchor include the ability to mechanically couple the implant with a wall of the hollow anatomical structure and/or surrounding tissue. The procedure also allows for increased positioning accuracy for the implant compared with some other techniques.

Retrograde Access Anchor

As stated above and as shown in FIG. 37E, according to another aspect of the technique, securing the body comprises anchoring the body at a percutaneous retrograde access site 306. For example, in one embodiment, a vein access site 306 is located near the sapheno-femoral junction rather than near the knee or ankle. Other than the relative position of the access site, this technique is similar to the other access site anchor techniques described herein and it can be combined with any of the other techniques as desired. The advantage of a retrograde access over traditional GSV access is the ability to fix the implant 310 to the tissue at the proximal end, very close to the sapheno-femoral junction, thereby restricting movement of the implant 310 into the deep vasculature. The catheter used in retrograde access can have additional features to improve navigability across the vein valves. Such features can include a blunt, less traumatic tip profile, and/or steering capability.

Advantages of some embodiments and techniques using a percutaneous retrograde access anchor include the ability to mechanically couple the implant with a wall of the hollow anatomical structure and/or surrounding tissue. The procedure also allows for increased positioning accuracy for the implant compared with some other techniques by having an access site nearer the sapheno-femoral junction. Insertion of the sheath allows for a smaller incision than those used to perform ligation and stripping procedures. Accessing a femoral vein at the groin is a common procedure and access to the femoral vein is easily achieved. The need to use an extra vascular closure device or extensive manual compression for hemostasis is avoided because most of the flow is occluded with the implant in place.

Wedge Fixation

Figures 55A, 55B:
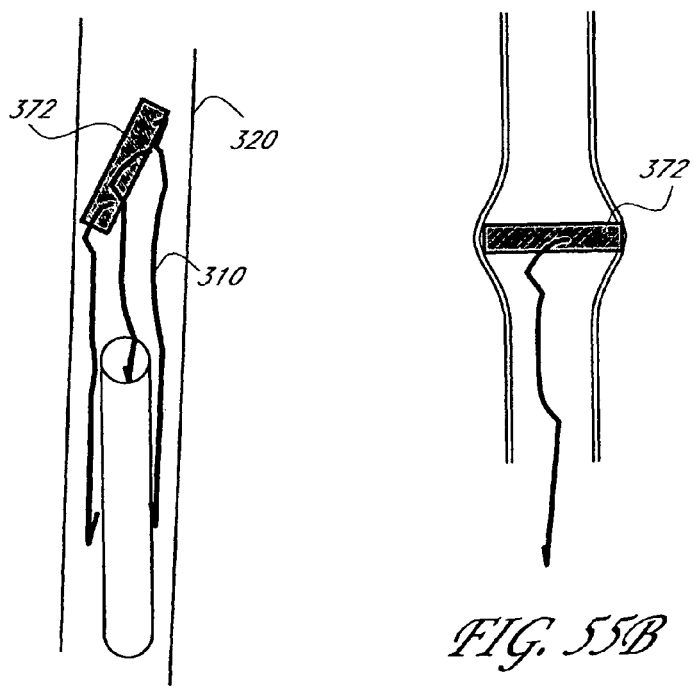
FIGS. 55A-B illustrate a wedge-type fixation element according to one embodiment.

As shown in FIG. 55A-B, according to another aspect of the technique, securing the body 312 comprises anchoring the body 312 within the hollow anatomical structure 320 by wedging an anchor element 372 within the hollow anatomical structure 320. For example, in the illustrated embodiment, an elongate member 372 is positioned perpendicular to a vein and is thereby wedged in place. In some embodiments, the elongate member 372 can be made out of PLA, 50/50 PLGA, or other bioabsorbable polymers suitable for injection molding. In some embodiments, the end portions of the elongate member are flat. In other embodiments, the end portions can be sharp, pointed, and/or rounded.

Figure 56A:
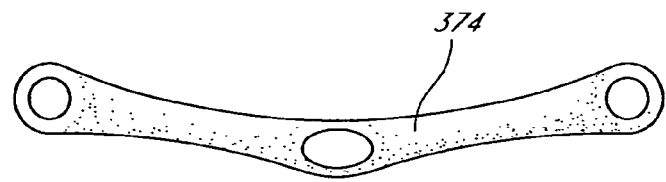
FIGS. 56A-B illustrate a wedge-type fixation element according to another embodiment.
Figure 56B:
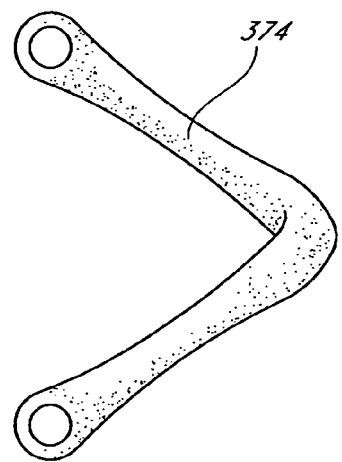
Figure 57A:
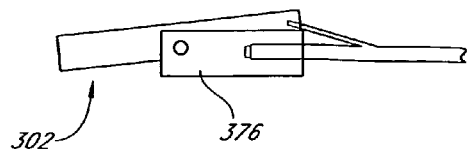
FIGS. 57A-C illustrate a "T"-shaped wedge-type fixation element according to another embodiment.
Figure 57B:
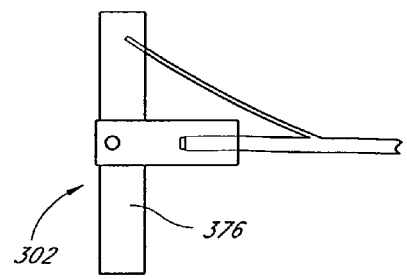
Figure 57C:

FIGS. 56A-57C illustrate additional elongate members having alternative shapes and configurations that can also be used in one or more fixation techniques. For example, a tilting bar comprising a solvent sprayed yarn 374 can be provided, as shown in FIGS. 56A-B. The tilting bar 374 is preferably more flexible than the elongate member 372 described above. According to another embodiment, a swivel "T" structure 376 can be provided as a fixation element 302, e.g., as shown in FIGS. 57A-C. The swivel has first and second elongate portions coupled together such that the first elongate portion swivels relative to the second elongate portion. When the fixation element 302 is positioned in the hollow anatomical structure, the elongate portions can be swiveled such that one elongate portion is positioned across the width of the vein wall and is thus wedged in place. The element can be actuated using one or more of a string, a pushrod, or other suitable tool 308. Any suitable materials can be used.

Plug Fixation

According to another aspect of the technique, securing the body comprises anchoring the body within the hollow anatomical structure by positioning a plug within the hollow anatomical structure. For example, a preformed foam plug or foam sponge can be used in lieu of the expandable element, e.g., the braid, described above, as an alternative frictional anchor. In one embodiment, the foam is coupled to the implant. In some embodiments, the foam has the ability to block flow even more readily than the implant itself. The foam can be made of biodegradable materials such as, for example, polyglycolide, polylactide, poly-caprolactone, and/or copolymers of these materials. More information regarding bioabsorbable foams is provided by S. I. Jeong, et al, in a paper entitled "Manufacture of Elastic Biodegradable PLCL Scaffolds for Mechano-Active Vascular Tissue Engineering," (J. Biomater. Sci. Polymer Edn, Vol. 15, No. 5., pp. 645-660 (2004)), which is hereby incorporated by reference herein in its entirety.

Advantages of Fixation Techniques

Some preferred embodiments and methods for fixation are specially adapted to function in tapering vessel lumens to prevent migration of the implant. For example, mechanical anchors have the inherent advantage of functioning independent of the vessel taper. Additionally, an expanding element can advantageously be adapted to fit a variable diameter vessel, for example, by expanding non-uniformly. Additionally, for migration prevention of the implant, flow reduction can be desirable. Some techniques, such as the expanding braid and/or the thermal shrink techniques, have an additional feature of restricting the flow the implant is subjected to. The reduced flow has two distinct mechanisms for further reducing implant migration: The forces acting on the implant are reduced and the coagulation that is part of the biologic occlusion process can take place more readily in the presence of reduced flow. However, in the acute healing phase, completely occluding flow can have a negative impact on the efficacy of the migration prevention by causing pressure build up which can cause the lumen to swell. This is undesirable in many cases because a swollen vein is more likely to be palpable and less likely to be occluded without recanalization. Accordingly, in the acute healing phase, reducing the flow but not completely blocking the flow can be advantageous. In addition to the expanding anchor and thermal shrink anchor embodiments, the implant itself also provides a flow restricting function.

Additional Delivery System and Technique

According to another embodiment and technique, an implant can be delivered directly into a hollow anatomical structure without using a delivery catheter. For example, the implant can be pushed through the native vessel using the pushrod. This provides the advantage of being able to provide more space to accommodate additional fibers in the implant because the implant doesn't have to go through a delivery catheter that is smaller than the access sheath. Another advantage is that in some embodiments, as the material of the implant drags along the vessel wall it is abrasive on the wall of the hollow anatomical structure, similar to other embodiments wherein an abrasive element is coupled with the sleeve, the catheter and/or the implant to denude endothelial cells to set up a more durable biologic occlusion.

Additional embodiments comprise methods of sterilization. Certain such methods can comprise sterilizing, either terminally or sub-terminally, any of the apparatus disclosed herein that are intended for insertion into (or other contact with) the patient or that are intended for use at or near the surgical field during treatment of a patient. Any suitable method of sterilization, whether presently known or later developed, can be employed.

Accordingly, certain methods comprise sterilizing, either terminally or sub-terminally, any one or combination of the following apparatus: the implant 10/310 and/or any of the embodiments or derivatives thereof disclosed herein; the delivery catheter 16; the pushrod 18; the occlusion system 200, including the fibrous mass 210, delivery member 230 and/or sheath 232; and/or any of the fixation elements disclosed herein. Any suitable method of sterilization, whether presently known or later developed, can be employed. For example, the method can comprise sterilizing any of the above-listed apparatus with an effective dose of a sterilant such as cyclodextrin (Cidex™), ethylene oxide (EtO), steam, hydrogen peroxide vapor, electron beam (E-beam), gamma irradiation, x-rays, or any combination of these sterilants.

The sterilization methods can be performed on the apparatus in question while the apparatus is partially or completely assembled (or partially or completely disassembled); thus, the methods can further comprise partially or completely assembling (or partially or completely disassembling) the apparatus before applying a dose of the selected sterilant(s). The sterilization methods can also optionally comprise applying one or more biological or chemical indicators to the apparatus before exposing the apparatus to the sterilant(s), and assessing mortality or reaction state of the indicator(s) after exposure. As a further option, the sterilization methods can involve monitoring relevant parameters in a sterilization chamber containing the apparatus, such as sterilant concentration, relative humidity, pressure, and/or apparatus temperature.

In view of the foregoing discussion of methods of sterilization, further embodiments comprise sterile apparatus. Sterile apparatus can comprise any of the apparatus disclosed herein that are intended for insertion into (or other contact with) the patient or that are intended for use at or near the surgical field during treatment of a patient. More specifically, any one or combination of the following can be provided as a sterile apparatus: the implant 10/310 and/or any of the embodiments or derivatives thereof disclosed herein; the delivery catheter 16; the pushrod 18; the occlusion system 200, including the fibrous mass 210, delivery member 230 and/or sheath 232; and/or any of the fixation elements disclosed herein.

CONCLUSION

The above description discloses numerous methods, systems, apparatuses and materials. The inventions disclosed herein are susceptible to modifications in the methods, systems, apparatuses and materials, as well as alterations in the fabrication methods and equipment. Such modifications will become apparent to those skilled in the art from a consideration of this disclosure or practice of the invention disclosed herein. Consequently, it is not intended that the inventions be limited to the specific embodiments disclosed herein, but that they cover all modifications, alternatives and combinations coming within the true scope and spirit thereof.

Except as further described herein, the embodiments, features, systems, devices, materials, methods and techniques described herein may, in some embodiments, be similar to any one or more of the embodiments, features, systems, devices, materials, methods and techniques described in U.S. Provisional Patent Application No. 60/605,843, filed Aug. 31, 2004, titled APPARATUS AND MATERIAL COMPOSITION FOR PERMANENT OCCLUSION OF A HOLLOW ANATOMICAL STRUCTURE; and in U.S. patent application Ser. No. 11/212,539, filed Aug. 26, 2005, titled APPARATUS AND MATERIAL COMPOSITION FOR PERMANENT OCCLUSION OF A HOLLOW ANATOMICAL STRUCTURE. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned U.S. Provisional Patent Application No. 60/605,843, and in U.S. patent application Ser. No. 11/212,539. The above-mentioned U.S. Provisional Patent Application No. 60/605,843, and U.S. patent application Ser. No. 11/212,539 are hereby incorporated by reference herein in their entireties and made a part of this specification.

A number of applications, publications and external documents are incorporated by reference herein. Any conflict or contradiction between a statement in the bodily text of this specification and a statement in any of the incorporated documents is to be resolved in favor of the statement in the bodily text.

What is claimed is:

1. A method of treating a hollow anatomical structure having a lumen, the method comprising:
   inserting an implant into the lumen, the implant comprising a radially-compressible fibrous mass and a tether extending axially through the fibrous mass to a distal tether end coupled to a distal end of the fibrous mass, wherein the fibrous mass predominantly comprises a plurality of loose bioabsorbable fibers that are in substantial alignment with each other along their lengths, wherein the fibers are radially-bulked, such that when the fibrous mass is in a radially compressed configuration, each of the fibers has a greater length and defines a smaller radial thickness than when the fibrous mass is in a radially uncompressed configuration, wherein inserting the implant comprises inserting the implant into the lumen with the fibrous mass in its compressed configuration, and so that the tether has a proximal end extending outside of the hollow anatomical structure, and wherein the hollow anatomical structure comprises a blood vessel;
   securing the proximal end of the tether to tissue outside of the hollow anatomical structure;
   allowing the fibrous mass to expand within the lumen from its radially compressed configuration toward its radially uncompressed configuration as the fibers of the fibrous mass decrease in length and thereby define a greater radial thickness, thereby creating a high void-content scaffold spanning a section of the lumen of the hollow anatomical structure and causing a partial occlusion of the lumen, wherein causing the partial occlusion comprises reducing blood flow through the lumen by 10%-90%; and
   gradually creating a substantially complete occlusion of the lumen by allowing blood to infiltrate the voids of the scaffold.

2. The method of claim 1, wherein said hollow anatomical structure comprises a varicose vein.

3. The method of claim 1, wherein causing a partial occlusion of said hollow anatomical structure comprises reducing blood flow through the lumen by 20%-80%.

4. The method of claim 1, wherein causing a partial occlusion of said hollow anatomical structure comprises reducing blood flow through the lumen by 25%-75%.

5. The method of claim 1, wherein, creating a substantially complete occlusion further comprises causing complete occlusion as a result of tissue in-growth within the scaffold.

6. A method of reducing the patency of a blood vessel having a lumen, the method comprising:
   inserting an implant into the lumen, the implant comprising a radially-compressible fibrous mass and a tether extending axially through the fibrous mass to a distal tether end coupled to a distal end of the fibrous mass, wherein the fibrous mass predominantly comprises a plurality of loose bioabsorbable fibers that are in substantial alignment with each other along their lengths, wherein, when the fibrous mass is in a radially compressed configuration, each of the fibers assumes a first state with a first length and defining a first amount of tortuosity, and when the fibrous mass is in a radially uncompressed configuration, each of the fibers assumes a second state with a second length less than the first length and defining a second amount of tortuosity greater than the first amount of tortuosity, wherein inserting the implant comprises inserting the implant into the lumen with the fibrous mass in its compressed configuration, and so that the tether has a proximal end extending outside of the hollow anatomical structure;
   allowing the fibrous mass to expand within the lumen from its radially compressed configuration toward its radially uncompressed configuration, so that the fibers of the fibrous mass change from the first state to the second state, thereby creating a high void-content scaffold that partially occludes the lumen and reduces blood flow through the lumen by 10%-90%; and
   securing the proximal end of the tether to tissue outside of the blood vessel; and
   gradually creating a substantially complete occlusion of the lumen by allowing blood to infiltrate the voids of the scaffold.

7. The method of claim 6, wherein said fibers of said fibrous mass are crimped.

8. The method of claim 6, wherein said fibers of said fibrous mass are textured.

9. The method of claim 6, wherein inserting said implant comprises substantially spanning the lumen of said blood vessel with said fibers.

10. The method of claim 6, wherein the blood vessel comprises a varicose vein.

11. A method of inhibiting migration of a bioabsorbable fibrous scaffold implanted within a lumen of a hollow anatomical structure, said method comprising:
   implanting a high void-content scaffold into the lumen of the hollow anatomical structure, the scaffold being resiliently compressible from an uncompressed configuration to a compressed configuration, the scaffold having a proximal portion and a distal portion and predominantly comprising a plurality of loose bioabsorbable fibers extending in a generally longitudinal direction, each of the fibers having a number of bends along its length such that, when the scaffold is in the uncompressed configuration, each of the fibers assumes a first configuration having a first length and defining a first radial width, and when the scaffold is in the compressed configuration, each of the fibers assumes a second configuration having a second length longer than the first length and defining a second radial width less than the first radial width, wherein implanting the scaffold into the lumen comprises implanting the scaffold in the compressed configuration with the fibers in the second configuration, and wherein the hollow anatomical structure comprises a blood vessel;

securing a proximal end of a tension member to tissue outside of the hollow anatomical structure, the tension member having a distal end that is coupled to the distal portion of the scaffold, the tension member extending proximally along the scaffold;

allowing the scaffold to return to the uncompressed configuration within the lumen through self-expansion of the fibers, whereby the fibers are returned from the second configuration to the first configuration, thereby creating a partial occlusion of the lumen that reduces blood flow through the lumen by 10%-90%, whereby the scaffold, in its uncompressed configuration, is substantially inhibited from migration within the lumen; and gradually creating a substantially complete occlusion of the lumen by permitting blood flowing through the lumen to infiltrate the high void content scaffold.

12. The method of claim 11, wherein permitting blood to infiltrate said scaffold comprises permitting antegrade blood flow to infiltrate said scaffold.

13. The method of claim 11, wherein said fibers span the lumen of said hollow anatomical structure, and permitting fluid to infiltrate said scaffold comprises permitting fluid flow between said fibers.

14. The method of claim 11, wherein gradually creating a substantially complete occlusion comprises causing tissue ingrowth into said scaffold.

15. The method of claim 11, wherein the hollow anatomical structure comprises a varicose vein.

16. A method of treating a hollow anatomical structure having a lumen, said method comprising:

inserting into the lumen of the hollow anatomical structure an implant and an anchor device passing longitudinally through the implant and having a distal end coupled to a distal portion of the implant, wherein the implant predominantly comprises a plurality of loose bioabsorbable fibers in substantial longitudinal alignment, each of the fibers being configured to have a greater length and a less tortuous configuration when the implant is compressed in a transverse direction, and to return to a lesser length and a more tortuous configuration when the implant is relieved of transverse compression, the implant being transversely compressed when inserted into the lumen, wherein the hollow anatomical structure comprises a blood vessel;

relieving the implant of transverse compression while it is in the lumen, whereby the implant is brought into engagement with the hollow anatomical structure as the fibers return to the more tortuous configuration, the implant thereby forming a high void-content scaffold that partially occludes the lumen and reduces blood flow through the lumen by 10%-90%;

positioning the implant such that said anchor device extends proximally substantially parallel along the fibers to a location upstream from the distal portion;

securing said anchor device to tissue outside of the hollow anatomical structure; and gradually creating a substantially complete occlusion of the lumen by allowing blood to infiltrate the voids of the scaffold.

17. The method of claim 16, wherein said hollow anatomical structure comprises a varicose vein.

18. The method of claim 16, wherein said fibers comprise a plurality of loose, bulked fibers.

19. The method of claim 16, wherein said anchor device comprises a tether.

20. The method of claim 16, wherein forming the high void-content scaffold comprises forming the high void-content scaffold that partially occludes the lumen and reduces blood flow through the lumen by 20%-80%.

* * * * *